US012378297B2

(12) United States Patent
Maus et al.

(10) Patent No.: US 12,378,297 B2
(45) Date of Patent: Aug. 5, 2025

(54) CHIMERIC ANTIGEN RECEPTOR T CELLS TARGETING THE TUMOR MICROENVIRONMENT

(71) Applicant: The General Hospital Corporation, Boston, MA (US)

(72) Inventors: Marcela V. Maus, Lexington, MA (US); Bryan Choi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 276 days.

(21) Appl. No.: 16/603,675

(22) PCT Filed: Apr. 16, 2018

(86) PCT No.: PCT/US2018/027783
§ 371 (c)(1),
(2) Date: Oct. 8, 2019

(87) PCT Pub. No.: WO2018/191748
PCT Pub. Date: Oct. 18, 2018

(65) Prior Publication Data
US 2020/0113940 A1    Apr. 16, 2020

Related U.S. Application Data

(60) Provisional application No. 62/629,593, filed on Feb. 12, 2018, provisional application No. 62/485,670, filed on Apr. 14, 2017.

(51) Int. Cl.
| | | |
|---|---|---|
| *A61K 40/31* | (2025.01) | |
| *A61K 40/11* | (2025.01) | |
| *A61K 40/42* | (2025.01) | |
| *A61P 35/00* | (2006.01) | |
| *C07K 14/725* | (2006.01) | |
| *C07K 16/28* | (2006.01) | |
| *C07K 16/30* | (2006.01) | |

(52) U.S. Cl.
CPC .......... *C07K 14/7051* (2013.01); *A61K 40/11* (2025.01); *A61K 40/31* (2025.01); *A61K 40/4204* (2025.01); *A61P 35/00* (2018.01); *C07K 16/2809* (2013.01); *C07K 16/2863* (2013.01); *C07K 16/2866* (2013.01); *C07K 16/30* (2013.01); *A61K 2239/31* (2023.05); *A61K 2239/38* (2023.05); *A61K 2239/47* (2023.05)

(58) Field of Classification Search
None
See application file for complete search history.

(56) References Cited

U.S. PATENT DOCUMENTS

| 8,822,647 B2 | 9/2014 | Jensen | |
|---|---|---|---|
| 9,349,368 B1 * | 5/2016 | Lebeau | .............. H04M 1/6058 |
| 9,394,368 B2 | 7/2016 | Brogdon et al. | |
| 9,567,399 B1 | 2/2017 | Campbell et al. | |
| 9,765,156 B2 | 9/2017 | June et al. | |
| 10,000,572 B2 | 6/2018 | Lucas et al. | |
| 10,308,717 B2 | 6/2019 | Brogdon et al. | |
| 10,696,749 B2 | 6/2020 | June et al. | |
| 11,046,782 B2 | 6/2021 | Li et al. | |
| 11,795,240 B2 | 10/2023 | June et al. | |
| 11,865,167 B2 | 1/2024 | Brogdon et al. | |
| 11,890,301 B2 | 2/2024 | June et al. | |
| 2009/0270485 A1 * | 10/2009 | Ko | .......................... A61P 35/00 435/325 |
| 2012/0148552 A1 | 6/2012 | Jensen | |
| 2013/0280220 A1 | 10/2013 | Ahmed et al. | |
| 2014/0322183 A1 | 10/2014 | Milone et al. | |
| 2014/0322275 A1 | 10/2014 | Brogdon et al. | |
| 2016/0151491 A1 | 6/2016 | Rabinovich et al. | |
| 2016/0200819 A1 | 7/2016 | Morgan et al. | |
| 2016/0251438 A1 | 9/2016 | Lucas et al. | |
| 2016/0272717 A1 | 9/2016 | Lucas et al. | |
| 2017/0002076 A1 | 1/2017 | Kim et al. | |
| 2017/0008963 A1 | 1/2017 | Brogdon et al. | |
| 2018/0022815 A1 | 1/2018 | Chang | |
| 2018/0162939 A1 | 6/2018 | Ma et al. | |
| 2019/0112380 A1 | 4/2019 | Chaudhary | |
| 2019/0307799 A1 | 10/2019 | Bonifant et al. | |
| 2019/0338015 A1 | 11/2019 | Juillerat et al. | |
| 2019/0345218 A1 | 11/2019 | Maus et al. | |
| 2019/0375815 A1 | 12/2019 | Engels et al. | |
| 2020/0095301 A1 | 3/2020 | Garcia et al. | |
| 2021/0038646 A1 | 2/2021 | Maus et al. | |
| 2023/0364139 A1 | 11/2023 | Chen et al. | |
| 2024/0075070 A1 | 3/2024 | Maus et al. | |

FOREIGN PATENT DOCUMENTS

| CN | 105283201 A | 1/2016 |
|---|---|---|
| CN | 105358576 A | 2/2016 |
| CN | 105658666 A | 6/2016 |

(Continued)

OTHER PUBLICATIONS

Fan et al. (Cancer Cell 24, 438-449, 2013). (Year: 2013).*
Sasaki et al. (Oncology Reports 17: 319-323, 2007). (Year: 2007).*
Lulli et al. (Oncotarget, vol. 7, No. 30, pp. 47777-47793, 2016). (Year: 2016).*
Vajdos et al. (J Mol Biol. Jul. 5, 2002;320(2):415-28). (Year: 2002).*
Bedouelle et al. (Febs J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Bonifant et al. (Molecular Therapy vol. 24 No. 9, 1615-1626, Sep. 2016). (Year: 2016).*
Hettich et al., Cancer Res; 76(16); 4673-83 (2016). (Year: 2016).*
Osada et al., Cancer Immunology, Immunotherapy, 64, 677-688 (2015). (Year: 2015).*

(Continued)

*Primary Examiner* — Zachary S Skelding
(74) *Attorney, Agent, or Firm* — Wolf, Greenfield & Sacks, P.C.

(57) ABSTRACT

The invention provides methods and compositions for use in treating cancer, which advantageously may be achieved by targeting of the tumor microenvironment.

24 Claims, 23 Drawing Sheets

Specification includes a Sequence Listing.

(56) References Cited

FOREIGN PATENT DOCUMENTS

| | | | | |
|---|---|---|---|---|
| CN | 105796597 A | 7/2016 | | |
| CN | 107002045 A | 8/2017 | | |
| CN | 107002084 A | 8/2017 | | |
| CN | 107326014 A | 11/2017 | | |
| WO | WO 96/40210 A1 | 12/1996 | | |
| WO | WO 99/54440 A1 | 10/1999 | | |
| WO | WO-2014011988 A2 * | 1/2014 | ............ | A61K 35/17 |
| WO | WO 2014/130657 A1 | 8/2014 | | |
| WO | WO-2014138306 A1 * | 9/2014 | ............ | A61P 35/00 |
| WO | WO 2015/124715 A1 | 8/2015 | | |
| WO | WO-2016016341 A1 * | 2/2016 | ............ | A61K 35/17 |
| WO | WO-2016070061 A1 * | 5/2016 | ............ | A61K 35/17 |
| WO | WO 2016/102965 A1 | 6/2016 | | |
| WO | WO 2016/130598 A1 | 8/2016 | | |
| WO | WO-2016187594 A1 * | 11/2016 | ............ | A61P 29/00 |
| WO | WO 2017/040324 A1 | 3/2017 | | |
| WO | WO 2017/049166 A1 | 3/2017 | | |
| WO | WO 2018/132427 A1 | 7/2018 | | |
| WO | WO 2018/191748 A1 | 10/2018 | | |
| WO | WO 2019/079034 A1 | 4/2019 | | |
| WO | WO 2019/157533 A1 | 8/2019 | | |
| WO | WO 2023/081808 A2 | 5/2023 | | |
| WO | WO 2023/201288 A1 | 10/2023 | | |

OTHER PUBLICATIONS

Torikai et al., Blood. 2012;119(24):5697-5705. (Year: 2012).*
Kim et al., PLoS One 6(4): e18556 (2011). (Year: 2011).*
Fajardo et al. (Cancer Res; 77(8); 2052-63. 2017). (Year: 2017).*
Curran et al. Enhancing antitumor efficacy of chimeric antigen receptor T cells through constitutive CD40L expression. Mol Ther. Apr. 2015;23(4):769-78. doi: 10.1038/mt.2015.4. Epub Jan. 13, 2015.
Frigault et al., Identification of chimeric antigen receptors that mediate constitutive or inducible proliferation of T cells. Cancer Immunol Res. Apr. 2015;3(4):356-67. doi: 10.1158/2326-6066.CIR-14-0186. Epub Jan. 19, 2015.
Hegde et al., Tandem CAR T cells targeting HER2 and IL13R?2 mitigate tumor antigen escape. J Clin Invest. Aug. 1, 2016;126(8):3036-52.
Jaspers et al., Development of CAR T cells designed to improve antitumor efficacy and safety. Pharmacol Ther. Oct. 2017;178:83-91. doi: 10.1016/j.pharmthera.2017.03.012. Epub Mar. 22, 2017.
Konerua et al., IL-12 secreting tumor-targeted chimeric antigen receptor T cells eradicate ovarian tumors in vivo. Oncoimmunology. Jan. 23, 2015;4(3):e994446. doi: 10.4161/2162402X.2014.994446. eCollection Mar. 2015.
Maus et al., Making Better Chimeric Antigen Receptors for Adoptive T-cell Therapy. Clin Cancer Res. Apr. 15, 2016;22(8):1875-84. doi: 10.1158/1078-0432.CCR-15-1433.
O'Rourke et al., A single dose of peripherally infused EGFRvIII-directed CAR T cells mediates antigen loss and induces adaptive resistance in patients with recurrent glioblastoma. Sci Transl Med. Jul. 19, 2017;9(399):eaaa0984. doi: 10.1126/scitranslmed.aaa0984.
Pegram et al., Tumor-targeted T cells modified to secrete IL-12 eradicate systemic tumors without need for prior conditioning. Blood. May 3, 2012;119(18):4133-41. doi: 10.1182/blood-2011-12-400044. Epub Feb. 21, 2012.
Pituch et al., Adoptive Transfer of IL13R?2-Specific Chimeric Antigen Receptor T Cells Creates a Pro-inflammatory Environment in Glioblastoma. Mol Ther. Apr. 4, 2018;26(4):986-995.
Ross et al., Bispecific T cell engager (BiTE®) antibody constructs can mediate bystander tumor cell killing. PLoS One. Aug. 24, 2017;12(8):e0183390.
Suarez et al., Chimeric antigen receptor T cells secreting anti-PD-L1 antibodies more effectively regress renal cell carcinoma in a humanized mouse model. Oncotarget. Jun. 7, 2016;7(23):34341-55. doi: 10.18632/oncotarget.9114.
Yeku et al., Armored CAR T-cells: utilizing cytokines and pro-inflammatory ligands to enhance CAR T-cell anti-tumour efficacy. Biochem Soc Trans. Apr. 15, 2016;44(2):412-8. doi: 10.1042/BST20150291.
U.S. Appl. No. 16/969,098, filed Aug. 11, 2020, Maus et al.
PCT/US2018/027783, Aug. 24, 2018, International Search Report and Written Opinion.
PCT/US2018/027783, Oct. 15, 2019, International Preliminary Report on Patentability.
EP 18784599, Dec. 11, 2020, Partial Supplementary European Search Report.
EP 18784599, Mar. 17, 2021, Extended European Search Report.
PCT/US2019/017727, Jul. 19, 2019, International Search Report and Written Opinion.
PCT/US2019/017727, Aug. 27, 2020, International Preliminary Report on Patentability.
Cuende et al., Monoclonal antibodies against GARP/TGF-β1 complexes inhibit the immunosuppressive activity of human regulatory T cells in vivo. Science Translational Medicine. Apr. 22, 2015;17(284):284ra56. 12 pages.
Hegde et al., A bispecific chimeric antigen receptor molecule enhances T cell activation through dual immunological synapse formation and offsets antigen escape in glioblastoma. J Immunother Cancer. 2015; 3(Suppl 2): O3.
Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016.
U.S. Appl. No. 16/475,717, filed Jul. 3, 2019, Maus et al.
EP 19751389, Feb. 28, 2022, Extended European Search Report.
Casset et al., A peptide mimetic of an anti-CD4 monoclonal antibody by rational design. Biochem Biophys Res Commun. Jul. 18, 2003;307(1):198-205. doi: 10.1016/s0006-291x(03)01131-8.
Chen et al., Selection and analysis of an optimized anti-VEGF antibody: crystal structure of an affinity-matured Fab in complex with antigen. J Mol Biol. Nov. 5, 1999;293(4):865-81. doi: 10.1006/jmbi.1999.3192.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84. doi: 10.4049/jimmunol.169.6.3076.
Lamminmaki et al., Crystal structure of a recombinant anti-estradiol Fab fragment in complex with 17beta -estradiol. J Biol Chem. Sep. 28, 2001;276(39):36687-94. doi: 10.1074/jbc.M102367200. Epub Jul. 12, 2001.
MacCallum et al., Antibody-antigen interactions: contact analysis and binding site topography. J Mol Biol. Oct. 11, 1996;262(5):732-45. doi: 10.1006/jmbi.1996.0548.
Padlan et al., Structure of an antibody-antigen complex: crystal structure of the HyHEL-10 Fab-lysozyme complex. Proc Natl Acad Sci U S A. Aug. 1989;86(15):5938-42. doi: 10.1073/pnas.86.15.5938.
Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.
Wu et al., Humanization of a murine monoclonal antibody by simultaneous optimization of framework and CDR residues. J Mol Biol. Nov. 19, 1999;294(1):151-62. doi: 10.1006/jmbi.1999.3141.
Li et al., Selective targeting of GARP-LTGFB axis in the tumor microenvironment augments PD-1 blockade via enhancing CD8+ T cell antitumor immunity. J Immunother Cancer. Sep. 2022;10(9):e005433. doi: 10.1136/jitc-2022-005433.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Riccione et al., Generation of CAR T cells for adoptive therapy in the context of glioblastoma standard of care. J Vis Exp. Feb. 16, 2015;(96):52397. doi: 10.3791/52397.
Schroeder, Jr. et al., Structure and function of immunoglobulins. J Allergy Clin Immunol. Feb. 2010;125(2 Suppl 2):S41-52. doi: 10.1016/j.jaci.2009.09.046.

(56) References Cited

OTHER PUBLICATIONS

Seidel et al., Anti-PD-1 and Anti-CTLA-4 Therapies in Cancer: Mechanisms of Action, Efficacy, and Limitations. Front Oncol. Mar. 28, 2018;8:86. doi: 10.3389/fonc.2018.00086. eCollection 2018.

Slaney et al., CARs versus BiTEs: A Comparison between T Cell-Redirection Strategies for Cancer Treatment. Cancer Discov. Aug. 2018;8(8):924-934. doi: 10.1158/2159-8290.CD-18-0297. Epub Jul. 16, 2018.

Wu et al., T cell engaging bispecific antibody (T-BsAb): From technology to therapeutics. Pharmacol Ther. Feb. 2018; 182:161-175. doi: 10.1016/j.pharmthera.2017.08.005. Epub Aug. 20, 2017. Author manuscript, 37 pages.

Cherkassky et al., Human CAR T cells with cell-intrinsic PD-1 checkpoint blockade resist tumor-mediated inhibition. J Clin Invest. Aug. 1, 2016;126(8):3130-44. doi: 10.1172/JCI83092. Epub Jul. 25, 2016.

Choi et al., CAR-T cells secreting BiTEs circumvent antigen escape without detectable toxicity. Nat Biotechnol. Sep. 2019;37(9):1049-1058. doi: 10.1038/s41587-019-0192-1. Epub Jul. 22, 2019.

Feucht et al., T-cell responses against CD19+ pediatric acute lymphoblastic leukemia mediated by bispecific T-cell engager (BiTE) are regulated contrarily by PD-L1 and CD80/CD86 on leukemic blasts. Oncotarget. Nov. 22, 2016;7(47):76902-76919. doi: 10.18632/oncotarget.12357.

Sun et al. GARP: a surface molecule of regulatory T cells that is involved in the regulatory function and TGF-β releasing. Oncotarget. Jul. 5, 2016;7(27):42826-42836. doi: 10.18632/oncotarget.8753.

Gall et al., T cells armed with anti-CD3 x anti-CD20 bispecific antibody enhance killing of CD20+ malignant B cells and bypass complement-mediated rituximab resistance in vitro. Exp Hematol. Apr. 2005;33(4):452-9. doi: 10.1016/j.exphem.2005.01.007.

\* cited by examiner

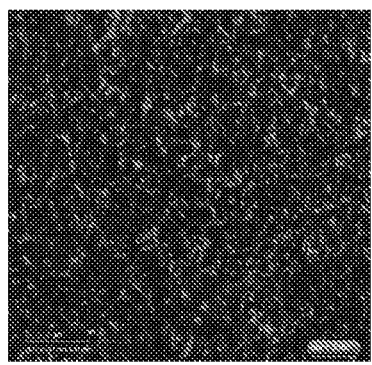 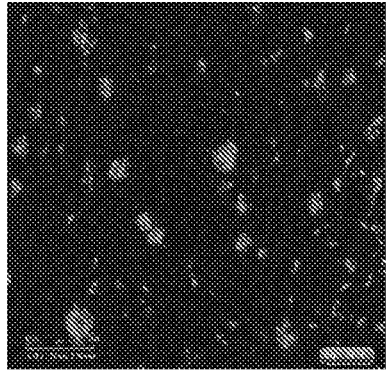 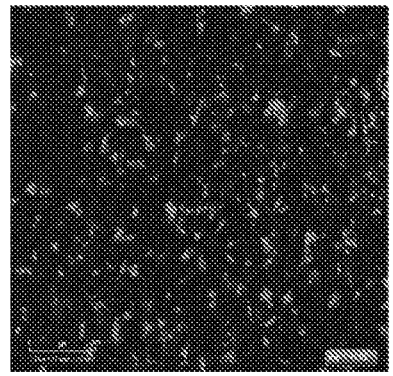
FIG. 5A      FIG. 5B      FIG. 5C
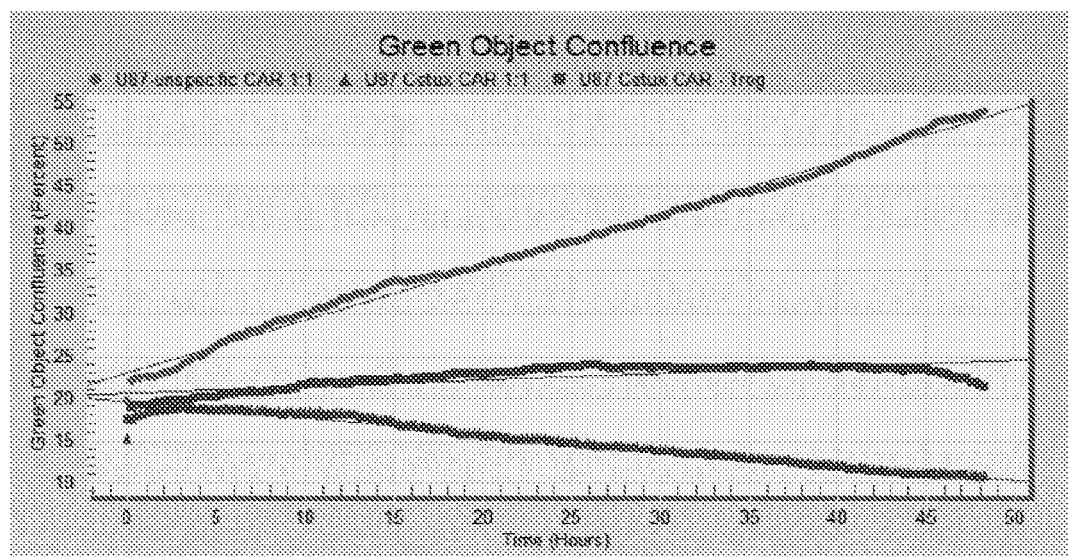
FIG. 5D

SEQUENCE LISTING

<160> NUMBER OF SEQ ID NOS: 68

<210> SEQ ID NO 1
<211> LENGTH: 351
<212> TYPE: PRT
<213> ORGANISM: Artificial Sequence
<220> FEATURE:
<223> OTHER INFORMATION: Synthetic Construct

<400> SEQUENCE: 1

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Leu Gly Asp Arg Val Thr Ile Thr Cys Gln Ala Ser Gln
        35                  40                  45

Ser Ile Ser Ser Tyr Leu Ala Trp Tyr Gln Gln Lys Pro Gly Gln Ala
    50                  55                  60

Pro Asn Ile Leu Ile Tyr Gly Ala Ser Arg Leu Lys Thr Gly Val Pro
65                  70                  75                  80

Ser Arg Phe Ser Gly Ser Gly Ser Gly Thr Ser Phe Thr Leu Thr Ile
                85                  90                  95

Ser Gly Leu Glu Ala Glu Asp Ala Gly Thr Tyr Tyr Cys Gln Gln Tyr
            100                 105                 110

Ala Ser Val Pro Val Thr Phe Gly Gln Gly Thr Lys Val Glu Leu Lys
        115                 120                 125

Thr Thr Thr Pro Ala Pro Arg Pro Pro Thr Pro Ala Pro Thr Ile Ala
    130                 135                 140

Ser Gln Pro Leu Ser Leu Arg Pro Glu Ala Cys Arg Pro Ala Ala Gly
145                 150                 155                 160

Gly Ala Val His Thr Arg Gly Leu Asp Phe Ala Cys Asp Ile Tyr Ile
                165                 170                 175

Trp Ala Pro Leu Ala Gly Thr Cys Gly Val Leu Leu Leu Ser Leu Val
            180                 185                 190

Ile Thr Leu Tyr Cys Lys Arg Gly Arg Lys Lys Leu Leu Tyr Ile Phe
        195                 200                 205

Lys Gln Pro Phe Met Arg Pro Val Gln Thr Thr Gln Glu Glu Asp Gly
    210                 215                 220

Cys Ser Cys Arg Phe Pro Glu Glu Glu Gly Gly Cys Glu Leu Arg
225                 230                 235                 240

Val Lys Phe Ser Arg Ser Ala Asp Ala Pro Ala Tyr Gln Gln Gly Gln
                245                 250                 255

Asn Gln Leu Tyr Asn Glu Leu Asn Leu Gly Arg Arg Glu Glu Tyr Asp
            260                 265                 270

Val Leu Asp Lys Arg Arg Gly Arg Asp Pro Glu Met Gly Gly Lys Pro
        275                 280                 285

Arg Arg Lys Asn Pro Gln Glu Gly Leu Tyr Asn Glu Leu Gln Lys Asp
    290                 295                 300

Lys Met Ala Glu Ala Tyr Ser Glu Ile Gly Met Lys Gly Glu Arg Arg
305                 310                 315                 320
```

```
Arg Gly Lys Gly His Asp Gly Leu Tyr Gln Gly Leu Ser Thr Ala Thr
                325                 330                 335

Lys Asp Thr Tyr Asp Ala Leu His Met Gln Ala Leu Pro Pro Arg
            340                 345                 350

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 107
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Asn Ile Leu Ile
        35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Ala Ser Val Pro Val
                85                  90                  95

Thr Phe Gly Gln Gly Thr Lys Val Glu Leu Lys
            100                 105

<210> SEQ ID NO 4
<211> LENGTH: 69
<212> TYPE: PRT
<213> ORGANISM: Artificial Sequence
<220> FEATURE:
<223> OTHER INFORMATION: Synthetic Construct

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 5
<211> LENGTH: 42
<212> TYPE: PRT
<213> ORGANISM: Artificial Sequence
<220> FEATURE:
<223> OTHER INFORMATION: Synthetic Construct

<400> SEQUENCE: 5

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Gly Gly Cys Glu Leu
            35                  40
```

<210> SEQ ID NO 6
<211> LENGTH: 112
<212> TYPE: PRT
<213> ORGANISM: Artificial Sequence
<220> FEATURE:
<223> OTHER INFORMATION: Synthetic Construct

<400> SEQUENCE: 6

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 7
<211> LENGTH: 530
<212> TYPE: PRT
<213> ORGANISM: Artificial Sequence
<220> FEATURE:
<223> OTHER INFORMATION: Synthetic Construct

<400> SEQUENCE: 7

```
Met Ala Leu Pro Val Thr Ala Leu Leu Leu Pro Leu Ala Leu Leu Leu
1               5                   10                  15

His Ala Ala Arg Pro Met Lys Leu Trp Leu Asn Trp Ile Phe Leu Val
            20                  25                  30

Thr Leu Leu Asn Asp Ile Gln Cys Glu Val Lys Leu Val Glu Ser Gly
            35                  40                  45

Gly Gly Leu Val Gln Pro Gly Gly Ser Leu Ser Leu Ser Cys Ala Ala
        50                  55                  60

Ser Gly Phe Thr Phe Thr Asp Tyr Tyr Met Ser Trp Val Arg Gln Pro
65                  70                  75                  80

Pro Gly Lys Ala Leu Glu Trp Leu Gly Phe Ile Arg Asn Lys Pro Asn
                85                  90                  95

Gly Tyr Thr Thr Glu Tyr Ser Ala Ser Val Lys Gly Arg Phe Thr Ile
```

```
            100                 105                 110
Ser Arg Asp Asn Ser Gln Ser Ile Leu Tyr Leu Gln Met Asn Val Leu
            115                 120                 125

Arg Ala Glu Asp Ser Ala Thr Tyr Tyr Cys Ala Arg Tyr Thr Gly Gly
    130                 135                 140

Gly Tyr Phe Asp Tyr Trp Gly Gln Gly Thr Thr Leu Thr Val Ser Ser
145                 150                 155                 160

Gly Gly Gly Gly Ser Gly Gly Gly Ser Gly Gly Gly Gly Ser Gly
                165                 170                 175

Gly Gly Gly Ser Met Met Ser Ala Gln Phe Leu Gly Leu Leu Leu
            180                 185                 190

Leu Cys Phe Gln Gly Thr Arg Cys Asp Ile Gln Met Thr Gln Thr Thr
    195                 200                 205

Ser Ser Leu Ser Ala Ser Leu Gly Asp Arg Leu Thr Ile Ser Cys Arg
    210                 215                 220

Ala Ser Gln Asp Ile Ser Asn Tyr Leu Asn Trp Tyr Gln Gln Lys Pro
225                 230                 235                 240

Asp Gly Thr Val Lys Leu Leu Ile Tyr Tyr Thr Ser Arg Leu His Ser
                245                 250                 255

Gly Val Pro Ser Arg Phe Ser Gly Ser Gly Ser Gly Thr Asp Tyr Ser
            260                 265                 270

Leu Thr Ile Ser Asn Leu Glu Gln Ala Asp Ile Ala Thr Tyr Phe Cys
        275                 280                 285

Gln Gln Gly Asp Thr Leu Pro Trp Thr Phe Gly Gly Gly Thr Lys Leu
    290                 295                 300

Glu Ile Lys Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Gln
            420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
        515                 520                 525
```

Pro Arg
    530

<210> SEQ ID NO 8
<211> LENGTH: 21
<212> TYPE: PRT
<213> ORGANISM: Artificial Sequence
<220> FEATURE:
<223> OTHER INFORMATION: Synthetic Construct

<400> SEQUENCE: 8

Met Ala Leu Pro Val Thr Ala Leu Leu Leu Pro Leu Ala Leu Leu Leu
1               5                   10                  15

His Ala Ala Arg Pro
            20

<210> SEQ ID NO 9
<211> LENGTH: 286
<212> TYPE: PRT
<213> ORGANISM: Artificial Sequence
<220> FEATURE:
<223> OTHER INFORMATION: Synthetic Construct

<400> SEQUENCE: 9

Met Lys Leu Trp Leu Asn Trp Ile Phe Leu Val Thr Leu Leu Asn Asp
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Ser Trp Val Arg Gln Pro Pro Gly Lys Ala Leu
    50                  55                  60

Glu Trp Leu Gly Phe Ile Arg Asn Lys Pro Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Val Leu Arg Ala Glu Asp Ser
            100                 105                 110

Ala Thr Tyr Tyr Cys Ala Arg Tyr Thr Gly Gly Gly Tyr Phe Asp Tyr
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Gly Gly Gly Gly Ser Met
145                 150                 155                 160

Met Ser Ser Ala Gln Phe Leu Gly Leu Leu Leu Leu Cys Phe Gln Gly
                165                 170                 175

Thr Arg Cys Asp Ile Gln Met Thr Gln Thr Thr Ser Ser Leu Ser Ala
            180                 185                 190

Ser Leu Gly Asp Arg Leu Thr Ile Ser Cys Arg Ala Ser Gln Asp Ile
        195                 200                 205

Ser Asn Tyr Leu Asn Trp Tyr Gln Gln Lys Pro Asp Gly Thr Val Lys
    210                 215                 220

Leu Leu Ile Tyr Tyr Thr Ser Arg Leu His Ser Gly Val Pro Ser Arg
225                 230                 235                 240

Phe Ser Gly Ser Gly Ser Gly Thr Asp Tyr Ser Leu Thr Ile Ser Asn
                245                 250                 255

Leu Glu Gln Ala Asp Ile Ala Thr Tyr Phe Cys Gln Gln Gly Asp Thr

```
                    260                 265                 270
Leu Pro Trp Thr Phe Gly Gly Gly Thr Lys Leu Glu Ile Lys
        275                 280                 285

<210> SEQ ID NO 10
<211> LENGTH: 69
<212> TYPE: PRT
<213> ORGANISM: Artificial Sequence
<220> FEATURE:
<223> OTHER INFORMATION: Synthetic Construct

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 11
<211> LENGTH: 42
<212> TYPE: PRT
<213> ORGANISM: Artificial Sequence
<220> FEATURE:
<223> OTHER INFORMATION: Synthetic Construct

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 12
<211> LENGTH: 112
<212> TYPE: PRT
<213> ORGANISM: Artificial Sequence
<220> FEATURE:
<223> OTHER INFORMATION: Synthetic Construct

<400> SEQUENCE: 12

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 13
<211> LENGTH: 530
<212> TYPE: PRT
<213> ORGANISM: Artificial Sequence
<220> FEATURE:
<223> OTHER INFORMATION: Synthetic Construct

<400> SEQUENCE: 13

Met Ala Leu Pro Val Thr Ala Leu Leu Leu Pro Leu Ala Leu Leu Leu
1               5                   10                  15

His Ala Ala Arg Pro Met Met Ser Ser Ala Gln Phe Leu Gly Leu Leu
            20                  25                  30

Leu Leu Cys Phe Gln Gly Thr Arg Cys Asp Ile Gln Met Thr Gln Thr
        35                  40                  45

Thr Ser Ser Leu Ser Ala Ser Leu Gly Asp Arg Leu Thr Ile Ser Cys
    50                  55                  60

Arg Ala Ser Gln Asp Ile Ser Asn Tyr Leu Asn Trp Tyr Gln Lys
65                  70                  75                  80

Pro Asp Gly Thr Val Lys Leu Leu Ile Tyr Tyr Thr Ser Arg Leu His
                85                  90                  95

Ser Gly Val Pro Ser Arg Phe Ser Gly Ser Gly Ser Gly Thr Asp Tyr
            100                 105                 110

Ser Leu Thr Ile Ser Asn Leu Glu Gln Ala Asp Ile Ala Thr Tyr Phe
        115                 120                 125

Cys Gln Gln Gly Asp Thr Leu Pro Trp Thr Phe Gly Gly Gly Thr Lys
    130                 135                 140

Leu Glu Ile Lys Gly Gly Gly Gly Ser Gly Gly Gly Ser Gly Gly
145                 150                 155                 160

Gly Gly Ser Gly Gly Gly Gly Ser Met Lys Leu Trp Leu Asn Trp Ile
                165                 170                 175

Phe Leu Val Thr Leu Leu Asn Asp Ile Gln Cys Glu Val Lys Leu Val
            180                 185                 190

Glu Ser Gly Gly Gly Leu Val Gln Pro Gly Gly Ser Leu Ser Leu Ser
        195                 200                 205

Cys Ala Ala Ser Gly Phe Thr Phe Thr Asp Tyr Tyr Met Ser Trp Val
    210                 215                 220

Arg Gln Pro Pro Gly Lys Ala Leu Glu Trp Leu Gly Phe Ile Arg Asn
225                 230                 235                 240

Lys Pro Asn Gly Tyr Thr Thr Glu Tyr Ser Ala Ser Val Lys Gly Arg
                245                 250                 255

Phe Thr Ile Ser Arg Asp Asn Ser Gln Ser Ile Leu Tyr Leu Gln Met
            260                 265                 270

Asn Val Leu Arg Ala Glu Asp Ser Ala Thr Tyr Tyr Cys Ala Arg Tyr
        275                 280                 285

Thr Gly Gly Gly Tyr Phe Asp Tyr Trp Gly Gln Gly Thr Thr Leu Thr
    290                 295                 300

Val Ser Ser Thr Thr Thr Pro Ala Pro Arg Pro Pro Thr Pro Ala Pro
305                 310                 315                 320

Thr Ile Ala Ser Gln Pro Leu Ser Leu Arg Pro Glu Ala Cys Arg Pro
                325                 330                 335

Ala Ala Gly Gly Ala Val His Thr Arg Gly Leu Asp Phe Ala Cys Asp
            340                 345                 350

Ile Tyr Ile Trp Ala Pro Leu Ala Gly Thr Cys Gly Val Leu Leu Leu
        355                 360                 365

Ser Leu Val Ile Thr Leu Tyr Cys Lys Arg Gly Arg Lys Leu Leu
        370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Gly Gly Cys
                405                 410                 415

Glu Leu Arg Val Lys Phe Ser Arg Ser Ala Asp Ala Pro Ala Tyr Gln
                420                 425                 430

Gln Gly Gln Asn Gln Leu Tyr Asn Glu Leu Asn Leu Gly Arg Arg Glu
                435                 440                 445

Glu Tyr Asp Val Leu Asp Lys Arg Arg Gly Arg Asp Pro Glu Met Gly
                450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
                500                 505                 510

Thr Ala Thr Lys Asp Thr Tyr Asp Ala Leu His Met Gln Ala Leu Pro
                515                 520                 525

Pro Arg
    530

<210> SEQ ID NO 14
<211> LENGTH: 21
<212> TYPE: PRT
<213> ORGANISM: Artificial Sequence
<220> FEATURE:
<223> OTHER INFORMATION: Synthetic Construct

<400> SEQUENCE: 14

Met Ala Leu Pro Val Thr Ala Leu Leu Leu Pro Leu Ala Leu Leu Leu
1               5                   10                  15

His Ala Ala Arg Pro
            20

<210> SEQ ID NO 15
<211> LENGTH: 286
<212> TYPE: PRT
<213> ORGANISM: Artificial Sequence
<220> FEATURE:
<223> OTHER INFORMATION: Synthetic Construct

<400> SEQUENCE: 15

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Leu Thr Ile Ser Cys Arg Ala Ser Gln Asp
            35                  40                  45

Ile Ser Asn Tyr Leu Asn Trp Tyr Gln Gln Lys Pro Asp Gly Thr Val
        50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Ala Asp Ile Ala Thr Tyr Phe Cys Gln Gln Gly Asp

```
                100             105             110
Thr Leu Pro Trp Thr Phe Gly Gly Gly Thr Lys Leu Glu Ile Lys Gly
            115                 120                 125
Gly Gly Gly Ser Gly Gly Gly Ser Gly Gly Gly Ser Gly Gly
            130                 135             140
Gly Gly Ser Met Lys Leu Trp Leu Asn Trp Ile Phe Leu Val Thr Leu
145                 150                 155                 160
Leu Asn Asp Ile Gln Cys Glu Val Lys Leu Val Glu Ser Gly Gly Gly
                165                 170                 175
Leu Val Gln Pro Gly Gly Ser Leu Ser Leu Ser Cys Ala Ala Ser Gly
                180                 185                 190
Phe Thr Phe Thr Asp Tyr Tyr Met Ser Trp Val Arg Gln Pro Pro Gly
                195                 200                 205
Lys Ala Leu Glu Trp Leu Gly Phe Ile Arg Asn Lys Pro Asn Gly Tyr
            210                 215                 220
Thr Thr Glu Tyr Ser Ala Ser Val Lys Gly Arg Phe Thr Ile Ser Arg
225                 230                 235                 240
Asp Asn Ser Gln Ser Ile Leu Tyr Leu Gln Met Asn Val Leu Arg Ala
                245                 250                 255
Glu Asp Ser Ala Thr Tyr Tyr Cys Ala Arg Tyr Thr Gly Gly Gly Tyr
                260                 265                 270
Phe Asp Tyr Trp Gly Gln Gly Thr Thr Leu Thr Val Ser Ser
            275                 280                 285

<210> SEQ ID NO 16
<211> LENGTH: 69
<212> TYPE: PRT
<213> ORGANISM: Artificial Sequence
<220> FEATURE:
<223> OTHER INFORMATION: Synthetic Construct

<400> SEQUENCE: 16

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
                20                  25                  30
Gly Ala Val His Thr Arg Gly Leu Asp Phe Ala Cys Asp Ile Tyr Ile
            35                  40                  45
Trp Ala Pro Leu Ala Gly Thr Cys Gly Val Leu Leu Leu Ser Leu Val
        50                  55                  60
Ile Thr Leu Tyr Cys
65

<210> SEQ ID NO 17
<211> LENGTH: 42
<212> TYPE: PRT
<213> ORGANISM: Artificial Sequence
<220> FEATURE:
<223> OTHER INFORMATION: Synthetic Construct

<400> SEQUENCE: 17

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
                20                  25                  30
Pro Glu Glu Glu Glu Gly Gly Cys Glu Leu
            35                  40
```

```
<210> SEQ ID NO 18
<211> LENGTH: 112
<212> TYPE: PRT
<213> ORGANISM: Artificial Sequence
<220> FEATURE:
<223> OTHER INFORMATION: Synthetic Construct

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 654
<212> TYPE: PRT
<213> ORGANISM: Artificial Sequence
<220> FEATURE:
<223> OTHER INFORMATION: Synthetic Construct

<400> SEQUENCE: 19

Met Ala Leu Pro Val Thr Ala Leu Leu Leu Pro Leu Ala Leu Leu Leu
1               5                   10                  15

His Ala Ala Arg Pro Gln Val Gln Leu Lys Gln Ser Gly Pro Gly Leu
            20                  25                  30

Val Gln Pro Ser Gln Ser Leu Ser Ile Thr Cys Thr Val Ser Gly Phe
        35                  40                  45

Ser Leu Thr Asn Tyr Gly Val His Trp Val Arg Gln Ser Pro Gly Lys
    50                  55                  60

Gly Leu Glu Trp Leu Gly Val Ile Trp Ser Gly Gly Asn Thr Asp Tyr
65                  70                  75                  80

Asn Thr Pro Phe Thr Ser Arg Leu Ser Ile Asn Lys Asp Asn Ser Lys
                85                  90                  95

Ser Gln Val Phe Phe Lys Met Asn Ser Leu Gln Ser Asn Asp Thr Ala
            100                 105                 110

Ile Tyr Tyr Cys Ala Arg Ala Leu Thr Tyr Tyr Asp Tyr Glu Phe Ala
        115                 120                 125

Tyr Trp Gly Gln Gly Thr Leu Val Thr Val Ser Ala Gly Gly Gly Gly
    130                 135                 140

Ser Gly Gly Gly Gly Ser Gly Gly Gly Gly Ser Gly Gly Gly Gly Ser
145                 150                 155                 160

Asp Ile Leu Leu Thr Gln Ser Pro Val Ile Leu Ser Val Ser Pro Gly
                165                 170                 175

Glu Arg Val Ser Phe Ser Cys Arg Ala Ser Gln Ser Ile Gly Thr Asn
            180                 185                 190

Ile His Trp Tyr Gln Gln Arg Thr Asn Gly Ser Pro Arg Leu Leu Ile
        195                 200                 205
```

```
Lys Tyr Ala Ser Glu Ser Ile Ser Gly Ile Pro Ser Arg Phe Ser Gly
    210                 215                 220
Ser Gly Ser Gly Thr Asp Phe Thr Leu Ser Ile Asn Ser Val Glu Ser
225                 230                 235                 240
Glu Asp Ile Ala Asp Tyr Tyr Cys Gln Gln Asn Asn Asn Trp Pro Thr
                245                 250                 255
Thr Phe Gly Ala Gly Thr Lys Leu Glu Leu Lys Thr Thr Thr Pro Ala
            260                 265                 270
Pro Arg Pro Pro Thr Pro Ala Pro Thr Ile Ala Ser Gln Pro Leu Ser
        275                 280                 285
Leu Arg Pro Glu Ala Cys Arg Pro Ala Ala Gly Gly Ala Val His Thr
290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
            340                 345                 350
Arg Pro Val Gln Thr Thr Gln Glu Glu Asp Gly Cys Ser Cys Arg Phe
        355                 360                 365
Pro Glu Glu Glu Glu Gly Gly Cys Glu Leu Arg Val Lys Phe Ser Arg
370                 375                 380
Ser Ala Asp Ala Pro Ala Tyr Gln Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
            420                 425                 430
Gln Glu Gly Leu Tyr Asn Glu Leu Gln Lys Asp Lys Met Ala Glu Ala
        435                 440                 445
Tyr Ser Glu Ile Gly Met Lys Gly Glu Arg Arg Arg Gly Lys Gly His
450                 455                 460
Asp Gly Leu Tyr Gln Gly Leu Ser Thr Ala Thr Lys Asp Thr Tyr Asp
465                 470                 475                 480
Ala Leu His Met Gln Ala Leu Pro Pro Arg Pro Gly Ser Gly Ser Gly
                485                 490                 495
Ala Thr Asn Phe Ser Leu Leu Lys Gln Ala Gly Asp Val Glu Glu Asn
            500                 505                 510
Pro Gly Pro Arg Thr Ala Met Glu Thr Asp Thr Leu Leu Leu Trp Val
        515                 520                 525
Leu Leu Leu Trp Val Pro Gly Ser Thr Gly Asp Ile Gln Met Thr
530                 535                 540
Gln Ser Pro Ser Ser Leu Ser Ala Ser Leu Gly Asp Arg Val Thr Ile
545                 550                 555                 560
Thr Cys Gln Ala Ser Gln Ser Ile Ser Ser Tyr Leu Ala Trp Tyr Gln
                565                 570                 575
Gln Lys Pro Gly Gln Ala Pro Asn Ile Leu Ile Tyr Gly Ala Ser Arg
            580                 585                 590
Leu Lys Thr Gly Val Pro Ser Arg Phe Ser Gly Ser Gly Ser Gly Thr
        595                 600                 605
Ser Phe Thr Leu Thr Ile Ser Gly Leu Glu Ala Glu Asp Ala Gly Thr
610                 615                 620
```

```
Tyr Tyr Cys Gln Gln Tyr Ala Ser Val Pro Val Thr Phe Gly Gln Gly
625                 630                 635                 640

Thr Lys Val Glu Leu Lys His His His His His Ser Gly
                645                 650

<210> SEQ ID NO 20
<211> LENGTH: 21
<212> TYPE: PRT
<213> ORGANISM: Artificial Sequence
<220> FEATURE:
<223> OTHER INFORMATION: Synthetic Construct

<400> SEQUENCE: 20

Met Ala Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 246
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Gly Gly Gly Gly Ser Gly Gly Gly Gly
            115                 120                 125

Ser Gly Gly Gly Gly Ser Gly Gly Gly Gly Ser Asp Ile Leu Leu Thr
        130                 135                 140

Gln Ser Pro Val Ile Leu Ser Val Ser Pro Gly Glu Arg Val Ser Phe
145                 150                 155                 160

Ser Cys Arg Ala Ser Gln Ser Ile Gly Thr Asn Ile His Trp Tyr Gln
                165                 170                 175

Gln Arg Thr Asn Gly Ser Pro Arg Leu Leu Ile Lys Tyr Ala Ser Glu
                180                 185                 190

Ser Ile Ser Gly Ile Pro Ser Arg Phe Ser Gly Ser Gly Ser Gly Thr
            195                 200                 205

Asp Phe Thr Leu Ser Ile Asn Ser Val Glu Ser Glu Asp Ile Ala Asp
        210                 215                 220

Tyr Tyr Cys Gln Gln Asn Asn Asn Trp Pro Thr Thr Phe Gly Ala Gly
225                 230                 235                 240

Thr Lys Leu Glu Leu Lys
                245
```

<210> SEQ ID NO 22
<211> LENGTH: 69
<212> TYPE: PRT
<213> ORGANISM: Artificial Sequence
<220> FEATURE:
<223> OTHER INFORMATION: Synthetic Construct

<400> SEQUENCE: 22

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 23
<211> LENGTH: 42
<212> TYPE: PRT
<213> ORGANISM: Artificial Sequence
<220> FEATURE:
<223> OTHER INFORMATION: Synthetic Construct

<400> SEQUENCE: 23

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 24
<211> LENGTH: 112
<212> TYPE: PRT
<213> ORGANISM: Artificial Sequence
<220> FEATURE:
<223> OTHER INFORMATION: Synthetic Construct

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 107

```
<212> TYPE: PRT
<213> ORGANISM: Artificial Sequence
<220> FEATURE:
<223> OTHER INFORMATION: Synthetic Construct

<400> SEQUENCE: 25

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Asn Ile Leu Ile
        35                  40                  45

Tyr Gly Ala Ser Arg Leu Lys Thr Gly Val Pro Ser Arg Phe Ser Gly
50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Ala Ser Val Pro Val
                85                  90                  95

Thr Phe Gly Gln Gly Thr Lys Val Glu Leu Lys
            100                 105

<210> SEQ ID NO 26
<211> LENGTH: 1006
<212> TYPE: PRT
<213> ORGANISM: Artificial Sequence
<220> FEATURE:
<223> OTHER INFORMATION: Synthetic Construct

<400> SEQUENCE: 26

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
50                  55                  60

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
            100                 105                 110

Ser Ser Gly Gly Gly Gly Ser Gly Gly Gly Ser Gly Gly Gly Gly
            115                 120                 125

Ser His Met Asp Val Val Met Thr Gln Ser Pro Leu Thr Leu Ser Val
    130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Arg Ile Ser Arg Val Glu Ala Glu Asp Leu Gly Ile Tyr Tyr Cys
    210                 215                 220
```

```
Trp Gln Gly Thr His Phe Pro Gly Thr Phe Gly Gly Thr Lys Leu
225                 230                 235                 240

Glu Ile Lys Thr Thr Thr Pro Ala Pro Arg Pro Pro Thr Pro Ala Pro
                    245                 250                 255

Thr Ile Ala Ser Gln Pro Leu Ser Leu Arg Pro Glu Ala Cys Arg Pro
                260                 265                 270

Ala Ala Gly Gly Ala Val His Thr Arg Gly Leu Asp Phe Ala Cys Asp
            275                 280                 285

Ile Tyr Ile Trp Ala Pro Leu Ala Gly Thr Cys Gly Val Leu Leu Leu
        290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg Gly Ser Gly Ala Thr Asn Phe Ser Leu Leu Lys Gln Ala Gly
465                 470                 475                 480

Asp Val Glu Glu Asn Pro Gly Pro Pro Arg Met Glu Thr Asp Thr Leu
                485                 490                 495

Leu Leu Trp Val Leu Leu Leu Trp Val Pro Gly Ser Thr Gly Asp Asp
            500                 505                 510

Ile Leu Leu Thr Gln Ser Pro Val Ile Leu Ser Val Ser Pro Gly Glu
        515                 520                 525

Arg Val Ser Phe Ser Cys Arg Ala Ser Gln Ser Ile Gly Thr Asn Ile
    530                 535                 540

His Trp Tyr Gln Gln Arg Thr Asn Gly Ser Pro Arg Leu Leu Ile Lys
545                 550                 555                 560

Tyr Ala Ser Glu Ser Ile Ser Gly Ile Pro Ser Arg Phe Ser Gly Ser
                565                 570                 575

Gly Ser Gly Thr Asp Phe Thr Leu Ser Ile Asn Ser Val Glu Ser Glu
            580                 585                 590

Asp Ile Ala Asp Tyr Tyr Cys Gln Gln Asn Asn Asn Trp Pro Thr Thr
        595                 600                 605

Phe Gly Ala Gly Thr Lys Leu Glu Leu Lys Gly Gly Gly Gly Ser Gly
    610                 615                 620

Gly Gly Gly Ser Gly Gly Gly Gly Ser Gln Val Gln Leu Lys Gln Ser
625                 630                 635                 640
```

Gly Pro Gly Leu Val Gln Pro Ser Gln Ser Leu Ser Ile Thr Cys Thr
            645                 650                 655

Val Ser Gly Phe Ser Leu Thr Asn Tyr Gly Val His Trp Val Arg Gln
        660                 665                 670

Ser Pro Gly Lys Gly Leu Glu Trp Leu Gly Val Ile Trp Ser Gly Gly
    675                 680                 685

Asn Thr Asp Tyr Asn Thr Pro Phe Thr Ser Arg Leu Ser Ile Asn Lys
690                 695                 700

Asp Asn Ser Lys Ser Gln Val Phe Phe Lys Met Asn Ser Leu Gln Ser
705                 710                 715                 720

Asn Asp Thr Ala Ile Tyr Tyr Cys Ala Arg Ala Leu Thr Tyr Tyr Asp
                725                 730                 735

Tyr Glu Phe Ala Tyr Trp Gly Gln Gly Thr Leu Val Thr Val Ser Ala
            740                 745                 750

Gly Gly Gly Gly Ser Asp Ile Lys Leu Gln Gln Ser Gly Ala Glu Leu
        755                 760                 765

Ala Arg Pro Gly Ala Ser Val Lys Met Ser Cys Lys Thr Ser Gly Tyr
    770                 775                 780

Thr Phe Thr Arg Tyr Thr Met His Trp Val Lys Gln Arg Pro Gly Gln
785                 790                 795                 800

Gly Leu Glu Trp Ile Gly Tyr Ile Asn Pro Ser Arg Gly Tyr Thr Asn
                805                 810                 815

Tyr Asn Gln Lys Phe Lys Asp Lys Ala Thr Leu Thr Thr Asp Lys Ser
            820                 825                 830

Ser Ser Thr Ala Tyr Met Gln Leu Ser Ser Leu Thr Ser Glu Asp Ser
        835                 840                 845

Ala Val Tyr Tyr Cys Ala Arg Tyr Tyr Asp Asp His Tyr Cys Leu Asp
    850                 855                 860

Tyr Trp Gly Gln Gly Thr Thr Leu Thr Val Ser Ser Val Glu Gly Gly
865                 870                 875                 880

Ser Gly Gly Ser Gly Gly Ser Gly Gly Ser Gly Gly Val Asp Asp Ile
                885                 890                 895

Gln Leu Thr Gln Ser Pro Ala Ile Met Ser Ala Ser Pro Gly Glu Lys
            900                 905                 910

Val Thr Met Thr Cys Arg Ala Ser Ser Ser Val Ser Tyr Met Asn Trp
        915                 920                 925

Tyr Gln Gln Lys Ser Gly Thr Ser Pro Lys Arg Trp Ile Tyr Asp Thr
    930                 935                 940

Ser Lys Val Ala Ser Gly Val Pro Tyr Arg Phe Ser Gly Ser Gly Ser
945                 950                 955                 960

Gly Thr Ser Tyr Ser Leu Thr Ile Ser Ser Met Glu Ala Glu Asp Ala
                965                 970                 975

Ala Thr Tyr Tyr Cys Gln Gln Trp Ser Ser Asn Pro Leu Thr Phe Gly
            980                 985                 990

Ala Gly Thr Lys Leu Glu Leu Lys  His His His His  His
        995                 1000                1005

<210> SEQ ID NO 27
<211> LENGTH: 243
<212> TYPE: PRT
<213> ORGANISM: Artificial Sequence
<220> FEATURE:
<223> OTHER INFORMATION: Synthetic Construct

<400> SEQUENCE: 27

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
            35                  40                  45

Gly Arg Ile Asp Pro Glu Asn Asp Glu Thr Lys Tyr Gly Pro Ile Phe
50                  55                  60

Gln Gly Arg Ala Thr Ile Thr Ala Asp Thr Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
                100                 105                 110

Ser Ser Gly Gly Gly Gly Ser Gly Gly Gly Gly Ser Gly Gly Gly Gly
                115                 120                 125

Ser His Met Asp Val Val Met Thr Gln Ser Pro Leu Thr Leu Ser Val
                130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
                180                 185                 190

Gly Val Pro Asp Arg Phe Thr Gly Ser Gly Ser Gly Thr Asp Phe Thr
                195                 200                 205

Leu Arg Ile Ser Arg Val Glu Ala Glu Asp Leu Gly Ile Tyr Tyr Cys
                210                 215                 220

Trp Gln Gly Thr His Phe Pro Gly Thr Phe Gly Gly Gly Thr Lys Leu
225                 230                 235                 240

Glu Ile Lys

<210> SEQ ID NO 28
<211> LENGTH: 69
<212> TYPE: PRT
<213> ORGANISM: Artificial Sequence
<220> FEATURE:
<223> OTHER INFORMATION: Synthetic Construct

<400> SEQUENCE: 28

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
                35                  40                  45

Trp Ala Pro Leu Ala Gly Thr Cys Gly Val Leu Leu Leu Ser Leu Val
                50                  55                  60

Ile Thr Leu Tyr Cys
65

<210> SEQ ID NO 29
<211> LENGTH: 42
<212> TYPE: PRT
<213> ORGANISM: Artificial Sequence
<220> FEATURE:
<223> OTHER INFORMATION: Synthetic Construct

```
<400> SEQUENCE: 29

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 31
<211> LENGTH: 22
<212> TYPE: PRT
<213> ORGANISM: Artificial Sequence
<220> FEATURE:
<223> OTHER INFORMATION: Synthetic Construct

<400> SEQUENCE: 31

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 32
<211> LENGTH: 21
<212> TYPE: PRT
<213> ORGANISM: Artificial Sequence
<220> FEATURE:
<223> OTHER INFORMATION: Synthetic Construct

<400> SEQUENCE: 32

Met Glu Thr Asp Thr Leu Leu Leu Trp Val Leu Leu Leu Trp Val Pro
1               5                   10                  15

Gly Ser Thr Gly Asp
            20

<210> SEQ ID NO 33
<211> LENGTH: 241
<212> TYPE: PRT
```

<213> ORGANISM: Artificial Sequence
<220> FEATURE:
<223> OTHER INFORMATION: Synthetic Construct

<400> SEQUENCE: 33

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Lys Gln
            115                 120                 125

Ser Gly Pro Gly Leu Val Gln Pro Ser Gln Ser Leu Ser Ile Thr Cys
130                 135                 140

Thr Val Ser Gly Phe Ser Leu Thr Asn Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Asn Thr Asp Tyr Asn Thr Pro Phe Thr Ser Arg Leu Ser Ile Asn
            180                 185                 190

Lys Asp Asn Ser Lys Ser Gln Val Phe Phe Lys Met Asn Ser Leu Gln
        195                 200                 205

Ser Asn Asp Thr Ala Ile Tyr Tyr Cys Ala Arg Ala Leu Thr Tyr Tyr
    210                 215                 220

Asp Tyr Glu Phe Ala Tyr Trp Gly Gln Gly Thr Leu Val Thr Val Ser
225                 230                 235                 240

Ala
```

<210> SEQ ID NO 34
<211> LENGTH: 243
<212> TYPE: PRT
<213> ORGANISM: Artificial Sequence
<220> FEATURE:
<223> OTHER INFORMATION: Synthetic Construct

<400> SEQUENCE: 34

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
```

```
                    85                  90                  95
Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
                115                 120                 125

Gly Ser Gly Gly Ser Gly Val Asp Asp Ile Gln Leu Thr Gln Ser
            130                 135                 140

Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
                210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 35
<211> LENGTH: 1009
<212> TYPE: PRT
<213> ORGANISM: Artificial Sequence
<220> FEATURE:
<223> OTHER INFORMATION: Synthetic Construct

<400> SEQUENCE: 35

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
                20                  25                  30

Tyr Ile His Trp Val Arg Gln Met Pro Gly Lys Gly Leu Glu Trp Met
            35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
                100                 105                 110

Ser Ser Gly Gly Gly Gly Ser Gly Gly Gly Ser Gly Gly Gly Gly
            115                 120                 125

Ser Gly Gly Gly Gly Ser Asp Val Val Met Thr Gln Ser Pro Asp Ser
            130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
                195                 200                 205
```

```
Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg Gly Ser Gly Ala Thr Asn Phe Ser Leu Leu Lys
465                 470                 475                 480

Gln Ala Gly Asp Val Glu Glu Asn Pro Gly Pro Pro Arg Met Glu Thr
                485                 490                 495

Asp Thr Leu Leu Leu Trp Val Leu Leu Leu Trp Val Pro Gly Ser Thr
            500                 505                 510

Gly Asp Asp Ile Leu Leu Thr Gln Ser Pro Val Ile Leu Ser Val Ser
        515                 520                 525

Pro Gly Glu Arg Val Ser Phe Ser Cys Arg Ala Ser Gln Ser Ile Gly
    530                 535                 540

Thr Asn Ile His Trp Tyr Gln Gln Arg Thr Asn Gly Ser Pro Arg Leu
545                 550                 555                 560

Leu Ile Lys Tyr Ala Ser Glu Ser Ile Ser Gly Ile Pro Ser Arg Phe
                565                 570                 575

Ser Gly Ser Gly Ser Gly Thr Asp Phe Thr Leu Ser Ile Asn Ser Val
            580                 585                 590

Glu Ser Glu Asp Ile Ala Asp Tyr Tyr Cys Gln Gln Asn Asn Asn Trp
        595                 600                 605

Pro Thr Thr Phe Gly Ala Gly Thr Lys Leu Glu Leu Lys Gly Gly Gly
    610                 615                 620
```

```
Gly Ser Gly Gly Gly Ser Gly Gly Gly Ser Gln Val Gln Leu
625                 630                 635                 640

Lys Gln Ser Gly Pro Gly Leu Val Gln Pro Ser Gln Ser Leu Ser Ile
            645                 650                 655

Thr Cys Thr Val Ser Gly Phe Ser Leu Thr Asn Tyr Gly Val His Trp
            660                 665                 670

Val Arg Gln Ser Pro Gly Lys Gly Leu Glu Trp Leu Gly Val Ile Trp
            675                 680                 685

Ser Gly Gly Asn Thr Asp Tyr Asn Thr Pro Phe Thr Ser Arg Leu Ser
690                 695                 700

Ile Asn Lys Asp Asn Ser Lys Ser Gln Val Phe Phe Lys Met Asn Ser
705                 710                 715                 720

Leu Gln Ser Asn Asp Thr Ala Ile Tyr Tyr Cys Ala Arg Ala Leu Thr
            725                 730                 735

Tyr Tyr Asp Tyr Glu Phe Ala Tyr Trp Gly Gln Gly Thr Leu Val Thr
            740                 745                 750

Val Ser Ala Gly Gly Gly Gly Ser Asp Ile Lys Leu Gln Gln Ser Gly
            755                 760                 765

Ala Glu Leu Ala Arg Pro Gly Ala Ser Val Lys Met Ser Cys Lys Thr
770                 775                 780

Ser Gly Tyr Thr Phe Thr Arg Tyr Thr Met His Trp Val Lys Gln Arg
785                 790                 795                 800

Pro Gly Gln Gly Leu Glu Trp Ile Gly Tyr Ile Asn Pro Ser Arg Gly
            805                 810                 815

Tyr Thr Asn Tyr Asn Gln Lys Phe Lys Asp Lys Ala Thr Leu Thr Thr
            820                 825                 830

Asp Lys Ser Ser Ser Thr Ala Tyr Met Gln Leu Ser Ser Leu Thr Ser
            835                 840                 845

Glu Asp Ser Ala Val Tyr Tyr Cys Ala Arg Tyr Tyr Asp Asp His Tyr
850                 855                 860

Cys Leu Asp Tyr Trp Gly Gln Gly Thr Thr Leu Thr Val Ser Ser Val
865                 870                 875                 880

Glu Gly Gly Ser Gly Gly Ser Gly Gly Ser Gly Gly Ser Gly Gly Val
            885                 890                 895

Asp Asp Ile Gln Leu Thr Gln Ser Pro Ala Ile Met Ser Ala Ser Pro
            900                 905                 910

Gly Glu Lys Val Thr Met Thr Cys Arg Ala Ser Ser Ser Val Ser Tyr
            915                 920                 925

Met Asn Trp Tyr Gln Gln Lys Ser Gly Thr Ser Pro Lys Arg Trp Ile
930                 935                 940

Tyr Asp Thr Ser Lys Val Ala Ser Gly Val Pro Tyr Arg Phe Ser Gly
945                 950                 955                 960

Ser Gly Ser Gly Thr Ser Tyr Ser Leu Thr Ile Ser Ser Met Glu Ala
            965                 970                 975

Glu Asp Ala Ala Thr Tyr Tyr Cys Gln Gln Trp Ser Ser Asn Pro Leu
            980                 985                 990

Thr Phe Gly Ala Gly Thr Lys Leu Glu Leu Lys His His His His His
            995                 1000                1005

His

<210> SEQ ID NO 36
<211> LENGTH: 246
<212> TYPE: PRT
<213> ORGANISM: Artificial Sequence
```

```
<220> FEATURE:
<223> OTHER INFORMATION: Synthetic Construct

<400> SEQUENCE: 36

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
            115                 120                 125

Ser Gly Gly Gly Gly Ser Asp Val Val Met Thr Gln Ser Pro Asp Ser
            130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
            210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 37
<211> LENGTH: 69
<212> TYPE: PRT
<213> ORGANISM: Artificial Sequence
<220> FEATURE:
<223> OTHER INFORMATION: Synthetic Construct

<400> SEQUENCE: 37

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
            50                  55                  60

Ile Thr Leu Tyr Cys
65
```

```
<210> SEQ ID NO 38
<211> LENGTH: 42
<212> TYPE: PRT
<213> ORGANISM: Artificial Sequence
<220> FEATURE:
<223> OTHER INFORMATION: Synthetic Construct

<400> SEQUENCE: 38

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 39
<211> LENGTH: 112
<212> TYPE: PRT
<213> ORGANISM: Artificial Sequence
<220> FEATURE:
<223> OTHER INFORMATION: Synthetic Construct

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 40
<211> LENGTH: 22
<212> TYPE: PRT
<213> ORGANISM: Artificial Sequence
<220> FEATURE:
<223> OTHER INFORMATION: Synthetic Construct

<400> SEQUENCE: 40

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 41
<211> LENGTH: 21
<212> TYPE: PRT
<213> ORGANISM: Artificial Sequence
<220> FEATURE:
<223> OTHER INFORMATION: Synthetic Construct

<400> SEQUENCE: 41

Met Glu Thr Asp Thr Leu Leu Leu Trp Val Leu Leu Leu Trp Val Pro
1               5                   10                  15

Gly Ser Thr Gly Asp
```

<210> SEQ ID NO 42
<211> LENGTH: 241
<212> TYPE: PRT
<213> ORGANISM: Artificial Sequence
<220> FEATURE:
<223> OTHER INFORMATION: Synthetic Construct

<400> SEQUENCE: 42

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Lys Gln
            115                 120                 125

Ser Gly Pro Gly Leu Val Gln Pro Ser Gln Ser Leu Ser Ile Thr Cys
    130                 135                 140

Thr Val Ser Gly Phe Ser Leu Thr Asn Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Asn Thr Asp Tyr Asn Thr Pro Phe Thr Ser Arg Leu Ser Ile Asn
            180                 185                 190

Lys Asp Asn Ser Lys Ser Gln Val Phe Phe Lys Met Asn Ser Leu Gln
        195                 200                 205

Ser Asn Asp Thr Ala Ile Tyr Tyr Cys Ala Arg Ala Leu Thr Tyr Tyr
    210                 215                 220

Asp Tyr Glu Phe Ala Tyr Trp Gly Gln Gly Thr Leu Val Thr Val Ser
225                 230                 235                 240

Ala
```

<210> SEQ ID NO 43
<211> LENGTH: 243
<212> TYPE: PRT
<213> ORGANISM: Artificial Sequence
<220> FEATURE:
<223> OTHER INFORMATION: Synthetic Construct

<400> SEQUENCE: 43

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 44
<211> LENGTH: 1018
<212> TYPE: PRT
<213> ORGANISM: Artificial Sequence
<220> FEATURE:
<223> OTHER INFORMATION: Synthetic Construct

<400> SEQUENCE: 44

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
                20                  25                  30

Tyr Ile His Trp Val Arg Gln Met Pro Gly Lys Gly Leu Glu Trp Met
            35                  40                  45

Gly Arg Ile Asp Pro Glu Asn Asp Glu Thr Lys Tyr Gly Pro Ile Phe
        50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

```
Gln Lys Pro Gly Gln Pro Pro Lys Arg Leu Ile Ser Leu Val Ser Lys
                180                 185                 190

Leu Asp Ser Gly Val Pro Asp Arg Phe Ser Gly Ser Gly Ser Gly Thr
            195                 200                 205

Asp Phe Thr Leu Thr Ile Ser Ser Leu Gln Ala Glu Asp Val Ala Val
210                 215                 220

Tyr Tyr Cys Trp Gln Gly Thr His Phe Pro Gly Thr Phe Gly Gly Gly
225                 230                 235                 240

Thr Lys Val Glu Ile Lys Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg Gly Ser Gly Ala Thr Asn Phe Ser Leu Leu Lys
465                 470                 475                 480

Gln Ala Gly Asp Val Glu Glu Asn Pro Gly Pro Arg Met Glu Thr
                485                 490                 495

Asp Thr Leu Leu Leu Trp Val Leu Leu Leu Trp Val Pro Gly Ser Thr
            500                 505                 510

Gly Asp Asp Ile Gln Leu Thr Gln Ser Pro Ala Ser Leu Ala Val Ser
        515                 520                 525

Leu Gly Gln Arg Ala Thr Ile Ser Cys Lys Ala Ser Gln Ser Val Asp
    530                 535                 540

Tyr Asp Gly Asp Ser Tyr Leu Asn Trp Tyr Gln Gln Ile Pro Gly Gln
545                 550                 555                 560

Pro Pro Lys Leu Leu Ile Tyr Asp Ala Ser Asn Leu Val Ser Gly Ile
                565                 570                 575

Pro Pro Arg Phe Ser Gly Ser Gly Ser Gly Thr Asp Phe Thr Leu Asn
            580                 585                 590
```

```
Ile His Pro Val Glu Lys Val Asp Ala Ala Thr Tyr His Cys Gln Gln
            595                 600                 605

Ser Thr Glu Asp Pro Trp Thr Phe Gly Gly Gly Thr Lys Leu Glu Ile
    610                 615                 620

Lys Gly Gly Gly Gly Ser Gly Gly Gly Gly Ser Gly Gly Gly Gly Ser
625                 630                 635                 640

Gln Val Gln Leu Gln Gln Ser Gly Ala Glu Leu Val Arg Pro Gly Ser
                645                 650                 655

Ser Val Lys Ile Ser Cys Lys Ala Ser Gly Tyr Ala Phe Ser Ser Tyr
                660                 665                 670

Trp Met Asn Trp Val Lys Gln Arg Pro Gly Gln Gly Leu Glu Trp Ile
        675                 680                 685

Gly Gln Ile Trp Pro Gly Asp Gly Asp Thr Asn Tyr Asn Gly Lys Phe
    690                 695                 700

Lys Gly Lys Ala Thr Leu Thr Ala Asp Glu Ser Ser Ser Thr Ala Tyr
705                 710                 715                 720

Met Gln Leu Ser Ser Leu Ala Ser Glu Asp Ser Ala Val Tyr Phe Cys
                725                 730                 735

Ala Arg Arg Glu Thr Thr Thr Val Gly Arg Tyr Tyr Tyr Ala Met Asp
            740                 745                 750

Tyr Trp Gly Gln Gly Thr Thr Val Thr Val Ser Ser Gly Gly Gly Gly
        755                 760                 765

Ser Asp Ile Lys Leu Gln Gln Ser Gly Ala Glu Leu Ala Arg Pro Gly
    770                 775                 780

Ala Ser Val Lys Met Ser Cys Lys Thr Ser Gly Tyr Thr Phe Thr Arg
785                 790                 795                 800

Tyr Thr Met His Trp Val Lys Gln Arg Pro Gly Gln Gly Leu Glu Trp
                805                 810                 815

Ile Gly Tyr Ile Asn Pro Ser Arg Gly Tyr Thr Asn Tyr Asn Gln Lys
            820                 825                 830

Phe Lys Asp Lys Ala Thr Leu Thr Thr Asp Lys Ser Ser Ser Thr Ala
        835                 840                 845

Tyr Met Gln Leu Ser Ser Leu Thr Ser Glu Asp Ser Ala Val Tyr Tyr
    850                 855                 860

Cys Ala Arg Tyr Tyr Asp Asp His Tyr Cys Leu Asp Tyr Trp Gly Gln
865                 870                 875                 880

Gly Thr Thr Leu Thr Val Ser Ser Val Glu Gly Gly Ser Gly Gly Ser
                885                 890                 895

Gly Gly Ser Gly Gly Ser Gly Val Asp Asp Ile Gln Leu Thr Gln
            900                 905                 910

Ser Pro Ala Ile Met Ser Ala Ser Pro Gly Glu Lys Val Thr Met Thr
    915                 920                 925

Cys Arg Ala Ser Ser Ser Val Ser Tyr Met Asn Trp Tyr Gln Gln Lys
930                 935                 940

Ser Gly Thr Ser Pro Lys Arg Trp Ile Tyr Asp Thr Ser Lys Val Ala
945                 950                 955                 960

Ser Gly Val Pro Tyr Arg Phe Ser Gly Ser Gly Ser Gly Thr Ser Tyr
                965                 970                 975

Ser Leu Thr Ile Ser Ser Met Glu Ala Glu Asp Ala Ala Thr Tyr Tyr
            980                 985                 990

Cys Gln Gln Trp Ser Ser Asn Pro  Leu Thr Phe Gly Ala  Gly Thr Lys
        995                 1000                 1005

Leu Glu  Leu Lys His His His  His His His
```

<210> SEQ ID NO 45
<211> LENGTH: 246
<212> TYPE: PRT
<213> ORGANISM: Artificial Sequence
<220> FEATURE:
<223> OTHER INFORMATION: Synthetic Construct

<400> SEQUENCE: 45

```
Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 46
<211> LENGTH: 69
<212> TYPE: PRT
<213> ORGANISM: Artificial Sequence
<220> FEATURE:
<223> OTHER INFORMATION: Synthetic Construct

<400> SEQUENCE: 46

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45
```

Trp Ala Pro Leu Ala Gly Thr Cys Gly Val Leu Leu Ser Leu Val
            50                  55                  60

Ile Thr Leu Tyr Cys
 65

<210> SEQ ID NO 47
<211> LENGTH: 42
<212> TYPE: PRT
<213> ORGANISM: Artificial Sequence
<220> FEATURE:
<223> OTHER INFORMATION: Synthetic Construct

<400> SEQUENCE: 47

Lys Arg Gly Arg Lys Lys Leu Leu Tyr Ile Phe Lys Gln Pro Phe Met
  1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
         35                  40

<210> SEQ ID NO 48
<211> LENGTH: 112
<212> TYPE: PRT
<213> ORGANISM: Artificial Sequence
<220> FEATURE:
<223> OTHER INFORMATION: Synthetic Construct

<400> SEQUENCE: 48

Arg Val Lys Phe Ser Arg Ser Ala Asp Ala Pro Ala Tyr Gln Gln Gly
  1               5                  10                  15

Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 49
<211> LENGTH: 22
<212> TYPE: PRT
<213> ORGANISM: Artificial Sequence
<220> FEATURE:
<223> OTHER INFORMATION: Synthetic Construct

<400> SEQUENCE: 49

Gly Ser Gly Ala Thr Asn Phe Ser Leu Leu Lys Gln Ala Gly Asp Val
  1               5                  10                  15

Glu Glu Asn Pro Gly Pro
             20

<210> SEQ ID NO 50
<211> LENGTH: 21
<212> TYPE: PRT
<213> ORGANISM: Artificial Sequence
<220> FEATURE:
<223> OTHER INFORMATION: Synthetic Construct

<400> SEQUENCE: 50

Met Glu Thr Asp Thr Leu Leu Leu Trp Val Leu Leu Leu Trp Val Pro
1               5                   10                  15

Gly Ser Thr Gly Asp
            20

<210> SEQ ID NO 51
<211> LENGTH: 255
<212> TYPE: PRT
<213> ORGANISM: Artificial Sequence
<220> FEATURE:
<223> OTHER INFORMATION: Synthetic Construct

<400> SEQUENCE: 51

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser
                245                 250                 255

<210> SEQ ID NO 52
<211> LENGTH: 243
<212> TYPE: PRT
<213> ORGANISM: Artificial Sequence
<220> FEATURE:
<223> OTHER INFORMATION: Synthetic Construct

<400> SEQUENCE: 52

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 53
<211> LENGTH: 985
<212> TYPE: PRT
<213> ORGANISM: Artificial Sequence
<220> FEATURE:
<223> OTHER INFORMATION: Synthetic Construct

<400> SEQUENCE: 53

Met Glu Thr Asp Thr Leu Leu Leu Trp Val Leu Leu Leu Trp Val Pro
1               5                   10                  15

Gly Ser Thr Gly Asp Asp Ile Leu Leu Thr Gln Ser Pro Val Ile Leu
            20                  25                  30

Ser Val Ser Pro Gly Glu Arg Val Ser Phe Ser Cys Arg Ala Ser Gln
        35                  40                  45

Ser Ile Gly Thr Asn Ile His Trp Tyr Gln Gln Arg Thr Asn Gly Ser
    50                  55                  60

Pro Arg Leu Leu Ile Lys Tyr Ala Ser Glu Ser Ile Ser Gly Ile Pro
65                  70                  75                  80

Ser Arg Phe Ser Gly Ser Gly Ser Gly Thr Asp Phe Thr Leu Ser Ile
                85                  90                  95

Asn Ser Val Glu Ser Glu Asp Ile Ala Asp Tyr Tyr Cys Gln Gln Asn
            100                 105                 110

Asn Asn Trp Pro Thr Thr Phe Gly Ala Gly Thr Lys Leu Glu Leu Lys
        115                 120                 125

```
Gly Gly Gly Ser Gly Gly Gly Ser Gly Gly Gly Ser Gln
    130             135             140

Val Gln Leu Lys Gln Ser Gly Pro Gly Leu Val Gln Pro Ser Gln Ser
145             150             155             160

Leu Ser Ile Thr Cys Thr Val Ser Gly Phe Ser Leu Thr Asn Tyr Gly
                165             170             175

Val His Trp Val Arg Gln Ser Pro Gly Lys Gly Leu Glu Trp Leu Gly
            180             185             190

Val Ile Trp Ser Gly Gly Asn Thr Asp Tyr Asn Thr Pro Phe Thr Ser
        195             200             205

Arg Leu Ser Ile Asn Lys Asp Asn Ser Lys Ser Gln Val Phe Phe Lys
    210             215             220

Met Asn Ser Leu Gln Ser Asn Asp Thr Ala Ile Tyr Tyr Cys Ala Arg
225             230             235             240

Ala Leu Thr Tyr Tyr Asp Tyr Glu Phe Ala Tyr Trp Gly Gln Gly Thr
                245             250             255

Leu Val Thr Val Ser Ala Gly Gly Gly Ser Asp Ile Lys Leu Gln
            260             265             270

Gln Ser Gly Ala Glu Leu Ala Arg Pro Gly Ala Ser Val Lys Met Ser
    275             280             285

Cys Lys Thr Ser Gly Tyr Thr Phe Thr Arg Tyr Thr Met His Trp Val
290             295             300

Lys Gln Arg Pro Gly Gln Gly Leu Glu Trp Ile Gly Tyr Ile Asn Pro
305             310             315             320

Ser Arg Gly Tyr Thr Asn Tyr Asn Gln Lys Phe Lys Asp Lys Ala Thr
                325             330             335

Leu Thr Thr Asp Lys Ser Ser Ser Thr Ala Tyr Met Gln Leu Ser Ser
            340             345             350

Leu Thr Ser Glu Asp Ser Ala Val Tyr Tyr Cys Ala Arg Tyr Tyr Asp
        355             360             365

Asp His Tyr Cys Leu Asp Tyr Trp Gly Gln Gly Thr Thr Leu Thr Val
    370             375             380

Ser Ser Val Glu Gly Gly Ser Gly Gly Ser Gly Gly Ser Gly Gly Ser
385             390             395             400

Gly Gly Val Asp Asp Ile Gln Leu Thr Gln Ser Pro Ala Ile Met Ser
                405             410             415

Ala Ser Pro Gly Glu Lys Val Thr Met Thr Cys Arg Ala Ser Ser Ser
            420             425             430

Val Ser Tyr Met Asn Trp Tyr Gln Gln Lys Ser Gly Thr Ser Pro Lys
        435             440             445

Arg Trp Ile Tyr Asp Thr Ser Lys Val Ala Ser Gly Val Pro Tyr Arg
    450             455             460

Phe Ser Gly Ser Gly Ser Gly Thr Ser Tyr Ser Leu Thr Ile Ser Ser
465             470             475             480

Met Glu Ala Glu Asp Ala Ala Thr Tyr Tyr Cys Gln Gln Trp Ser Ser
                485             490             495

Asn Pro Leu Thr Phe Gly Ala Gly Thr Lys Leu Glu Leu Lys His His
            500             505             510

His His His His Glu Ile Gln Leu Val Gln Ser Gly Ala Glu Val Lys
        515             520             525

Lys Pro Gly Glu Ser Leu Arg Ile Ser Cys Lys Gly Ser Gly Phe Asn
    530             535             540

Ile Glu Asp Tyr Tyr Ile His Trp Val Arg Gln Met Pro Gly Lys Gly
```

```
                545                 550                 555                 560
Leu Glu Trp Met Gly Arg Ile Asp Pro Glu Asn Asp Glu Thr Lys Tyr
                565                 570                 575
Gly Pro Ile Phe Gln Gly His Val Thr Ile Ser Ala Asp Thr Ser Ile
                580                 585                 590
Asn Thr Val Tyr Leu Gln Trp Ser Ser Leu Lys Ala Ser Asp Thr Ala
                595                 600                 605
Met Tyr Tyr Cys Ala Phe Arg Gly Gly Val Tyr Trp Gly Gln Gly Thr
                610                 615                 620
Thr Val Thr Val Ser Ser Gly Gly Gly Ser Gly Gly Gly Gly Ser
625                 630                 635                 640
Gly Gly Gly Gly Ser Gly Gly Gly Ser Asp Val Val Met Thr Gln
                645                 650                 655
Ser Pro Asp Ser Leu Ala Val Ser Leu Gly Glu Arg Ala Thr Ile Asn
                660                 665                 670
Cys Lys Ser Ser Gln Ser Leu Leu Asp Ser Asp Gly Lys Thr Tyr Leu
                675                 680                 685
Asn Trp Leu Gln Gln Lys Pro Gly Gln Pro Pro Lys Arg Leu Ile Ser
                690                 695                 700
Leu Val Ser Lys Leu Asp Ser Gly Val Pro Asp Arg Phe Ser Gly Ser
705                 710                 715                 720
Gly Ser Gly Thr Asp Phe Thr Leu Thr Ile Ser Ser Leu Gln Ala Glu
                725                 730                 735
Asp Val Ala Val Tyr Tyr Cys Trp Gln Gly Thr His Phe Pro Gly Thr
                740                 745                 750
Phe Gly Gly Gly Thr Lys Val Glu Ile Lys Thr Thr Thr Pro Ala Pro
                755                 760                 765
Arg Pro Pro Thr Pro Ala Pro Thr Ile Ala Ser Gln Pro Leu Ser Leu
                770                 775                 780
Arg Pro Glu Ala Cys Arg Pro Ala Ala Gly Gly Ala Val His Thr Arg
785                 790                 795                 800
Gly Leu Asp Phe Ala Cys Asp Ile Tyr Ile Trp Ala Pro Leu Ala Gly
                805                 810                 815
Thr Cys Gly Val Leu Leu Leu Ser Leu Val Ile Thr Leu Tyr Cys Lys
                820                 825                 830
Arg Gly Arg Lys Lys Leu Leu Tyr Ile Phe Lys Gln Pro Phe Met Arg
                835                 840                 845
Pro Val Gln Thr Thr Gln Glu Glu Asp Gly Cys Ser Cys Arg Phe Pro
850                 855                 860
Glu Glu Glu Glu Gly Gly Cys Glu Leu Arg Val Lys Phe Ser Arg Ser
865                 870                 875                 880
Ala Asp Ala Pro Ala Tyr Gln Gln Gly Gln Asn Gln Leu Tyr Asn Glu
                885                 890                 895
Leu Asn Leu Gly Arg Arg Glu Glu Tyr Asp Val Leu Asp Lys Arg Arg
                900                 905                 910
Gly Arg Asp Pro Glu Met Gly Gly Lys Pro Arg Arg Lys Asn Pro Gln
                915                 920                 925
Glu Gly Leu Tyr Asn Glu Leu Gln Lys Asp Lys Met Ala Glu Ala Tyr
                930                 935                 940
Ser Glu Ile Gly Met Lys Gly Glu Arg Arg Arg Gly Lys Gly His Asp
945                 950                 955                 960
Gly Leu Tyr Gln Gly Leu Ser Thr Ala Thr Lys Asp Thr Tyr Asp Ala
                965                 970                 975
```

Leu His Met Gln Ala Leu Pro Pro Arg
            980             985

<210> SEQ ID NO 54
<211> LENGTH: 21
<212> TYPE: PRT
<213> ORGANISM: Artificial Sequence
<220> FEATURE:
<223> OTHER INFORMATION: Synthetic Construct

<400> SEQUENCE: 54

Met Glu Thr Asp Thr Leu Leu Leu Trp Val Leu Leu Leu Trp Val Pro
1               5                   10                  15

Gly Ser Thr Gly Asp
            20

<210> SEQ ID NO 55
<211> LENGTH: 241
<212> TYPE: PRT
<213> ORGANISM: Artificial Sequence
<220> FEATURE:
<223> OTHER INFORMATION: Synthetic Construct

<400> SEQUENCE: 55

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Lys Gln
        115                 120                 125

Ser Gly Pro Gly Leu Val Gln Pro Ser Gln Ser Leu Ser Ile Thr Cys
    130                 135                 140

Thr Val Ser Gly Phe Ser Leu Thr Asn Tyr Gly Val His Trp Val Arg
145                 150                 155                 160

Gln Ser Pro Gly Lys Gly Leu Glu Trp Leu Gly Val Ile Trp Ser Gly
                165                 170                 175

Gly Asn Thr Asp Tyr Asn Thr Pro Phe Thr Ser Arg Leu Ser Ile Asn
            180                 185                 190

Lys Asp Asn Ser Lys Ser Gln Val Phe Phe Lys Met Asn Ser Leu Gln
        195                 200                 205

Ser Asn Asp Thr Ala Ile Tyr Tyr Cys Ala Arg Ala Leu Thr Tyr Tyr
    210                 215                 220

Asp Tyr Glu Phe Ala Tyr Trp Gly Gln Gly Thr Leu Val Thr Val Ser
225                 230                 235                 240

Ala

<210> SEQ ID NO 56

```
<211> LENGTH: 243
<212> TYPE: PRT
<213> ORGANISM: Artificial Sequence
<220> FEATURE:
<223> OTHER INFORMATION: Synthetic Construct

<400> SEQUENCE: 56

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 57
<211> LENGTH: 246
<212> TYPE: PRT
<213> ORGANISM: Artificial Sequence
<220> FEATURE:
<223> OTHER INFORMATION: Synthetic Construct

<400> SEQUENCE: 57

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80
```

```
Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Ser Gly Gly Gly Gly
        115                 120                 125

Ser Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 58
<211> LENGTH: 69
<212> TYPE: PRT
<213> ORGANISM: Artificial Sequence
<220> FEATURE:
<223> OTHER INFORMATION: Synthetic Construct

<400> SEQUENCE: 58

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 59
<211> LENGTH: 42
<212> TYPE: PRT
<213> ORGANISM: Artificial Sequence
<220> FEATURE:
<223> OTHER INFORMATION: Synthetic Construct

<400> SEQUENCE: 59

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

```
<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 61
<211> LENGTH: 994
<212> TYPE: PRT
<213> ORGANISM: Artificial Sequence
<220> FEATURE:
<223> OTHER INFORMATION: Synthetic Construct

<400> SEQUENCE: 61

Met Glu Thr Asp Thr Leu Leu Leu Trp Val Leu Leu Leu Trp Val Pro
1               5                   10                  15

Gly Ser Thr Gly Asp Asp Ile Gln Leu Thr Gln Ser Pro Ala Ser Leu
            20                  25                  30

Ala Val Ser Leu Gly Gln Arg Ala Thr Ile Ser Cys Lys Ala Ser Gln
        35                  40                  45

Ser Val Asp Tyr Asp Gly Asp Ser Tyr Leu Asn Trp Tyr Gln Gln Ile
    50                  55                  60

Pro Gly Gln Pro Pro Lys Leu Leu Ile Tyr Asp Ala Ser Asn Leu Val
65                  70                  75                  80

Ser Gly Ile Pro Pro Arg Phe Ser Gly Ser Gly Ser Gly Thr Asp Phe
                85                  90                  95

Thr Leu Asn Ile His Pro Val Glu Lys Val Asp Ala Ala Thr Tyr His
            100                 105                 110

Cys Gln Gln Ser Thr Glu Asp Pro Trp Thr Phe Gly Gly Gly Thr Lys
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Gln Ser Gly Ala Glu Leu Val Arg
145                 150                 155                 160

Pro Gly Ser Ser Val Lys Ile Ser Cys Lys Ala Ser Gly Tyr Ala Phe
                165                 170                 175

Ser Ser Tyr Trp Met Asn Trp Val Lys Gln Arg Pro Gly Gln Gly Leu
            180                 185                 190

Glu Trp Ile Gly Gln Ile Trp Pro Gly Asp Gly Asp Thr Asn Tyr Asn
        195                 200                 205
```

```
Gly Lys Phe Lys Gly Lys Ala Thr Leu Thr Ala Asp Glu Ser Ser Ser
210                 215                 220
Thr Ala Tyr Met Gln Leu Ser Ser Leu Ala Ser Glu Asp Ser Ala Val
225                 230                 235                 240
Tyr Phe Cys Ala Arg Arg Glu Thr Thr Val Gly Arg Tyr Tyr Tyr
            245                 250                 255
Ala Met Asp Tyr Trp Gly Gln Gly Thr Thr Val Thr Val Ser Ser Gly
                260                 265                 270
Gly Gly Gly Ser Asp Ile Lys Leu Gln Gln Ser Gly Ala Glu Leu Ala
            275                 280                 285
Arg Pro Gly Ala Ser Val Lys Met Ser Cys Lys Thr Ser Gly Tyr Thr
290                 295                 300
Phe Thr Arg Tyr Thr Met His Trp Val Lys Gln Arg Pro Gly Gln Gly
305                 310                 315                 320
Leu Glu Trp Ile Gly Tyr Ile Asn Pro Ser Arg Gly Tyr Thr Asn Tyr
                325                 330                 335
Asn Gln Lys Phe Lys Asp Lys Ala Thr Leu Thr Thr Asp Lys Ser Ser
            340                 345                 350
Ser Thr Ala Tyr Met Gln Leu Ser Ser Leu Thr Ser Glu Asp Ser Ala
            355                 360                 365
Val Tyr Tyr Cys Ala Arg Tyr Tyr Asp Asp His Tyr Cys Leu Asp Tyr
370                 375                 380
Trp Gly Gln Gly Thr Thr Leu Thr Val Ser Ser Val Glu Gly Gly Ser
385                 390                 395                 400
Gly Gly Ser Gly Gly Ser Gly Gly Ser Gly Gly Val Asp Asp Ile Gln
            405                 410                 415
Leu Thr Gln Ser Pro Ala Ile Met Ser Ala Ser Pro Gly Glu Lys Val
            420                 425                 430
Thr Met Thr Cys Arg Ala Ser Ser Ser Val Ser Tyr Met Asn Trp Tyr
            435                 440                 445
Gln Gln Lys Ser Gly Thr Ser Pro Lys Arg Trp Ile Tyr Asp Thr Ser
450                 455                 460
Lys Val Ala Ser Gly Val Pro Tyr Arg Phe Ser Gly Ser Gly Ser Gly
465                 470                 475                 480
Thr Ser Tyr Ser Leu Thr Ile Ser Ser Met Glu Ala Glu Asp Ala Ala
            485                 490                 495
Thr Tyr Tyr Cys Gln Gln Trp Ser Ser Asn Pro Leu Thr Phe Gly Ala
            500                 505                 510
Gly Thr Lys Leu Glu Leu Lys His His His His His His Glu Ile Gln
            515                 520                 525
Leu Val Gln Ser Gly Ala Glu Val Lys Lys Pro Gly Glu Ser Leu Arg
530                 535                 540
Ile Ser Cys Lys Gly Ser Gly Phe Asn Ile Glu Asp Tyr Tyr Ile His
545                 550                 555                 560
Trp Val Arg Gln Met Pro Gly Lys Gly Leu Glu Trp Met Gly Arg Ile
            565                 570                 575
Asp Pro Glu Asn Asp Glu Thr Lys Tyr Gly Pro Ile Phe Gln Gly His
                580                 585                 590
Val Thr Ile Ser Ala Asp Thr Ser Ile Asn Thr Val Tyr Leu Gln Trp
            595                 600                 605
Ser Ser Leu Lys Ala Ser Asp Thr Ala Met Tyr Tyr Cys Ala Phe Arg
            610                 615                 620
Gly Gly Val Tyr Trp Gly Gln Gly Thr Thr Val Thr Val Ser Ser Gly
```

```
                625                 630                 635                 640
Gly Gly Gly Ser Gly Gly Gly Ser Gly Gly Gly Ser Gly Gly
                645                 650                 655
Gly Gly Ser Asp Val Val Met Thr Gln Ser Pro Asp Ser Leu Ala Val
                660                 665                 670
Ser Leu Gly Glu Arg Ala Thr Ile Asn Cys Lys Ser Ser Gln Ser Leu
            675                 680                 685
Leu Asp Ser Asp Gly Lys Thr Tyr Leu Asn Trp Leu Gln Gln Lys Pro
        690                 695                 700
Gly Gln Pro Pro Lys Arg Leu Ile Ser Leu Val Ser Lys Leu Asp Ser
705                 710                 715                 720
Gly Val Pro Asp Arg Phe Ser Gly Ser Gly Ser Gly Thr Asp Phe Thr
                725                 730                 735
Leu Thr Ile Ser Ser Leu Gln Ala Glu Asp Val Ala Val Tyr Tyr Cys
                740                 745                 750
Trp Gln Gly Thr His Phe Pro Gly Thr Phe Gly Gly Gly Thr Lys Val
                755                 760                 765
Glu Ile Lys Thr Thr Thr Pro Ala Pro Arg Pro Pro Thr Pro Ala Pro
        770                 775                 780
Thr Ile Ala Ser Gln Pro Leu Ser Leu Arg Pro Glu Ala Cys Arg Pro
785                 790                 795                 800
Ala Ala Gly Gly Ala Val His Thr Arg Gly Leu Asp Phe Ala Cys Asp
                805                 810                 815
Ile Tyr Ile Trp Ala Pro Leu Ala Gly Thr Cys Gly Val Leu Leu Leu
                820                 825                 830
Ser Leu Val Ile Thr Leu Tyr Cys Lys Arg Gly Arg Lys Lys Leu Leu
                835                 840                 845
Tyr Ile Phe Lys Gln Pro Phe Met Arg Pro Val Gln Thr Thr Gln Glu
                850                 855                 860
Glu Asp Gly Cys Ser Cys Arg Phe Pro Glu Glu Glu Glu Gly Gly Cys
865                 870                 875                 880
Glu Leu Arg Val Lys Phe Ser Arg Ser Ala Asp Ala Pro Ala Tyr Gln
                885                 890                 895
Gln Gly Gln Asn Gln Leu Tyr Asn Glu Leu Asn Leu Gly Arg Arg Glu
                900                 905                 910
Glu Tyr Asp Val Leu Asp Lys Arg Arg Gly Arg Asp Pro Glu Met Gly
            915                 920                 925
Gly Lys Pro Arg Arg Lys Asn Pro Gln Glu Gly Leu Tyr Asn Glu Leu
        930                 935                 940
Gln Lys Asp Lys Met Ala Glu Ala Tyr Ser Glu Ile Gly Met Lys Gly
945                 950                 955                 960
Glu Arg Arg Arg Gly Lys Gly His Asp Gly Leu Tyr Gln Gly Leu Ser
                965                 970                 975
Thr Ala Thr Lys Asp Thr Tyr Asp Ala Leu His Met Gln Ala Leu Pro
                980                 985                 990
Pro Arg

<210> SEQ ID NO 62
<211> LENGTH: 21
<212> TYPE: PRT
<213> ORGANISM: Artificial Sequence
<220> FEATURE:
<223> OTHER INFORMATION: Synthetic Construct

<400> SEQUENCE: 62
```

Met Glu Thr Asp Thr Leu Leu Leu Trp Val Leu Leu Leu Trp Val Pro
1               5                   10                  15

Gly Ser Thr Gly Asp
            20

<210> SEQ ID NO 63
<211> LENGTH: 250
<212> TYPE: PRT
<213> ORGANISM: Artificial Sequence
<220> FEATURE:
<223> OTHER INFORMATION: Synthetic Construct

<400> SEQUENCE: 63

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser
                245                 250

<210> SEQ ID NO 64
<211> LENGTH: 243
<212> TYPE: PRT
<213> ORGANISM: Artificial Sequence
<220> FEATURE:
<223> OTHER INFORMATION: Synthetic Construct

<400> SEQUENCE: 64

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr

Thr Met His Trp Val Lys Gln Arg Pro Gly Gln Gly Leu Glu Trp Ile
            20                  25                  30
            35                  40                  45

Gly Tyr Ile Asn Pro Ser Arg Gly Tyr Thr Asn Tyr Asn Gln Lys Phe
            50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 65
<211> LENGTH: 246
<212> TYPE: PRT
<213> ORGANISM: Artificial Sequence
<220> FEATURE:
<223> OTHER INFORMATION: Synthetic Construct

<400> SEQUENCE: 65

Glu Ile Gln Leu Val Gln Ser Gly Ala Glu Val Lys Lys Pro Gly Glu
 1               5                  10                  15

Ser Leu Arg Ile Ser Cys Lys Gly Ser Gly Phe Asn Ile Glu Asp Tyr
             20                  25                  30

Tyr Ile His Trp Val Arg Gln Met Pro Gly Lys Gly Leu Glu Trp Met
             35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
 65                  70                  75                  80

Leu Gln Trp Ser Ser Leu Lys Ala Ser Asp Thr Ala Met Tyr Tyr Cys
                 85                  90                  95

Ala Phe Arg Gly Gly Val Tyr Trp Gly Gln Gly Thr Thr Val Thr Val
                100                 105                 110

Ser Ser Gly Gly Gly Gly Ser Gly Gly Gly Ser Gly Gly Gly Gly
            115                 120                 125

Ser Gly Gly Gly Gly Ser Asp Val Val Met Thr Gln Ser Pro Asp Ser
    130                 135                 140

```
Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 66
<211> LENGTH: 69
<212> TYPE: PRT
<213> ORGANISM: Artificial Sequence
<220> FEATURE:
<223> OTHER INFORMATION: Synthetic Construct

<400> SEQUENCE: 66

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 67
<211> LENGTH: 42
<212> TYPE: PRT
<213> ORGANISM: Artificial Sequence
<220> FEATURE:
<223> OTHER INFORMATION: Synthetic Construct

<400> SEQUENCE: 67

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 68
<211> LENGTH: 112
<212> TYPE: PRT
<213> ORGANISM: Artificial Sequence
<220> FEATURE:
<223> OTHER INFORMATION: Synthetic Construct

<400> SEQUENCE: 68

Arg Val Lys Phe Ser Arg Ser Ala Asp Ala Pro Ala Tyr Gln Gln Gly
1               5                   10                  15
```

-continued

```
Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
             35                  40              45

Pro Arg Arg Lys Asn Pro Gln Glu Gly Leu Tyr Asn Glu Leu Gln Lys
             50                  55                  60

Asp Lys Met Ala Glu Ala Tyr Ser Glu Ile Gly Met Lys Gly Glu Arg
 65              70                      75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110
```

CHIMERIC ANTIGEN RECEPTOR T CELLS TARGETING THE TUMOR MICROENVIRONMENT

FEDERALLY SPONSORED RESEARCH

This invention was made with government support under CA166039 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Jun. 18, 2019, is named 51295-006003_Sequence_Listing_09.20.19_ST25 and is 127,795 bytes in size.

TECHNICAL FIELD

The technology described herein relates to immunotherapy.

BACKGROUND

Chimeric antigen receptor (CARs) provide a way to direct a cytotoxic T cell response to target cells expressing a selected target antigen, most often a tumor antigen or tumor-associated antigen. CARs are an adaptation of the T cell receptor, where the antigen binding domain is replaced with the antigen binding domain of an antibody that specifically binds the derived target antigen. Engagement of the target antigen on the surface of a target cell by a CAR expressed on a T cell ("CAR T cell" or "CAR-T") promotes killing of the target cell.

SUMMARY

The invention provides chimeric antigen receptor (CAR) T cells including a heterologous nucleic acid molecule, wherein the heterologous nucleic acid molecule includes: (a) a first polynucleotide encoding a CAR including an antigen-binding domain, a transmembrane domain, and an intracellular signaling domain; and (b) a second polynucleotide encoding a therapeutic agent. Optionally, the first and second polynucleotides are included within a single polynucleotide molecule. Furthermore, in some embodiments, the CAR further includes one or more co-stimulatory domains (e.g., 4-1BB; also see below).

In various embodiments, the therapeutic agent is or includes an antibody reagent (e.g., a single chain antibody, a single domain antibody (e.g., a camelid antibody), or a bispecific antibody reagent (e.g., a bispecific T cell engager (BiTE); also see below). In other embodiments, the therapeutic agent is or includes a cytokine.

In various embodiments, the CAR and the therapeutic agent are produced in the form of a polyprotein (and thus may be encoded within a single nucleic acid molecule), which is cleaved to generate separate CAR and therapeutic agent molecules. In some embodiments, the polyprotein includes a cleavable moiety (e.g., a 2A peptide, such as P2A or T2A; also see below) between the CAR and the therapeutic agent. In some embodiments, the CAR and the therapeutic agent are each constitutively expressed. In some embodiments, expression of the CAR and the therapeutic agent is driven by an elongation factor-1 alpha (EF1α) promoter. In some embodiments, the therapeutic agent is expressed under the control of an inducible promoter (e.g., the NFAT promoter), which is optionally inducible by T cell receptor or CAR signaling. In some embodiments, the CAR is expressed under the control of a constitutive promoter and the therapeutic agent is expressed under the control of an inducible promoter (e.g., the NFAT promoter), which is optionally inducible by T cell receptor or CAR signaling.

In various embodiments, the antigen-binding domain of the CAR is or includes an antibody, a single chain antibody, a single domain antibody (e.g., a camelid antibody), or a ligand.

In various embodiments, the transmembrane domain of the CAR includes a CD8 hinge/transmembrane domain, which optionally includes the sequence of any one of SEQ ID NOs: 4, 10, 16, 22, 28, 37, 46, 58, and 66, or a variant thereof.

In various embodiments, the intracellular signaling domain includes a CD3 intracellular signaling domain, which optionally includes or consists of the sequence of any one of SEQ ID NOs: 6, 12, 18, 24, 30, 39, 48, 60, and 68, or a variant thereof.

In various embodiments, a 4-1BB co-stimulatory domain is included, which optionally includes or consists of the sequence of any one of SEQ ID NOs: 5, 11, 17, 23, 29, 38, 47, 59, and 67, or a variant thereof.

In various embodiments, the CAR antigen-binding domain or the therapeutic agent, when the therapeutic agent is or includes an antibody reagent, bind to a tumor-associated antigen (see, e.g., below). In various embodiments, the tumor-associated antigen to which the CAR antigen-binding domain or the therapeutic agent binds is a solid tumor-associated antigen. In various embodiments, the tumor-associated antigen to which the CAR antigen-binding domain or the therapeutic agent binds includes epidermal growth factor receptor variant III (EGFRvIII), EGFR, CD19, prostate-specific membrane antigen (PSMA), or IL-13 receptor alpha 2 (IL-13Rα2), and optionally the CAR antigen-binding domain or the therapeutic agent includes a sequence selected from the group consisting of SEQ ID NO: 21, 27, 33, 36, 42, 45, 51, 55, 57, 63, 65, and variants thereof.

In various embodiments, the CAR antigen-binding domain or the therapeutic agent, when the therapeutic agent is or includes an antibody reagent, binds to a Treg-associated antigen. In various embodiments, the Treg-associated antigen to which the CAR antigen-binding domain or the therapeutic agent binds is selected from the group consisting of glycoprotein A repetitions predominant (GARP), latency-associated peptide (LAP), CD25, and cytotoxic T lymphocyte-associated antigen-4 (CTLA-4), and optionally the CAR antigen-binding domain or the therapeutic agent includes a sequence selected from the group consisting of SEQ ID NO: 3, 9, 15, 25, and variants thereof.

The invention further provides CAR T cells including a polynucleotide encoding a CAR, wherein the CAR includes an antigen-binding domain, a transmembrane domain (e.g., CD8 hinge/TM; see, e.g., below for additional examples), and an intracellular signaling domain (e.g., CD3z; see, e.g., below for additional examples); and the antigen-binding domain binds to a Treg-associated antigen. In various embodiments, the Treg-associated antigen is selected from the group consisting of GARP, LAP, CD25, and CTLA-4. In various embodiments, the CAR further includes one or more co-stimulatory domains (e.g., 4-1BB; see, e.g., below for additional examples). In various examples, the antigen-binding domain of the CAR includes a scFv or a single domain antibody, which optionally includes a sequence selected from the group consisting of SEQ ID NO: 3, 9, 15, 25, and variants thereof.

The invention further provides CAR T cells including a heterologous nucleic acid molecule encoding an amino acid sequence having at least 90% (e.g., at least 91%, 92%, 93%, 94%, 95%, 96%, 97%, 98%, or 99%, or 100%) sequence identity to the amino acid sequence of any one of SEQ ID NO: 26, SEQ ID NO: 35, SEQ ID NO: 44, SEQ ID NO: 53, SEQ ID NO: 61, SEQ ID NO: 19, SEQ ID NO: 1, SEQ ID NO: 7, and SEQ ID NO: 13.

Further, the invention provides nucleic acid molecules encoding (i) CAR polypeptides or (ii) polyproteins including a CAR polypeptide and a therapeutic agent, as described herein.

The invention additional provides (i) CAR polypeptides or (ii) polyproteins including a CAR polypeptide and a therapeutic agent, as described herein.

The invention additional provides pharmaceutical compositions including one or more CAR T cells, nucleic acid molecules, CAR polypeptides, or a polyproteins as described herein.

Also included in the invention are methods of treating subject, including patients (e.g., human patients) having a disease or condition (e.g., cancer (such as glioblastoma); also see below). The methods include administering to the subject a pharmaceutical composition including one or more CAR T cells or pharmaceutical compositions described herein. In various embodiments, the methods target the tumor microenvironment, by which, e.g., systemic toxicity is reduced. In various embodiments, the cancer is characterized by the presence of one or more solid tumors. In various embodiments, the cancer is characterized by tumor-infiltrating Tregs.

The invention further provides methods of treating a subject (e.g., a patient, such as a human patient) having cancer. The methods include administering to the subject a CAR T cell product, genetically modified to secrete a tumor-toxic antibody or cytokine, wherein by directing the cancer toxicity locally to the tumor microenvironment, systemic toxicity is reduced. In various embodiments, the CAR T cell is genetically modified to deliver an antibody against CTLA4, CD25, GARP, LAP, IL15, CSF1R, or EGFR, or a bispecific antibody (directed against, e.g., EGFR and CD3) against to the tumor microenvironment.

The invention additionally provides methods of delivering one or more therapeutic agents to a tissue or organ in a patient to treat a disease or pathology. The methods include administering to the patient a CAR T cell, genetically modified to secrete a therapeutic antibody, toxin, or agent, wherein the therapeutic antibody, toxin, or agent would, by itself, be unable to enter or penetrate the tissue or organ.

In various embodiments, the tissue or organ is in the nervous system. In various embodiments, the nervous system is the central nervous system (e.g., brain). In various embodiments, the disease or pathology is glioblastoma. In various embodiments, the therapeutic antibody is anti-EGFR (anti-epidermal growth factor receptor) or anti-EGFRvIII.

The invention also includes use of the CAR T cells, polypeptides, nucleic acid molecules, pharmaceutical compositions, and other compositions and molecules in the use of preventing or treating a disease or condition described herein, or in the use of the preparation of a medicament therefor.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of each of which are all incorporated by reference herein in their entireties.

The terms "decrease," "reduced," "reduction," or "inhibit" are all used herein to mean a decrease by a statistically significant amount. In some embodiments, "reduce," "reduction," or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

The terms "increased," "increase," "enhance," or "activate" are all used herein to mean an increase by a statically significant amount. In some embodiments, the terms "increased," "increase," "enhance," or "activate" can mean an increase of at least 10% as compared to a reference level, for example, an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient," and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease, e.g., cancer. A subject can be male or female.

A subject can be one who has been previously diagnosed with or identified as suffering from or having a condition in need of treatment (e.g., glioblastoma, glioma, leukemia, or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

A "disease" is a state of health of an animal, for example, a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "tumor antigen" and "cancer antigen" are used interchangeably to refer to antigens that are differentially expressed by cancer cells and can thereby be exploited in order to target cancer cells. Cancer antigens are antigens that can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively. Examples of tumor antigens are provided below and include, e.g., EGFR, EGFRvIII, CD19, PSMA, BCMA, IL13Ra2, etc.

As used herein, "Treg antigen" or "Treg-associated antigen" are used interchangeably to refer to antigens that are expressed by T regulatory (Treg) cells. These antigens may optionally be targeted by the cells and methods of the invention. Examples of Treg antigens are provided below and include, e.g., GARP, LAP, CD25, and CTLA4.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules.

By "bi-specific T cell engagers," "BiTE antibody constructs," or BiTEs" is meant polypeptides that each include tandemly linked single-chain variable fragments (scFvs). Optionally, the scFvs are linked by a linker (e.g., a glycine-rich linker). One scFv of the BiTE binds to the T cell receptor (TCR) (e.g., to the CD& subunit) and the other binds to a target antigen (e.g., a tumor-associated antigen).

In some embodiments, "activation" can refer to the state of a T cell that has been sufficiently stimulated to induce detectable cellular proliferation. In some embodiments activation can refer to induced cytokine production. In some embodiments, activation can refer to detectable effector functions. At a minimum, an "activated T cell" as used herein is a proliferative T cell.

As used herein, the terms "specific binding" and "specifically binds" refer to a physical interaction between two molecules, compounds, cells and/or particles wherein the first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more greater than the affinity for the third non-target entity under the same conditions. A reagent specific for a given target is one that exhibits specific binding for that target under the conditions of the assay being utilized. A non-limiting example includes an antibody, or a ligand, which recognizes and binds with a cognate binding partner (for example, a stimulatory and/or costimulatory molecule present on a T cell) protein.

A "stimulatory ligand," as used herein, refers to a ligand that when present on an antigen presenting cell (APC, e.g., a macrophage, a dendritic cell, a B-cell, an artificial APC, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell.

"Co-stimulatory ligand," as the term is used herein, includes a molecule on an APC that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1BB, OX40, CD30, CD40, PD-1, ICOS, lymphocyte function-associated antigen-1 (LFA-1), CD2, CD7, LIGHT, NKG2C, B7-H3, and CD83.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide that retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions, or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g., a CAR polypeptide) is comprised by a vector. In some of the aspects described herein, a nucleic acid sequence encoding a given polypeptide as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example, in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3'

UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down, or stop the progression or severity of a condition associated with a disease or disorder, e.g., glioblastoma, glioma, acute lymphoblastic leukemia or other cancer, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

As used herein, the term "administering," refers to the placement of a therapeutic or pharmaceutical composition as disclosed herein into a subject by a method or route that results in at least partial delivery of the agent at a desired site. Pharmaceutical compositions comprising agents as disclosed herein can be administered by any appropriate route that results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined within the description of the various aspects and embodiments of the technology, as set forth below.

The invention provide several advantages. For example, the CAR T cells of the invention can be used to deliver therapeutic molecules for cancer treatment. In one example, the CAR T cells of the invention can be used to deliver otherwise toxic antibodies (e.g., anti-CTLA4 or anti-CD25 (e.g., daclizumab) or other molecules (e.g., cytokines) to the tumor microenvironment, where they can advantageously enable activation of surrounding tumor infiltrating lymphocytes, provide checkpoint blockade, and deplete regulatory T cells (Tregs). The CAR T cells of the invention can further be directed against Treg antigens, to facilitate targeting of Treg cells. Furthermore, certain CAR T cells of the invention can be used to deliver genetically encoded molecules (e.g., antibodies or cytokines) to regions of the body (e.g., the central nervous system, including the brain) that these molecules otherwise cannot reach. In one example, CAR T cells targeting EGFRvIII can be used to target brain tumors, and can deliver antibodies (e.g., antibodies against EGFR, such as cetuximab; also see below) to the tumors. The invention thus provides genetically-encoded Treg targeting in the tumor microenvironment. In addition, the invention provides genetically-encoded delivery of antibodies that cannot get into certain tissues, and could enhance the potency of T cell therapies by broadening the specificity of the anti-tumor target. The invention accordingly provides for gene-modified T cell therapy for cancer.

Other features and advantages of the invention will be apparent from the following detailed description, the drawings, and the claims.

BRIEF DESCRIPTION OF THE DRAWINGS

FIG. 2A shows mice treated with untransduced cells as a negative control. FIG. 2B shows mice treated with CART-EGFRvIII on day 4 after implantation (top row), with successful treatment by day 21 (bottom row).

FIG. 2A shows mice treated with untransduced (UTD) cells as a negative control at day 5 (D5; top) and D11 (bottom). FIG. 2B shows mice treated with CART-EGFRvIII on day 2 after implantation at D5 (top row) and at D21 (bottom row).

FIG. 4A shows T cells stained for CD3. FIG. 4B shows CD25+ cells. CD25 is the IL-2 receptor alpha chain, a marker of activated or regulatory T cells.

FIGS. 5A-5C are fluorescence micrographs qualitatively demonstrating Treg suppression of CAR T cell (red) antitumor activity after 18 hours of coincubation with human glioma cells (green) in vitro. FIG. 5A shows relative concentration of CART-nonspecific cells to glioma cells. FIG. 5B shows relative concentration of CART-EGFRvIII cells to glioma cells with no Tregs in the culture. FIG. 5C shows relative concentration of CART-EGFRvIII cells to glioma cells with Tregs included in the culture.

FIG. 5D is a graph showing quantitative readouts of green object confluence as a measure of glioma cell viability as a function of time (up to 48 hours). The top line represents the results shown in FIG. 5A (glioma cell growth), the bottom line represents the results shown in FIG. 5B (glioma cell killing), and the middle line represents the results shown in FIG. 5C (glioma cell resistance to CART-killing).

FIG. 8A shows a LAP-targeting CAR construct having an anti-LAP scFv with its light chain (L) and heavy chain (H) arranged in a 5'-to-3' direction, respectively (CART-LAP-L-H). FIG. 8B shows a LAP-targeting CAR construct having an anti-LAP scFv with its heavy chain (H) and light chain (L) arranged in a 5'-to-3' direction, respectively (CART-LAP-H-L). FIG. 8C shows a GARP-targeting CAR construct having an anti-GARP camelid antibody binding domain (CART-GARP). FIG. 8D shows an EGFR-targeted CAR construct having an anti-GARP camelid antibody.

FIG. 9A shows killing of activated Tregs, and FIG. 9B shows killing of non-activated Tregs. CART-LAP-H-L was more effective at killing non-activated Tregs in comparison to CART-LAP-L-H.

FIGS. 10A and 10B show results from the same experiment conducted in two different donors.

FIGS. 11A and 11B show number of target cells remaining in coculture as measured by flow cytometry. A dashed line indicates the number of target cells in a control sample containing no CAR cells. FIG. 11A shows non-activated Tregs as target cells, whereas FIG. 11B shows activated Tregs as target cells. FIGS. 11C and 11D show percent cytotoxicity as measured by luciferase expression by target cells. FIG. 11C shows non-activated Tregs as target cells, whereas FIG. 11D shows activated Tregs as target cells. In each of 11A-11D, circles represent CART-LAP-H-L, squares represent CART-LAP-L-H, and triangles represent untransduced CAR cells.

FIG. 13A shows the number of target cells remaining in culture after three days, as measured by flow cytometry. A dashed line indicates the number of target cells in a control sample containing no CAR cells. FIG. 13B shows percent cytotoxicity as measured by luciferase expression by target cells. Circles represent CART-LAP-H-L, squares represent CART-LAP-L-H, and triangles represent untransduced CAR cells.

FIGS. 16A and 16B show the full gel, including molecular weight reference ladders. FIG. 16C is a longer exposure of the bottom region of the gel shown in FIG. 16B, in which a band between 10 and 15 kD is identified with an arrow, indicating the presence of a camelid antibody.

DETAILED DESCRIPTION

Figure 1:
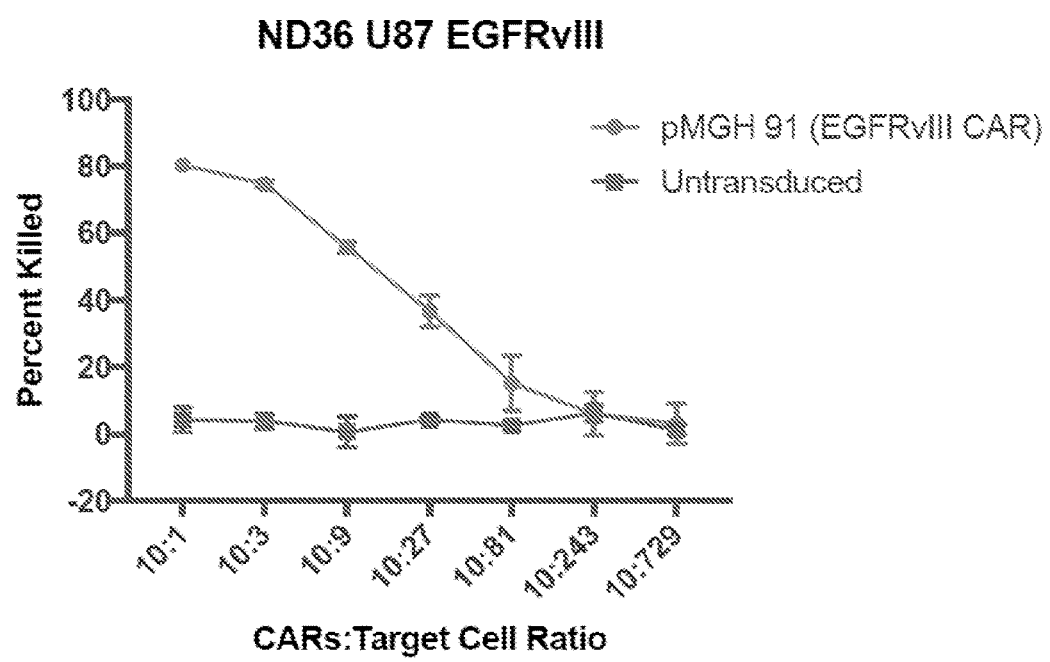
FIG. 1 is a graph showing killing of human glioma target cell line U87vIII by CART-EGFRvIII cells as a function of CART-EGFRvIII:U87vIII target cell ratio. Untransduced cells were incubated with target cells as a negative control.

The invention provides improved approaches to chimeric antigen receptor T cell ("CAR T cell")-based therapy. In general, the improvements relate to different aspects of targeting in antitumor therapy, for example, targeting of the tumor microenvironment.

As is explained further below, we have demonstrated that regulatory T cells (also referred to herein as "Tregs"), which play a role in the suppression of a subject's immune response against tumors (e.g., in the tumor microenvironment), can be targeted with CAR T cells. The invention thus provides CAR T cells, in which the CAR is directed against a Treg antigen or marker (e.g., GARP, LAP, CTLA4, or CD25; also see below). In other examples, the invention provides CAR T cells that secrete antibodies (e.g., single chain antibodies, single domain antibodies (e.g., camelid antibodies), or bispecific antibodies (e.g., bispecific T cell engagers)) against one or more Treg antigens or markers (e.g., GARP, LAP, CTLA4 and CD25; also see below). In addition to targeting Tregs, the invention provides CAR T cells and related methods for delivering other therapeutic agents (e.g., antibodies and related molecules) to tumors. In one example, a CAR T cell having a CAR specific for EGFRvIII is used to target brain tumors (e.g., glioblastomas). Such CAR T cells may also be used to deliver therapeutic molecules, such as antibody reagents (e.g., single chain antibodies, single domain antibodies (e.g., camelid antibodies), or bi-specific antibodies (e.g., bispecific T cell engagers)) to these tumors. These methods are particularly advantageous, as they, in effect, facilitate antibody administration to the brain, despite the blood brain barrier through which antibodies do not normally pass. These approaches, as well as related methods and compositions, are described further, as follows.

Chimeric Antigen Receptors

The technology described herein provides improved CARs for use in immunotherapy. The following discusses CARs and the various improvements.

The terms "chimeric antigen receptor" or "CAR" or "CARs" as used herein refer to engineered T cell receptors, which graft a ligand or antigen specificity onto T cells (for example, naïve T cells, central memory T cells, effector memory T cells or combinations thereof). CARs are also known as artificial T-cell receptors, chimeric T-cell receptors or chimeric immunoreceptors.

A CAR places a chimeric extracellular target-binding domain that specifically binds a target, e.g., a polypeptide, expressed on the surface of a cell to be targeted for a T cell response onto a construct including a transmembrane domain and intracellular domain(s) of a T cell receptor molecule. In one embodiment, the chimeric extracellular target-binding domain comprises the antigen-binding domain(s) of an antibody that specifically binds an antigen expressed on a cell to be targeted for a T cell response. The properties of the intracellular signaling domain(s) of the CAR can vary as known in the art and as disclosed herein, but the chimeric target/antigen-binding domains(s) render the receptor sensitive to signaling activation when the chimeric target/antigen binding domain binds the target/antigen on the surface of a targeted cell.

With respect to intracellular signaling domains, so-called "first-generation" CARs include those that solely provide CD3zeta (CD3ζ) signals upon antigen binding. So-called "second-generation" CARs include those that provide both co-stimulation (e.g., CD28 or CD 137) and activation (CD3) domains, and so-called "third-generation" CARs include those that provide multiple costimulatory (e.g., CD28 and CD 137) domains and activation domains (e.g., CD3). In various embodiments, the CAR is selected to have high affinity or avidity for the target/antigen—for example, antibody-derived target or antigen binding domains will generally have higher affinity and/or avidity for the target antigen than would a naturally-occurring T cell receptor. This property, combined with the high specificity one can select for an antibody provides highly specific T cell targeting by CAR T cells.

As used herein, a "CAR T cell" or "CAR-T" refers to a T cell that expresses a CAR. When expressed in a T cell, CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

As used herein, the term "extracellular target binding domain" refers to a polypeptide found on the outside of the cell that is sufficient to facilitate binding to a target. The extracellular target binding domain will specifically bind to its binding partner, i.e., the target. As non-limiting examples, the extracellular target-binding domain can include an antigen-binding domain of an antibody or antibody reagent, or a ligand, which recognizes and binds with a cognate binding partner protein. In this context, a ligand is a molecule that binds specifically to a portion of a protein and/or receptor. The cognate binding partner of a ligand useful in the methods and compositions described herein can generally be found on the surface of a cell. Ligand:cognate partner binding can result in the alteration of the ligand-bearing receptor, or activate a physiological response, for example, the activation of a signaling pathway. In one embodiment, the ligand can be non-native to the genome. Optionally, the ligand has a conserved function across at least two species.

Antibody Reagents

In various embodiments, the CARs described herein comprise an antibody reagent or an antigen-binding domain thereof as an extracellular target-binding domain.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g., de Wildt et al., Eur. J. Immunol. 26(3):629-639, 1996; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like. Fully human antibody binding domains can be selected, for example, from phage display libraries using methods known to those of ordinary skill in the art. Furthermore, antibody reagents include single domain antibodies, such as camelid antibodies.

The $V_H$ and $V_L$ regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A. et al. (1991) Sequences of Proteins of Immunological Interest, Fifth Edition, U.S. Department of Health and Human Services, NIH Publication No. 91-3242, and Chothia et al., J. Mol. Biol. 196:901-917, 1987; each of which is incorporated by reference herein in its entirety). Each $V_H$ and $V_L$ is typically composed of three CDRs and four FRs, arranged from amino-terminus to carboxy-terminus in the following order: FR1, CDR1, FR2, CDR2, FR3, CDR3, FR4.

In one embodiment, the antibody or antibody reagent is not a human antibody or antibody reagent (i.e., the antibody or antibody reagent is mouse), but has been humanized. A "humanized antibody or antibody reagent" refers to a non-human antibody or antibody reagent that has been modified at the protein sequence level to increase its similarity to antibody or antibody reagent variants produced naturally in humans. One approach to humanizing antibodies employs the grafting of murine or other non-human CDRs onto human antibody frameworks.

In one embodiment, the extracellular target binding domain of a CAR comprises or consists essentially of a single-chain Fv (scFv) fragment created by fusing the $V_H$ and $V_L$ domains of an antibody, generally a monoclonal antibody, via a flexible linker peptide. In various embodiments, the scFv is fused to a transmembrane domain and to a T cell receptor intracellular signaling domain, e.g., an engineered intracellular signaling domain as described herein. In another embodiment, the extracellular target binding domain of a CAR comprises a camelid antibody.

Antibody binding domains and ways to select and clone them are well-known to those of ordinary skill in the art. In one embodiment, the antibody reagent is an anti-GARP antibody reagent and comprises the sequence of SEQ ID NO: 3 or 25, or comprises a sequence with at least 75%, at least 80%, at least 85%, at least 90%, at least 95%, at least 96%, at least 97%, at least 98%, at least 99%, or greater sequence identity to the sequence of SEQ ID NO: 3 or 25. In another embodiment, the antibody reagent is an anti-LAP antibody reagent and comprises the sequence of SEQ ID NO: 9 or 15, or comprises a sequence with at least 75%, at least 80%, at least 85%, at least 90%, at least 95%, at least 96%, at least 97%, at least 98%, at least 99%, or greater sequence identity to the sequence of SEQ ID NO: 9 or 15. In another embodiment, the antibody reagent is an anti-EGFR or anti-EGFRvIII antibody reagent and comprises the sequence of SEQ ID NO: 21, 27, 33, 36, 42, 45, 55, 57, or 65, or comprises a sequence with at least 75%, at least 80%, at least 85%, at least 90%, at least 95%, at least 96%, at least 97%, at least 98%, at least 99%, or greater sequence identity to the sequence of SEQ ID NO: 21, 27, 33, 36, 42, 45, 55, 57, or 65. In another embodiment, the antibody reagent is an anti-CD19 antibody reagent and comprises the sequence of SEQ ID NO: 51 or 63, or comprises a sequence with at least 75%, at least 80%, at least 85%, at least 90%, at least 95%, at least 96%, at least 97%, at least 98%, at least 99%, or greater sequence identity to the sequence of SEQ ID NO: 51 or 63. In another embodiment, the antibody reagent is an anti-CD3 antibody reagent and comprises the sequence of SEQ ID NO: 34, 43, 52, 56, or 64, or comprises a sequence with at least 75%, at least 80%, at least 85%, at least 90%, at least 95%, at least 96%, at least 97%, at least 98%, at least 99%, or greater sequence identity to the sequence of SEQ ID NO: 34, 43, 52, 56, or 64. In various examples, the antibody can be selected from C225, 3C10, Cetuximab, and 2173.

In one embodiment, the CARs useful in the technology described herein comprise at least two antigen-specific targeting regions, an extracellular domain, a transmembrane domain, and an intracellular signaling domain. In such embodiments, the two or more antigen-specific targeting regions target at least two different antigens and may be arranged in tandem and separated by linker sequences. In another embodiment, the CAR is a bispecific CAR. A bispecific CAR is specific to two different antigens.

Target/Antigen

Any cell-surface moiety can be targeted by a CAR. Often, the target will be a cell-surface polypeptide that may be differentially or preferentially expressed on a cell that one wishes to target for a T cell response. To target Tregs, antibody reagents can be targeted against, e.g., Glycoprotein A Repetitions Predominant (GARP), latency-associated peptide (LAP), CD25, CTLA-4, ICOS, TNFR2, GITR, OX40, 4-1BB, and LAG-3. To target tumors or cancer cells, antibody domains can be targeted against, e.g., EGFR or EGFRvIII, as described herein. Targeting tumor antigens or tumor-associated antigens that are specific to the tumors can provide a means to target tumor cells while avoiding or at least limiting collateral damage to non-tumor cells or tissues. Non-limiting examples of additional tumor antigens, tumor-associated antigens, or other antigen of interest include CD19, CD37, BCMA (tumor necrosis factor receptor superfamily member 17 (TNFRSF17); NCBI Gene ID: 608; NCBI Ref Seq NP_001183.2) and mRNA (e.g., NCBI Ref Seq NM_001192.2), CEA, immature laminin receptor, TAG-72, HPV E6 and E7, BING-4, calcium-activated chloride channel 2, cyclin B1, 9D7, Ep-CAM, EphA3, her2/neu, telomerase, mesotheliun, SAP-1, survivin, BAGE family, CAGE family, GAGE family, MAGE family, SAGE family, XAGE family, NY-ESO-1/LAGE-1, PRAME, SSX-2, Melan-A/MART-1, gp100/pmel17, tyrosinase, TRP-1/-2, MC1R, BRCA1/2, CDK4, MART-2, p53, Ras, MUC1, TGF-βRII, IL-15, IL13Ra2, and CSF1R.

Transmembrane Domain

Each CAR as described herein includes a transmembrane domain that joins the extracellular target-binding domain to the intracellular signaling domain.

As used herein, "transmembrane domain" (TM domain) refers to the generally hydrophobic region of the CAR which crosses the plasma membrane of a cell. The TM domain can be the transmembrane region or fragment thereof of a transmembrane protein (for example a Type I transmembrane protein or other transmembrane protein), an artificial hydrophobic sequence, or a combination thereof. While specific examples are provided herein and used in the Examples, other transmembrane domains will be apparent to those of skill in the art and can be used in connection with alternate embodiments of the technology. A selected transmembrane region or fragment thereof would preferably not interfere with the intended function of the CAR. As used in relation to a transmembrane domain of a protein or polypeptide, "fragment thereof" refers to a portion of a transmembrane domain that is sufficient to anchor or attach a protein to a cell surface.

In one embodiment, the transmembrane domain of a CAR or fragment thereof is derived from or comprises the transmembrane domain of CD8 (e.g., any one of SEQ ID NOs: 4, 10, 16, 22, 28, 37, 46, 58, or 66, or variants thereof). In an alternate embodiment, the transmembrane domain or fragment thereof of the CAR described herein comprises a transmembrane domain selected from the transmembrane domain of an alpha, beta or zeta chain of a T-cell receptor, CD28, CD3 epsilon, CD45, CD4, CDS, CD8, CD9, CD16, CD22, CD33, CD37, CD64, CD80, CD86, CD134, CD137, CD154, KIRDS2, OX40, CD2, CD27, LFA-1 (CDI 1a, CD18), ICOS (CD278), 4-1BB (CD137), 4-1BBL, GITR, CD40, BAFFR, HVEM (LIGHTR), SLAMF7, NKp80 (KLRFI), CD160, CD19, IL2R beta, IL2R gamma, IL7R a, ITGA1, VLA1, CD49a, ITGA4, IA4, CD49D, ITGA6, VLA-6, CD49f, ITGAD, CDI 1d, ITGAE, CD103, ITGAL, CDI 1a, LFA-1, ITGAM, CDI 1b, ITGAX, CDI 1c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

CD8 is an antigen preferentially found on the cell surface of cytotoxic T lymphocytes. CD8 mediates cell-cell interactions within the immune system, and acts as a T cell co-receptor. CD8 consists of an alpha (CD8α) and beta (CD8β) chain. CD8a sequences are known for a number of species, e.g., human CD8a, (NCBI Gene ID: 925) polypeptide (e.g., NCBI Ref Seq NP_001139345.1) and mRNA (e.g., NCBI Ref Seq NM_000002.12). CD8 can refer to human CD8, including naturally occurring variants, molecules, and alleles thereof. In some embodiments of any of the aspects, e.g., in veterinary applications, CD8 can refer to the CD8 of, e.g., dog, cat, cow, horse, pig, and the like. Homologs and/or orthologs of human CD8 are readily identified for such species by one of skill in the art, e.g., using the NCBI ortholog search function or searching available sequence data for a given species for sequence similar to a reference CD8 sequence.

4-1BBL is a type 2 transmembrane glycoprotein belonging to the TNF superfamily. 4-1 BBL is expressed on activated T lymphocytes. 4-1BBL sequences are known for a number of species, e.g., human 4-1BBL, also known as TNFSF9 (NCBI Gene ID: 8744) polypeptide (e.g., NCBI Ref Seq NP_003802.1) and mRNA (e.g., NCBI Ref Seq NM_003811.3). 4-1BBL can refer to human 4-1BBL, including naturally occurring variants, molecules, and alleles thereof. In some embodiments of any of the aspects, e.g., in veterinary applications, 4-1BBL can refer to the 4-1 BBL of, e.g., dog, cat, cow, horse, pig, and the like. Homologs and/or orthologs of human 4-1BBL are readily identified for such species by one of skill in the art, e.g., using the NCBI ortholog search function or searching available sequence data for a given species for sequence similar to a reference 4-1BBL sequence.

Co-Stimulatory Domain

Each CAR described herein optionally comprises the intracellular domain of one or more co-stimulatory molecule or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. In one example, a 4-1BB intracellular domain (ICD) can be used (see, e.g., below and SEQ ID NOs: 5, 11, 17, 23, 29, 38, 47, 59, 67, or variants thereof).

Additional illustrative examples of such co-stimulatory molecules include CARD11, CD2, CD7, CD27, CD28, CD30, CD40, CD54 (ICAM), CD83, CD134 (0X40), CD137 (4-1BB), CD150 (SLAMF1), CD152 (CTLA4), CD223 (LAGS), CD270 (HVEM), CD273 (PD-L2), CD274 (PD-L1), CD278 (ICOS), DAP10, LAT, NKD2C SLP76, TRIM, and ZAP70. In one embodiment, the intracellular domain is the intracellular domain of 4-1BB. 4-1BB (CD137; TNFRS9) is an activation-induced costimulatory molecule, and is an important regulator of immune responses.

Intracellular Signaling Domain

CARs as described herein comprise an intracellular signaling domain. An "intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain. In various examples, the intracellular signaling domain is from CD3ζ (see, e.g., below and SEQ ID NOs: 6, 12, 18, 24, 30, 39, 48, 60, 68, or variants thereof). Additional non-limiting examples of ITAM-containing intracellular signaling domains that are of particular use in the technology include those derived from TCRζ, FcRγ, FcRβ, CD3γ, CD3θ, CD3δ, CD3ε, CD3ζ, CD22, CD79a, CD79b, and CD66d.

CD3 is a T cell co-receptor that facilitates T lymphocyte activation when simultaneously engaged with the appropriate co-stimulation (e.g., binding of a co-stimulatory molecule). A CD3 complex consists of 4 distinct chains; mammal CD3 consists of a CD3γ chain, a CD3δ chain, and two CD3ε chains. These chains associate with a molecule known as the T cell receptor (TCR) and the CD3ζ to generate an activation signal in T lymphocytes. A complete TCR complex comprises a TCR, CD3λ, and the complete CD3 complex.

In some embodiments of any aspect, a CAR polypeptide described herein comprises an intracellular signaling domain that comprises an Immunoreceptor Tyrosine-based Activation Motif or ITAM from CD3 zeta (CD3ζ). In some embodiments of any aspect, the ITAM comprises three motifs of ITAM of CD3ζ (ITAM3). In some embodiments of any aspect, the three motifs of ITAM of CD3ζ are not mutated and, therefore, include native or wild-type sequences. In some embodiments, the CD3ζ sequence comprises the sequence of a CD3ζ as set forth in the sequences provided herein.

Individual CAR and other construct components as described herein can be used with one another and swapped in and out of various constructs described herein, as can be determined by those of skill in the art. Each of these components can comprise or consist of any of the corresponding sequences set forth herein, or variants thereof.

A more detailed description of CARs and CAR T cells can be found in Maus et al., Blood 123:2624-2635, 2014; Reardon et al., Neuro-Oncology 16:1441-1458, 2014; Hoyos et al., Haematologica 97:1622, 2012; Byrd et al., J. Clin. Oncol. 32:3039-3047, 2014; Maher et al., Cancer Res 69:4559-4562, 2009; and Tamada et al., Clin. Cancer Res. 18:6436-6445, 2012; each of which is incorporated by reference herein in its entirety.

In one embodiment, the CAR further comprises a linker domain. As used herein "linker domain" refers to an oligo- or polypeptide region from about 2 to 100 amino acids in length, which links together any of the domains/regions of the CAR as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In various examples, linkers having sequences as set forth herein, or variants thereof, are used. It is to be understood that the indication of a particular linker in a construct in a particular location does not mean that only that linker can be used there. Rather, different linker sequences (e.g., P2A and T2A) can be swapped with one another (e.g., in the context of the constructs of the present invention), as can be determined by those of skill in the art. In one embodiment, the linker region is T2A derived from Thosea asigna virus. Non-limiting examples of linkers that can be used in this technology include T2A, P2A, E2A, BmCPV2A, and BmIFV2A. Linkers such as these can be used in the context of polyproteins, such as those described below. For example, they can be used to separate a CAR component of a polyprotein from a therapeutic agent (e.g., an antibody, such as a scFv, single domain antibody (e.g., a camelid antibody), or a bispecific antibody (e.g., a BiTE)) component of a polyprotein (see below).

In some embodiments, a CAR as described herein optionally further comprises a reporter molecule, e.g., to permit for non-invasive imaging (e.g., positron-emission tomography PET scan). In a bispecific CAR that includes a reporter molecule, the first extracellular binding domain and the second extracellular binding domain can include different or the same reporter molecule. In a bispecific CAR T cell, the first CAR and the second CAR can express different or the same reporter molecule. In another embodiment, a CAR as described herein further comprises a reporter molecule (for example hygromycin phosphotransferase (hph)) that can be imaged alone or in combination with a substrate or chemical (for example 9-[4-[$^{18}$F]fluoro-3-(hydroxymethyl)butyl]guanine ([$^{18}$F]FHBG)). In another embodiment, a CAR as described herein further comprises nanoparticles at can be readily imaged using non-invasive techniques (e.g., gold nanoparticles (GNP) functionalized with $^{64}Cu^{2+}$). Labeling of CAR T cells for non-invasive imaging is reviewed, for example in Bhatnagar et al., Integr. Biol. (Camb). 5(1):231-238, 2013, and Keu et al., Sci. Transl. Med. 18; 9(373), 2017, which are incorporated herein by reference in their entireties.

GFP and mCherry are demonstrated herein as fluorescent tags useful for imaging a CAR expressed on a T cell (e.g., a CAR T cell). It is expected that essentially any fluorescent protein known in the art can be used as a fluorescent tag for this purpose. For clinical applications, the CAR need not include a fluorescent tag or fluorescent protein. In each instance of particular constructs provided herein, therefore, any markers present in the constructs can be removed. The invention includes the constructs with or without the markers. Accordingly, when a specific construct is referenced herein, it can be considered with or without any markers or tags (including, e.g., histidine tags) as being included within the invention.

In one embodiment, the CAR polypeptide sequence corresponds to, comprises, or comprises a sequence with at least 80%, at least 85%, at least 90%, at least 91%, at least 92%, at least 93%, at least 94%, at least 95%, at least 96%, at least 97%, at least 98%, at least 99% or greater sequence identity of a sequence selected from SEQ ID NOs: 1, 7, or 13, or the combination of SEQ ID NOs: 21-24, 27-30, 36-39, 45-48, 57-60, or 65-68. As can be determined by those of skill in the art, various functionally similar or equivalent components of these CARs can be swapped or substituted with one another, as well as other similar or functionally equivalent components known in the art or listed herein.

Antibodies and Related Molecules Delivered by CAR T Cells

As noted above, the CAR T cells of the invention can optionally be used to deliver antibody reagents (or other therapeutic molecules, e.g., cytokines) to tumors, such as to the tumor microenvironment. In various embodiments, the antibody reagents are encoded by the same nucleic acid molecule as the CAR, thus facilitating transduction of cells (e.g., T cells) to express both a CAR and an antibody reagent. In such examples, the antibody reagent can be expressed, e.g., such that it is separated from the CAR (and optionally other proteins, e.g., markers) by cleavable linker sequences (e.g., a 2A linker, such as, e.g., P2A or T2A; see above). The antibody reagent can be expressed under the control of the same promoter as the CAR (e.g., by an EF1α promoter), and can be constitutively expressed. In other examples, the antibody reagent is expressed under the control of an inducible promoter, e.g., a promoter that is expressed upon T cell activation (e.g., an NFAT promoter). Such an inducible promoter can be used, e.g., to ensure that the antibody is expressed only upon T cell activation, and thus only, e.g., when the CAR T cell is within the tumor microenvironment, to which locale it may be advantageous to have antibody production limited. As is understood in the art, the CAR coding sequences can be 5' or 3' to the antibody reagent coding sequences in various vector designs within the invention.

In various examples, the antibodies expressed within a CAR T cell (e.g., from the same nucleic acid molecule as the CAR) are single chain antibodies or single domain antibodies as described herein (scFV or camelids). In the case of single chain antibodies, the chains may be in the order L-H or H-L, and optionally may be separated from one another by a linker (e.g., a glycine-based linker).

In various examples, the antibodies are bi-specific antibodies including, e.g., bispecific T cell engagers (BiTEs). Such molecules can target T cells (e.g., by binding CD3) as well as a tumor antigen (e.g., EGFR, EGFRvIII, or CD19; also see above), and can be used to augment the T cell response in, e.g., the tumor microenvironment. The two components of a BiTE can optionally be separated from one another by a linker (e.g., a glycine-based linker).

Antibody reagents can be targeted against, e.g., tumor antigens or Treg antigens, such as those described herein, or other antigens (e.g., EGFR, EGFRvIII, CD19, CTLA4, CD25, GARP, LAP, IL-15, IL13Ra2, CSF1R etc.)

In addition to optionally delivering antibody reagents, as described herein, the CAR T cells of the invention can be used to delivery other therapeutic molecules including, e.g., cytokines and toxins.

Other components of CARs and related constructs (or variants thereof), as described herein, such as $Ig_\kappa$ (e.g., SEQ ID NO: 32, 41, 50, 54, 62, or variants thereof), CD8 leader (e.g., SEQ ID NO: 2, 14, 20, or variants thereof), and related sequences, can be selected for use in making constructs of the invention, as will be apparent to those of skill in the art.

Cells and Therapy

One aspect of the technology described herein relates to a mammalian cell comprising any of the CAR polypeptides described herein (optionally together with another therapeutic molecule, e.g., an antibody reagent (e.g., a scFv, a camelid antibody, or a BiTE) or a cytokine); or a nucleic acid encoding any of the CAR polypeptides described herein (optionally together with another therapeutic molecule, e.g., an antibody reagent (e.g., a scFv, a camelid antibody, or a cytokine). In one embodiment, the mammalian cell comprises an antibody, antibody reagent, antigen-binding portion thereof, any of the CARs described herein, or a cytokine, or a nucleic acid encoding such an antibody, antibody reagent, antigen-binding portion thereof, any of the CARs described herein, or a cytokine. The mammalian cell or tissue can be of human, primate, hamster, rabbit, rodent, cow, pig, sheep, horse, goat, dog or cat origin, but any other mammalian cell may be used. In a preferred embodiment of any aspect, the mammalian cell is human.

In one embodiment, the cell is a T cell. In alternate embodiments of any aspect, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In one embodiment, the cell is obtained from an individual having or diagnosed as having cancer, a plasma cell disorder, or autoimmune disease.

"Cancer" as used herein can refer to a hyperproliferation of cells whose unique trait, loss of normal cellular control, results in unregulated growth, lack of differentiation, local tissue invasion, and metastasis, and can be glioblastoma, glioma, leukemia, lymphoma, multiple myeloma, or a solid tumor. Non-limiting examples of leukemia include acute myeloid leukemia (AML), chronic myeloid leukemia (CML), acute lymphocytic leukemia (ALL), and chronic lymphocytic leukemia (CLL). In one embodiment, the cancer is ALL or CLL. Non-limiting examples of lymphoma include diffuse large B-cell lymphoma (DLBCL), follicular lymphoma, chronic lymphocytic leukemia (CLL), small lymphocytic lymphoma (SLL), mantle cell lymphoma (MCL), marginal zone lymphomas, Burkitt lymphoma, hairy cell leukemia (HCL), and T cell lymphoma (e.g., peripheral T cell lymphoma (PTCL), including cutaneous T cell lymphoma (CTCL) and anaplastic large cell lymphoma (ALCL)). In one embodiment, the cancer is DLBCL or follicular lymphoma. Non-limiting examples of solid tumors include adrenocortical tumor, alveolar soft part sarcoma, carcinoma, chondrosarcoma, colorectal carcinoma, desmoid tumors, desmoplastic small round cell tumor, endocrine tumors, endodermal sinus tumor, epithelioid hemangioendothelioma, Ewing sarcoma, germ cell tumors (solid tumor), giant cell tumor of bone and soft tissue, hepatoblastoma, hepatocellular carcinoma, melanoma, nephroma, neuroblastoma, non-rhabdomyosarcoma soft tissue sarcoma (NRSTS), osteosarcoma, paraspinal sarcoma, renal cell carcinoma, retinoblastoma, rhabdomyosarcoma, synovial sarcoma, and Wilms tumor. Solid tumors can be found in bones, muscles, or organs, and can be sarcomas or carcinomas. It is contemplated that any aspect of the technology described herein can be used to treat all types of cancers, including cancers not listed in the instant application. As used herein, the term "tumor" refers to an abnormal growth of cells or tissues, e.g., of malignant type or benign type.

As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity. Other examples of auto-immune-related disease or disorder, but should not be construed to be limited to, include rheumatoid arthritis, multiple sclerosis (MS), systemic lupus erythematosus, Graves' disease (overactive thyroid), Hashimoto's thyroiditis (underactive thyroid), celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, acute disseminated encephalomyelitis, antiphospholipid antibody syndrome, aplastic anemia, idiopathic thrombocytopenic purpura, myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the mammalian cell is obtained for a patient having an immune system disorder that results in abnormally low activity of the immune system, or immune deficiency disorders, which hinders one's ability to fight a foreign agent (e.g., a virus or bacterial cell).

A plasma cell is a white blood cell produces from B lymphocytes which function to generate and release antibodies needed to fight infections. As used herein, a "plasma cell disorder or disease" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell disorders include amyloidosis, Waldenstrom's macroglobulinemia, osteosclerotic myeloma (POEMS syndrome), monoclonal gammopathy of unknown significance (MGUS), and plasma cell myeloma.

T cells can be obtained from a subject using standard techniques known in the field. For example, T cells can be isolated from peripheral blood taken from a donor or patient. T cells can be isolated from a mammal. Preferably, T cells are isolated from a human.

A cell, for example a T cell, can be engineered to comprise any of the CAR polypeptides described herein (including CAR polypeptides that are cleavably linked to antibody reagents or cytokines, as described herein); or a nucleic acid encoding any of the CAR polypeptides (and optionally also a genetically encoded antibody reagent or cytokine) described herein. In one embodiment, the any of the CAR polypeptides (optionally together with an antibody reagent as described herein or a cytokine) described herein are expressed from a lentiviral vector. The lentiviral vector is used to express the CAR polypeptide (and optionally also the antibody reagent or cytokine) in a cell using infection standard techniques.

Retroviruses, such as lentiviruses, provide a convenient platform for delivery of nucleic acid sequences encoding a gene or chimeric gene of interest. A selected nucleic acid sequence can be inserted into a vector and packaged in retroviral particles using techniques known in the art. The recombinant virus can then be isolated and delivered to cells, e.g., in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu et al., Pharmacological Reviews 52:493-512, 2000; which are each incorporated by reference herein in their entirety. Lentiviral system for efficient DNA delivery can be purchased from OriGene; Rockville, MD. In alternative embodiments, the CAR polypeptide (and optionally the antibody reagent or cytokine) of any of the CARS described herein are expressed in the mammalian cell via transfection or electroporation of an expression vector comprising nucleic acid encoding the CAR. Transfection or electroporation methods are known in the art.

Efficient expression of the CAR polypeptide (and optionally the antibody reagent or cytokine) of any of the polypeptides described herein can be assessed using standard assays that detect the mRNA, DNA, or gene product of the nucleic acid encoding the CAR (and optional antibody reagent or cytokine). For example, RT-PCR, FACS, northern blotting, western blotting, ELISA, or immunohistochemistry.

In one embodiment, the CAR polypeptide (and optional antibody reagent or cytokine) described herein is constitutively expressed. In one embodiment, the CAR polypeptide is constitutively expressed and the optional antibody reagent or cytokine is inducible expressed. In one embodiment, the CAR polypeptide (and optional antibody reagent or cytokine) described herein is encoded by recombinant nucleic acid sequence.

One aspect of the technology described herein relates to a method of treating cancer, a plasma cell disorder, or an autoimmune disease in a subject in need thereof, the method comprising: engineering a T cell to comprise any of the CAR polypeptides (and optional antibody reagents or cytokines) described herein on the T cell surface; and administering the engineered T cell to the subject. In the case of cancer, the method can be for treating diagnosed cancer, preventing recurrence of cancer, or for use in an adjuvant or neoadjuvant setting.

One aspect of the technology described herein relates to a method of treating cancer, a plasma cell disorder, or an autoimmune disease in a subject in need thereof, the method comprising: administering the cell of any of the mammalian cells comprising the any of the CAR polypeptides (and optional antibody reagents or cytokines) described herein.

Cluster differentiation (CD) molecules are cell surface markers present on leukocytes. As a leukocyte differentiates and matures its CD profile changes. In the case that a leukocytes turns into a cancer cell (i.e., a lymphoma), its CD profile is important in diagnosing the disease. The treatment and prognosis of certain types of cancers is reliant on determining the CD profile of the cancer cell. "CDX+", wherein "X" is a CD marker, indicates the CD marker is present in the cancer cell, while "CDX-" indicates the marker is not present. One skilled in the art will be capable of assessing the CD molecules present on a cancer cell using standard techniques, for example, using immunofluorescence to detect commercially available antibodies bound to the CD molecules.

In some embodiments of any of the aspect, the engineered CAR-T cell is stimulated and/or activated prior to administration to the subject.

Administration

In some embodiments, the methods described herein relate to treating a subject having or diagnosed as having cancer, a plasma cell disease or disorder, or an autoimmune disease or disorder with a mammalian cell comprising any of the CAR polypeptides (and optional antibody reagents or cytokines) described herein, or a nucleic acid encoding any of the CAR polypeptides (and optional antibody reagents or cytokines) described herein. As used herein, a "CAR T cells as described herein" refers to a mammalian cell comprising any of the CAR polypeptides (and optional antibody reagents or cytokines) described herein, or a nucleic acid encoding any of the CAR polypeptides (and optional antibody reagents or cytokines) described herein. As used herein, a "condition" refers to a cancer, a plasma cell disease or disorder, or an autoimmune disease or disorder. Subjects having a condition can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g., the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The compositions described herein can be administered to a subject having or diagnosed as having a condition. In some embodiments, the methods described herein comprise administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the compositions described herein are administered systemically or locally. In a preferred embodiment, the compositions described herein are administered intravenously. In another embodiment, the compositions described herein are administered at the site of a tumor.

The term "effective amount" as used herein refers to the amount of activated CAR T cells needed to alleviate at least one or more symptom of the disease or disorder, and relates to a sufficient amount of the cell preparation or composition to provide the desired effect. The term "therapeutically effective amount" therefore refers to an amount of activated CAR T cells that is sufficient to provide a particular anti-condition effect when administered to a typical subject. An effective amount as used herein, in various contexts, would also include an amount sufficient to delay the development of a symptom of the disease, alter the course of a symptom disease (for example but not limited to, slowing the progression of a condition), or reverse a symptom of the condition. Thus, it is not generally practicable to specify an exact "effective amount." However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the technology, the technology described herein relates to a pharmaceutical composition comprising activated CAR T cells as described herein, and optionally a pharmaceutically acceptable carrier. The active ingredients of the pharmaceutical composition at a minimum comprise activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulation include saline and aqueous buffer solutions, Ringer's solution, and serum component, such as serum albumin, HDL and LDL. The terms such as "excipient," "carrier," "pharmaceutically acceptable carrier" or the like are used interchangeably herein.

In some embodiments, the pharmaceutical composition comprising activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed within are well known to those skilled in the art. Examples include, without limitation: saline solution; glucose solution; aqueous vehicles including but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage for suitable one administration. By way of example, a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the activated CAR T cells described herein are administered as a monotherapy, i.e., another treatment for the condition is not concurrently administered to the subject.

A pharmaceutical composition comprising the T cells described herein can generally be administered at a dosage of $10^4$ to $10^9$ cells/kg body weight, in some instances $10^5$ to $10^6$ cells/kg body weight, including all integer values within those ranges. If necessary, T cell compositions can also be administered multiple times at these dosages. The cells can be administered by using infusion techniques that are commonly known in immunotherapy (see, e.g., Rosenberg et al., New Eng. J. Med. 319:1676, 1988).

In certain aspects, it may be desired to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the compositions described herein are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an artificial APC, e.g., an aAPC expressing anti-CD28 and anti-CD3 CDRs, and treated such that one or more CAR constructs of the technology may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can comprise administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combination Therapy

The activated CAR T cells described herein can optionally be used in combination with each other and with other known agents and therapies, as can determined to be appropriate by those of skill in the art. In one example, two or more CAR T cells targeting different Treg markers (e.g., GARP, LAP, etc.) can be administered in combination. In another example, two or more CAR T cells targeting different cancer antigens are administered in combination. In a further example, one or more CAR T cell targeting a Treg marker (e.g., GARP, LAP, etc.) and one or more CART cell targeting one or more tumor antigens are administered in combination.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The activated CAR T cells described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR T therapy and/or other therapeutic agents, procedures or modalities can be administered during periods of active disorder, or during a period of remission or less active disease. The CAR T therapy can be administered before another treatment, concurrently with the treatment, post-treatment, or during remission of the disorder.

When administered in combination, the activated CAR T cells and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, rapamycin, mycophenolic acid, steroids, FR901228, cytokines, or a peptide vaccine, such as that described in Izumoto et al., J. Neurosurg. 108:963-971, 2008.

In one embodiment, the activated CAR T cells described herein can be used in combination with a checkpoint inhibitor. Exemplary checkpoint inhibitors include anti-PD-1 inhibitors (Nivolumab, MK-3475, Pembrolizumab, Pidilizumab, AMP-224, AMP-514), anti-CTLA4 inhibitors (Ipilimumab and Tremelimumab), anti-PDL1 inhibitors (Atezolizumab, Avelomab, MSB0010718C, MED14736, and MPDL3280A), and anti-TIM3 inhibitors.

In one embodiment, the activated CAR T cells described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil Nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, RevimmuneTM), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HC1 (Treanda®). Exemplary mTOR inhibitors include, e.g., temsirolimus; ridaforolimus (formally known as deferolimus, (IR,2R,45)-4-[(2R)-2[(1R, 95,125,15R,16E,18R,19R,21R,235,24E,26E,28Z,305,325, 35R)-I,18-dihydroxy-19,30-dimethoxy-15,17,21,23,29,35-hexamethyl-2,3,10,14,20-pentaoxo-II,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RADOOI); rapamycin (AY22989, Sirolimus®); simapimod (CAS 164301-51-3); emsirolimus, (5-{2,4-Bis[(35, )-3-methylmorpholin-4-yl]pyrido[2,3-(i]pyrimidin-7-yl}-2-methoxyphenyl)methanol (AZD8055); 2-Amino-8-[iraw5, -4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[I,4-dioxo-4-[[4-(4-oxo-8-phenyl-4H-I-benzopyran-2-yl)morpholinium-4-yl]methoxy]butyl]-L-arginylglycyl-L-a-aspartylL-serine-, inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (daunorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-I-(((5)-4-methyl-I-((R)-2-methyloxiran-2-yl)-I-oxopentan-2-yl)amino)-I-oxo-3-phenylpropan-2-y0-2-((5,   )-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-RIIS')-2-[(2R)-2-methyl-2-oxiranyl]-2-oxo-I-(phenylmethyl)ethyl]-L-serinamide (ONX-0912).

One of skill in the art can readily identify a chemotherapeutic agent of use (e.g., see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18$^{th}$ edition; Therapeutic Targeting of Cancer Cells: Era of Molecularly Targeted Agents and Cancer Pharmacology, Chapters 28-29 in Abeloff's Clinical Oncology, 2013 Elsevier; and Fischer D. S. (ed.): The Cancer Chemotherapy Handbook, 4$^{th}$ ed. St. Louis, Mosby-Year Book, 2003).

In an embodiment, activated CAR T cells described herein are administered to a subject in combination with a molecule that decreases the level and/or activity of a molecule targeting GITR and/or modulating GITR functions, a molecule that decreases the Treg cell population, an mTOR inhibitor, a GITR agonist, a kinase inhibitor, a non-receptor tyrosine kinase inhibitor, a CDK4 inhibitor, and/or a BTK inhibitor.

Efficacy

The efficacy of activated CAR T cells in, e.g., the treatment of a condition described herein, or to induce a response as described herein (e.g., a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced, e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior technology or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples, which in no way should be construed as being further limiting.

EXAMPLES

Example 1. EGFRvIII-Targeted CART Cells

CAR T cells having an EGFRvIII antigen-binding moiety (e.g., CART-EGFRvIII cells) represent a promising cellular therapy for specific targeting of cytolytic cells to the tumor microenvironment, in part because EGFRvIII is specifically expressed on tumor tissue while generally absent from healthy tissue. In this example, CART-EGFRvIII cells were tested in vitro and in vivo in two animal models.

T cells from leukapheresis products obtained from deidentified healthy donors were stimulated with Dynabeads (Human T-Activator CD3/CD28) at a bead to cell ratio of 3:1 and cultured in complete RPMI 1640 medium. Ten days following stimulation and lentivirus transduction, cells were frozen and stored for use in functional assays.

Initial tests were performed in vitro to characterize the ability of CAR-EGFRvIII cells to preferentially kill tumor cells relative to untransduced control cells in a twenty-hour luciferase-based assay, shown in FIG. 1. U87vIII, a human glioma cell line, was used as target cells. In vitro characterization demonstrates that EGFRvIII CART cells mediate significant and specific cytotoxicity against U87vIII cells (FIG. 1).

Figure 2A:
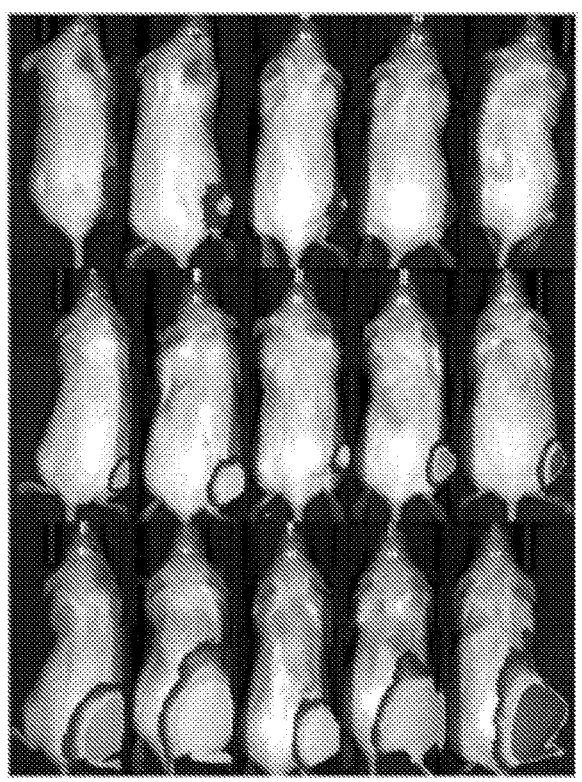
FIGS. 2A and 2B are a series of x-ray overlays showing the location of EGFRvIII expressing tumor (U87vIII) in a subcutaneous model of human glioma.
Figure 2B:
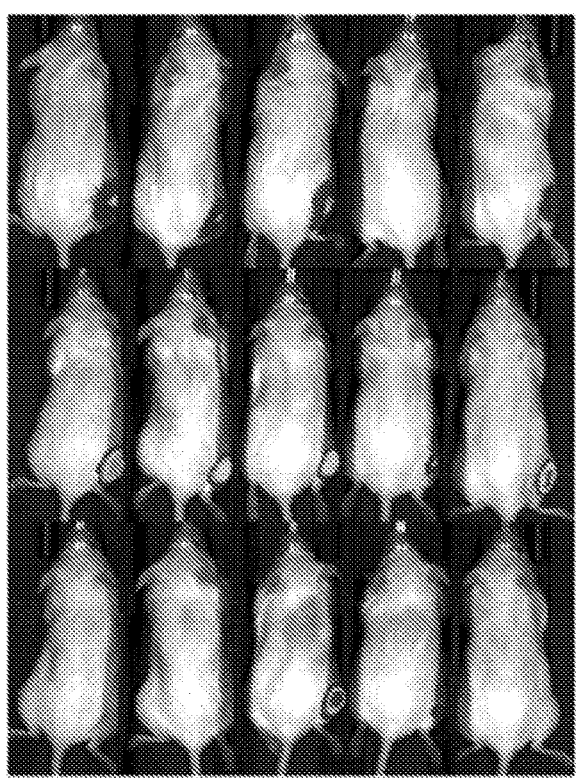
Figures 3A, 3B, 4A, 4B:
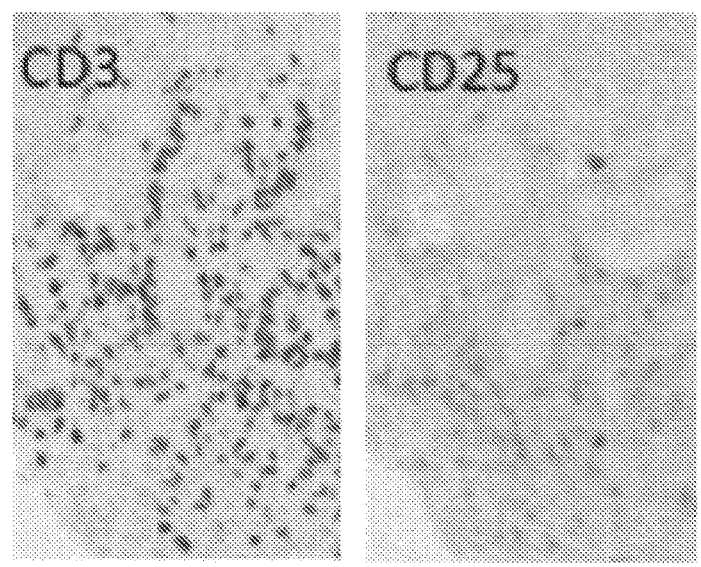
FIGS. 3A and 3B are a series of x-ray overlays showing the location of EGFRvIII expressing tumor (U87vIII) in a intracranial model of human glioma.
FIGS. 4A and 4B are photomicrographs showing immunohistochemistry of tumor tissue in one patient five days following infusion of CART-EGFRvIII.

For in vivo experiments, U87vIII tumor cells were collected in logarithmic growth phase, washed, and administered to mice subcutaneously in a xenograft model of human glioblastoma (FIGS. 2A and 2B) or intracranially in a model of human glioma (FIGS. 3A and 3B). For intracranial administrations, the needle of a 50 microliter Hamilton syringe was positioned using a stereotactic frame at 2 mm to the right of the bregma and 4 mm below the surface of the skull at the coronal suture. For treatment, mice were infused once with CAR T cells ($1 \times 10^6$ CAR-transduced T cells per mouse) via tail vein.

The potent antitumor effect observed in vitro was mirrored in the in vivo subcutaneous xenograft model of human glioblastoma (FIGS. 2A and 2B). In this model, established, bulky tumors (top rows) responded to CART-EGFRvIII (FIG. 2B), whereas untransduced cells did not prevent tumor growth (FIG. 2A). In the murine model of intracranial human glioma, EGFRvIII CAR T cells slowed the growth of tumors and led to prolonged survival (FIG. 3B) relative to untransduced cells (FIG. 3A). Although tumor growth was abrogated, the effects were not as pronounced as those observed against subcutaneous tumors.

The presence of regulatory T cells (Tregs) was observed in human patient tumor tissues after treatment with CART-EGFRvIII cells (FIGS. 4A and 4B). To determine if brain-infiltrating Tregs have a functional role in suppressing CART-EGFRvIII cells, an in vitro Treg suppression assay was performed in which CART-EGFRvIII cells (red) and glioma cells (green) were incubated in the presence of Tregs for 18 hours. Results were obtained by IncyCyte live cell analysis, as shown in FIGS. 5A-5C. While non-specific CAR cells permitted proliferation of glioma cells (FIGS. 5A and 5D, top line), CART-EGFRvIII cells killed glioma cells (FIGS. 5B and 5D, bottom line). However, addition of Tregs in the co-culture significantly reduced the ability of CART-EGFRvIII cells to kill target glioma cells (FIGS. 5C and 5D, middle line).

Figure 6A:
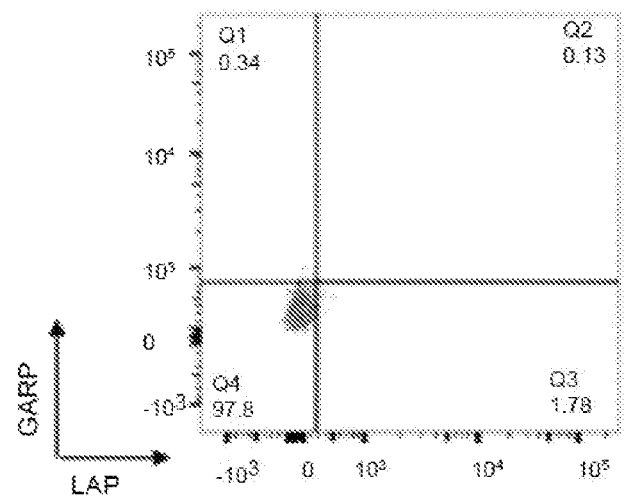
FIGS. 6A-6C are flow cytometry plots showing expression of LAP (x-axis) and GARP (y-axis) on control T cells (FIG. 6A), unactivated Tregs (FIG. 6B), and activated Tregs (FIG. 6C). Tregs were sorted from leukopak on CD4+ CD25+CD127− and expanded with CD3/CD28 beads for seven days in the presence of IL-2. On day 1, they were transduced to expressed GFP. After debeading on day 7, expanded Tregs were rested for four days before freezing. After thawing, Tregs were stained for LAP and GARP expression after overnight rest (non-activated) or overnight activation with anti-CD3 and anti-CD28. Untransduced T cells (CD4+ and CD8+) from the same donor were used as controls for expression (FIG. 6A).
Figure 6B:
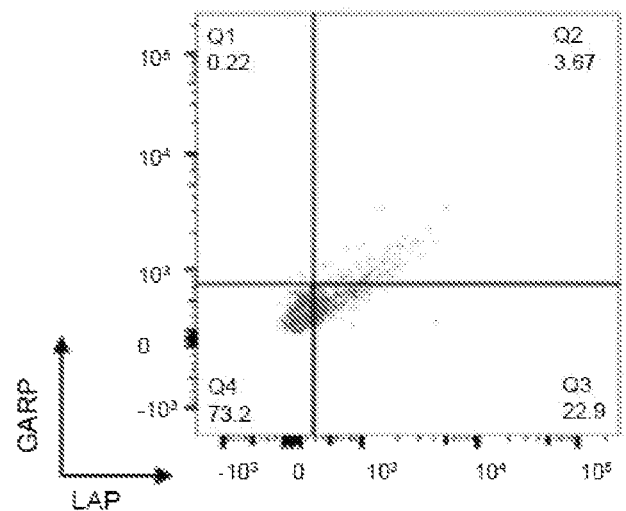
Figure 6C:
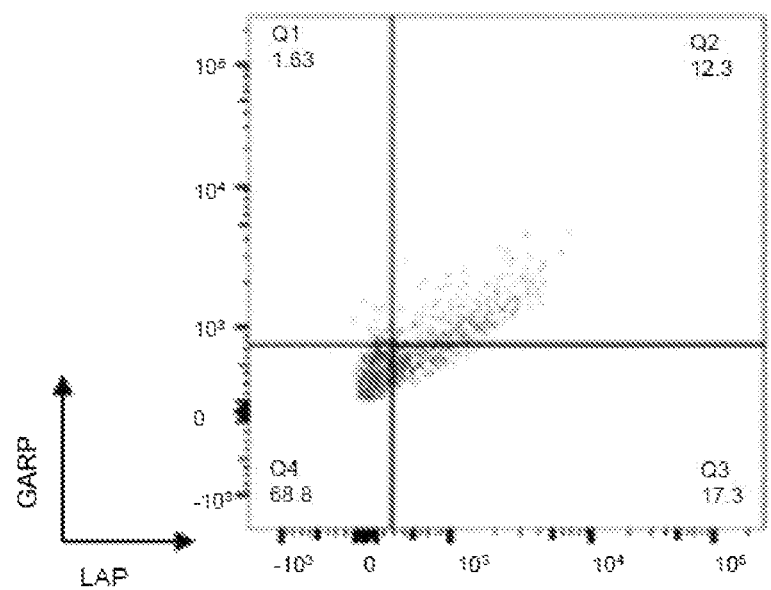
Figure 7A:
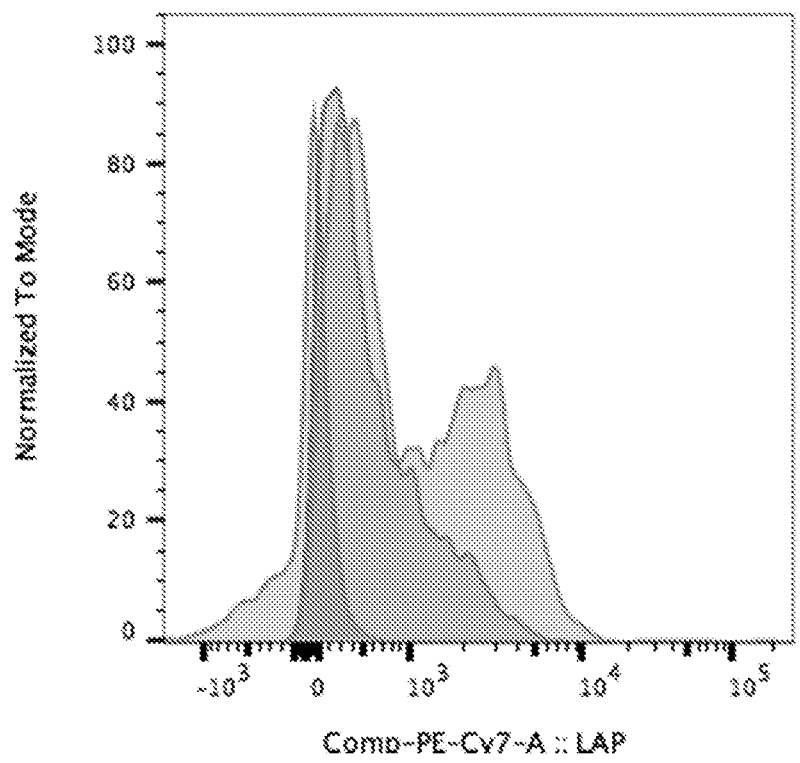
FIGS. 7A and 7B are flow cytometry histograms corresponding to the results shown in FIGS. 6A-6C showing expression of LAP (FIG. 7A) and GARP (FIG. 7B).
Figure 7B:
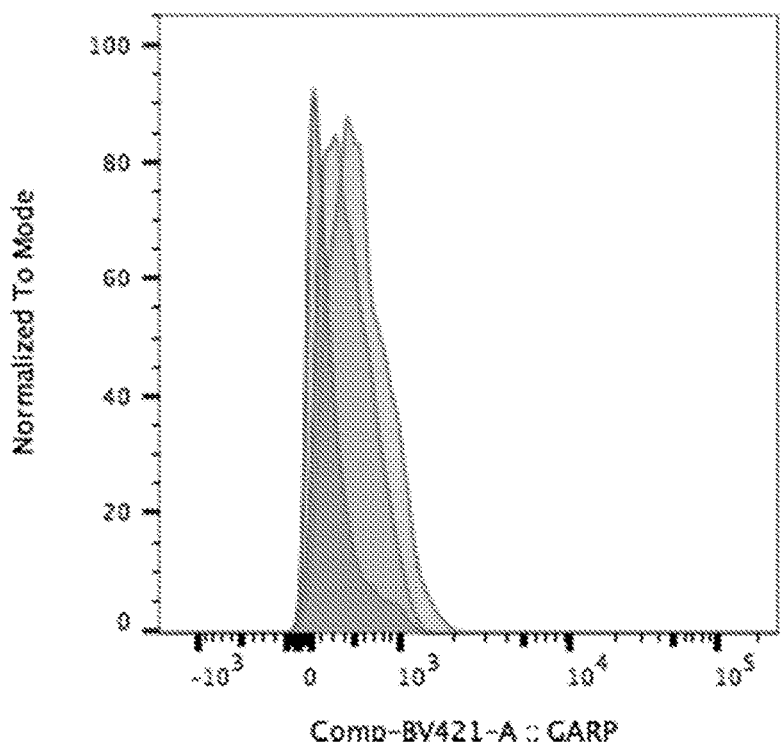

Example 2. Design and Characterization of CAR T Cells Targeted to Treg-Associated Antigens FIGS. 6A-6C, 7A, and 7B show results of an experiment in which LAP and GARP were identified as Treg-associated markers on human peripheral blood cells. In particular, among human Tregs that were not activated ex vivo, approximately 27% expressed LAP, approximately 4% were double positive for LAP and GARP (FIG. 6B). Once activated ex vivo using anti-CD3, anti-CD8, and IL-2, approximately 30% expressed LAP, and the number of LAP/GARP double positive Tregs increased to 12.3% (FIG. 6C).

Figure 8A:
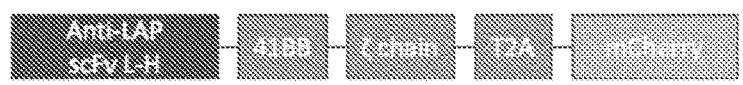
FIGS. 8A-8D are schematic drawings of CAR constructs for targeting Treg-associated antigens.
Figure 8B:
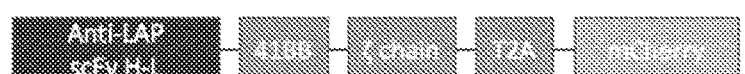
Figure 8C:
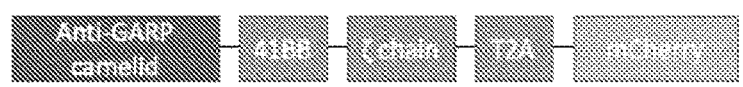
Figure 8D:

Next, CAR constructs encoding CARs targeting LAP and GARP were designed. Schematic illustrations of these constructs are shown in FIGS. 8A-8D. Treg-targeting constructs include two LAP-targeting CARs (CAR-LAP-L-H (FIG. 8A) and CAR-LAP-H-L (FIG. 8B); in which each anti-LAP scFv contains a reversal in heavy (H) and light (L) chain arrangement), a GARP-targeting CAR construct (CAR-GARP; FIG. 8C), and an EGFR-targeting CAR construct further encoding an anti-GARP camelid antibody (CAR-EGFR-GARP; FIG. 8D). Transduction efficiencies of each construct were assessed using flow cytometry by measuring the percentage of mCherry-positive cells and are provided below.

| Transduction efficiencies of Treg-targeted CAR constructs | | | |
|---|---|---|---|
| CAR construct | ND47 | ND48 | ND50 |
| pMGH 97 CAR-GARP (SEQ ID NO: 1) | 68.0% | 81.0% | 72.8% |
| pMGH 99 CAR-LAP-H-L (SEQ ID NO: 7) | 57.1% | 79.5% | 80.4% |
| pMGH 100 CAR-LAP-L-H (SEQ ID NO: 13) | 72.2% | 88.2% | 90.1% |
| pMGH 105 CAR-EGFR-GARP (SEQ ID NO: 19) | N/A | N/A | 51.2% |

Figure 9A:
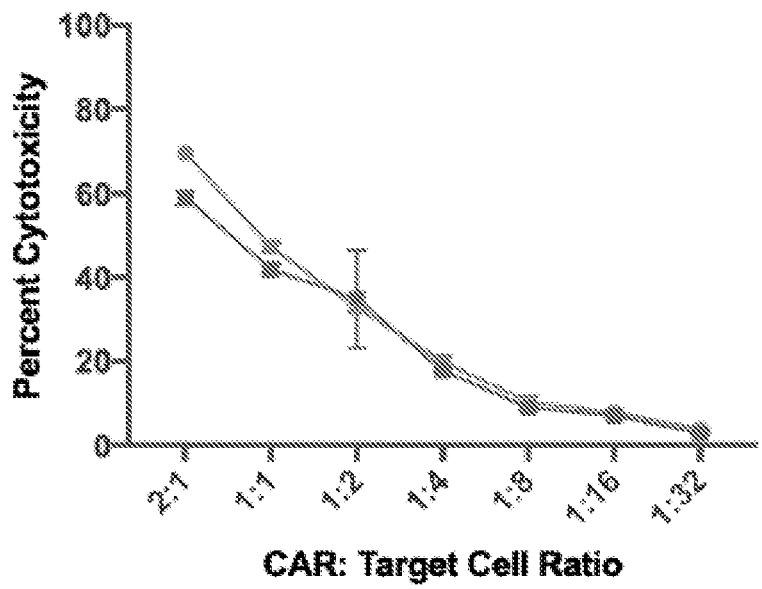
FIGS. 9A and 9B are graphs showing target Treg killing as a function of CAR T cell-to-target Treg cell ratio. Tregs were transduced with GFP, and cytotoxicity was quantified by monitoring GFP expression.
Figure 9B:
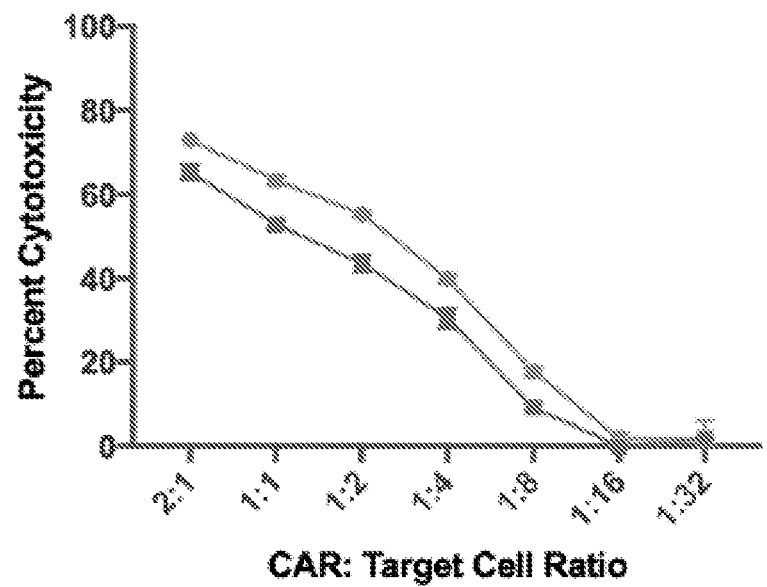
Figure 10A:
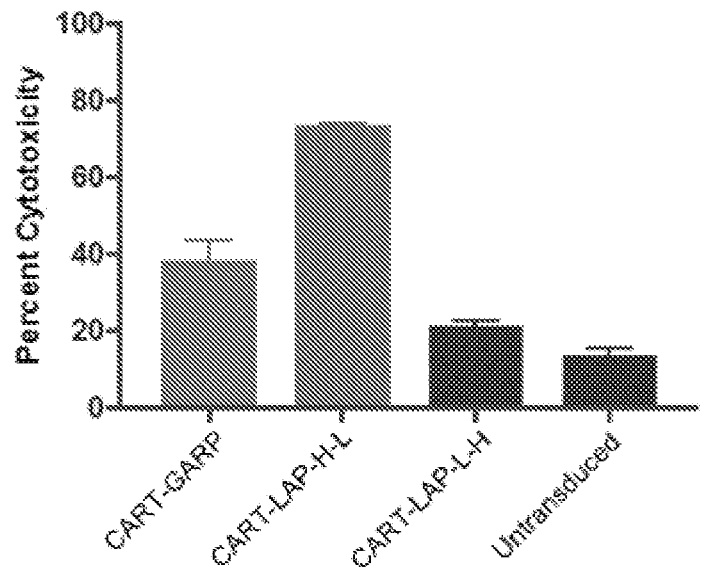
FIGS. 10A and 10B are graphs showing target Treg killing by various anti-Treg CAR T cells (i.e., CART-GARP, CART-LAP-H-L, CART-LAP-L-H, or untransduced control cells) at a 1:1 ratio of CAR T cells to Tregs for four days.
Figure 10B:
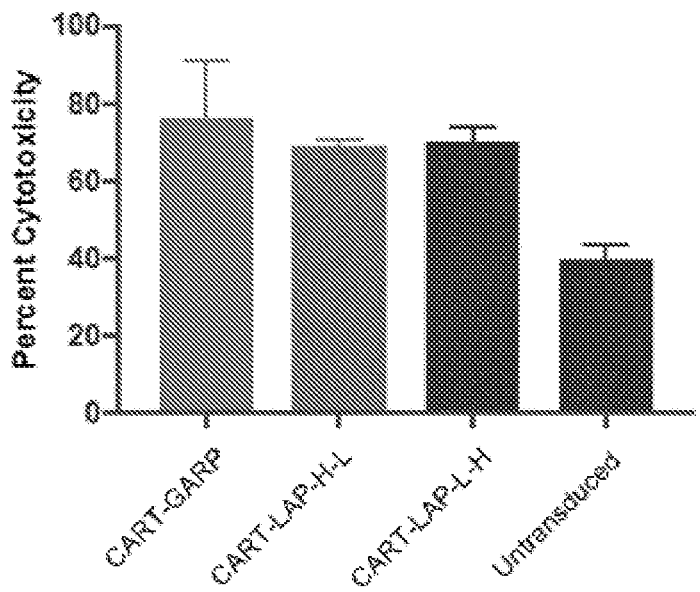
Figure 11A:
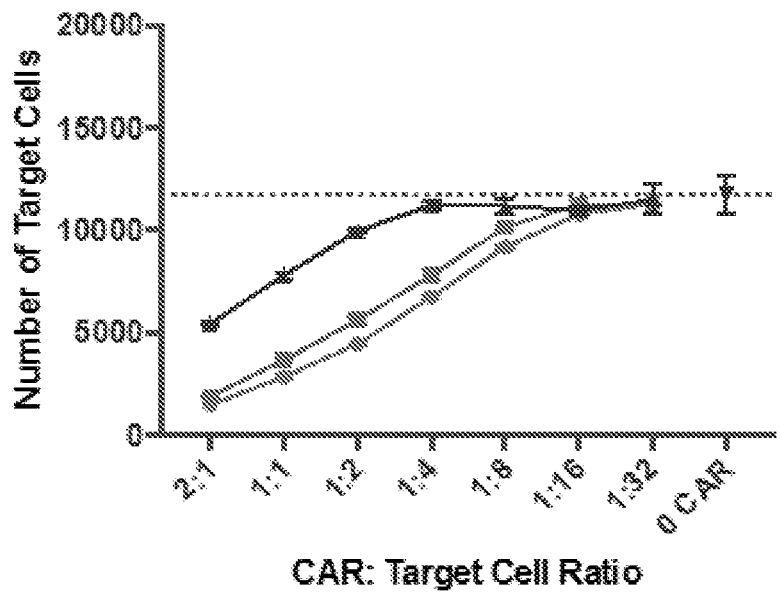
FIGS. 11A-11D are graphs showing target Treg killing as a function of CAR T cell-to-target Treg cell ratio by LAP-targeted CAR T cells after three days of coculture.
Figure 11B:
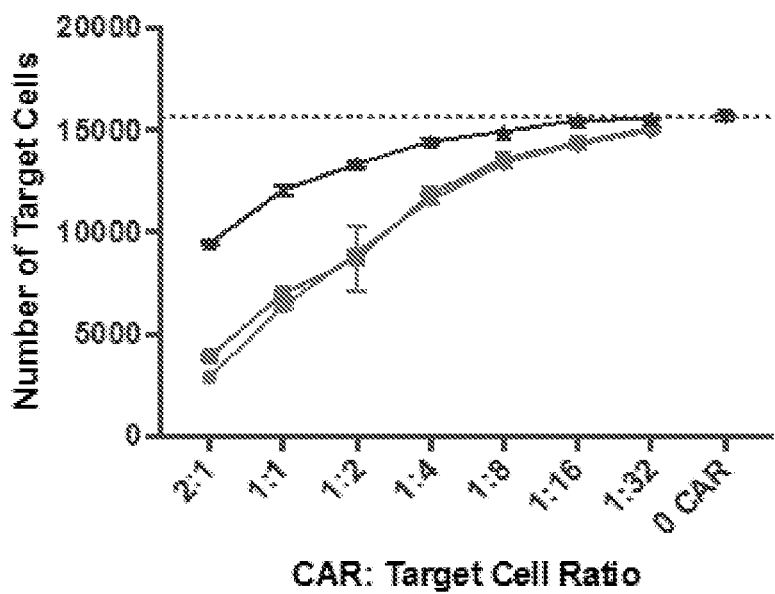
Figure 11C:
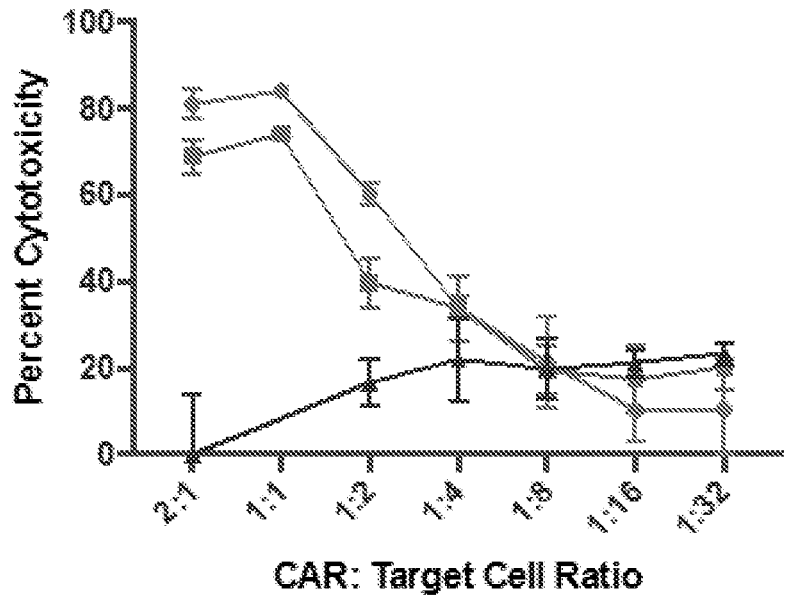
Figure 11D:
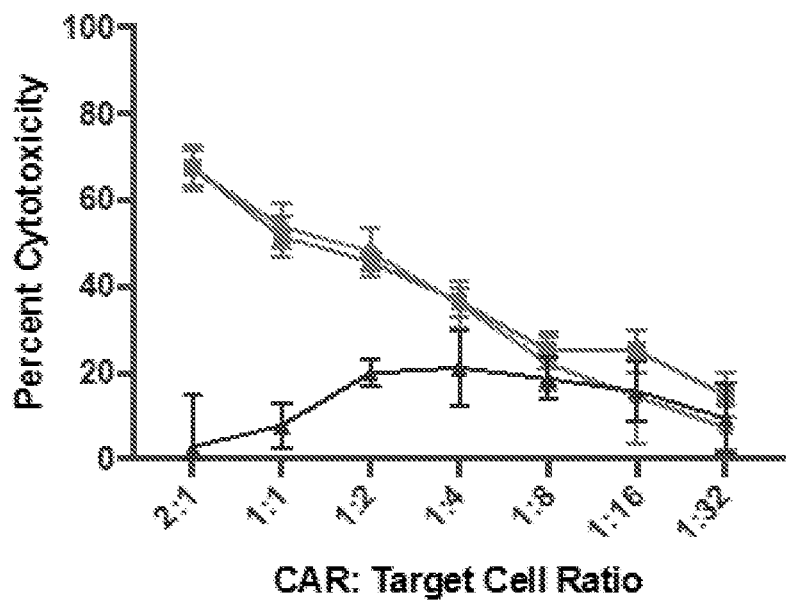

To test anti-LAP CART cells, CAR T cells were co-cultured with isolated Tregs expanded from the same donor and transduced to express GFP as a Treg marker. Tregs were activated overnight with anti-CD3 and anti-CD28 (FIG. 9B) or rested overnight (FIG. 9A) prior to the killing assay. 62,500 Tregs per well were plated. CARs were added at the indicated ratio to Tregs. Cultures were incubated for three days in the presence of 300 U/mL IL-2. Flow cytometry was performed on day 3 by collecting 30,000 events per well. Percent cytotoxicity was calculated as the percent reduction in GFP-positive cells compared to the untransduced T cell culture with Tregs. CART-LAP-H-L was more effective at killing non-activated Tregs in comparison to CART-LAP-L-H. LAP-targeted CAR T cells were then compared to GARP-targeted CART cells in an analogous Treg killing assay across two different donors at a CAR T cell-to-Treg ratio of 1:1 for four days (FIGS. 10A and 10B). FIGS. 11A and 11B characterize non-activated and activated Treg killing by LAP-targeted CAR T cells, relative to untransduced controls, by the number of target Tregs remaining at the end of a three-day coculture as a function of CAR T cell-to-Treg cell ratio. FIGS. 11C and 11D show analogous data from the same donor, in which cytotoxicity is measured by luciferase expression.

Figure 12A:
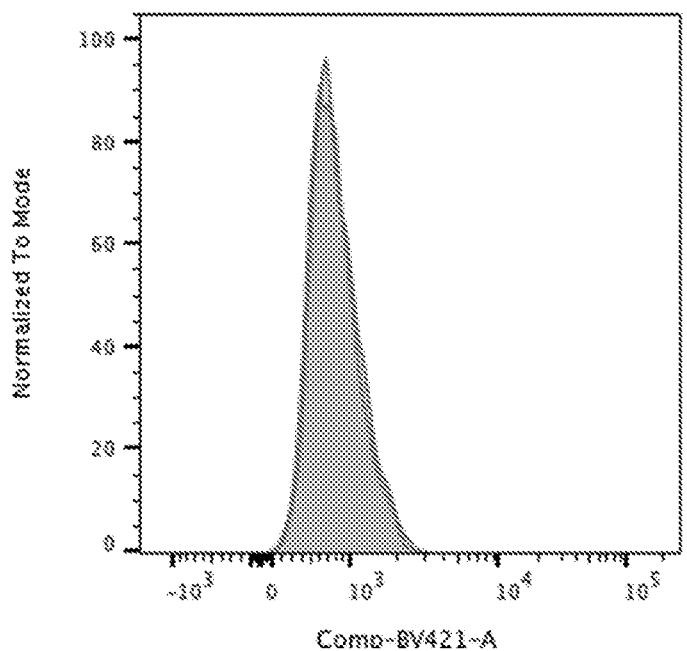
FIGS. 12A and 12B are flow cytometry histograms showing the expression of GARP (FIG. 12A) and LAP (FIG. 12B) by HUT78 cells.
Figure 12B:
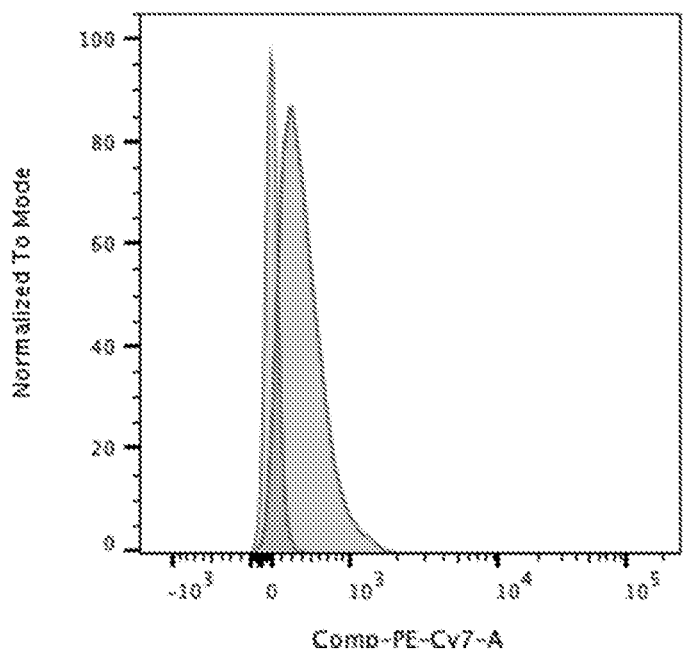
Figure 13A:
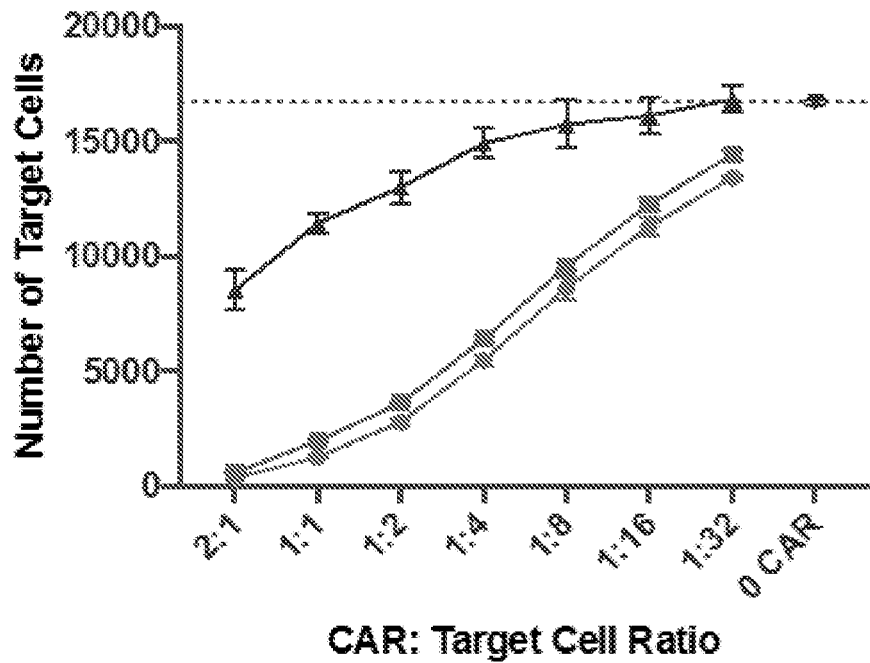
FIGS. 13A and 13B are graphs showing killing of target HUT78 cells as a function of CAR T cell-to-target cell ratio by LAP-targeted CART cells after three days of coculture.
Figure 13B:
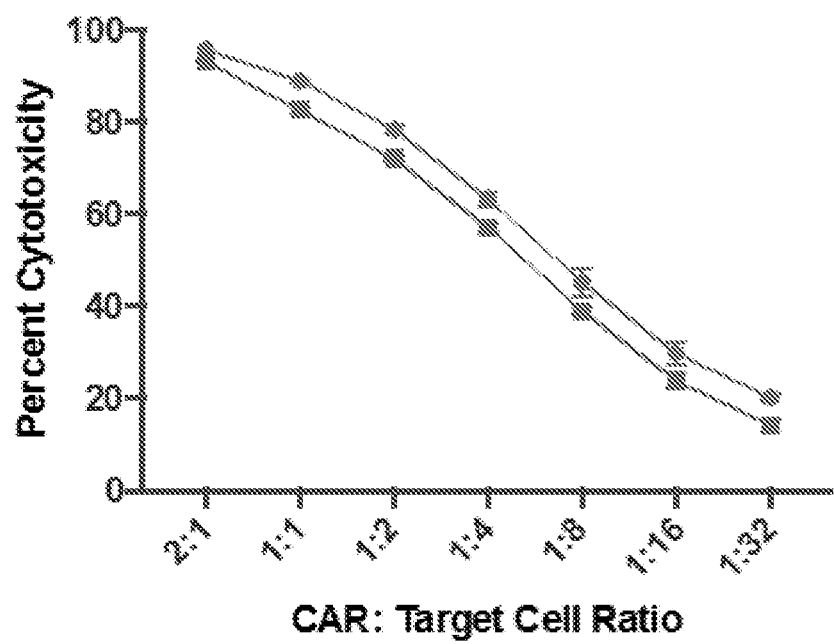
Figure 14A:
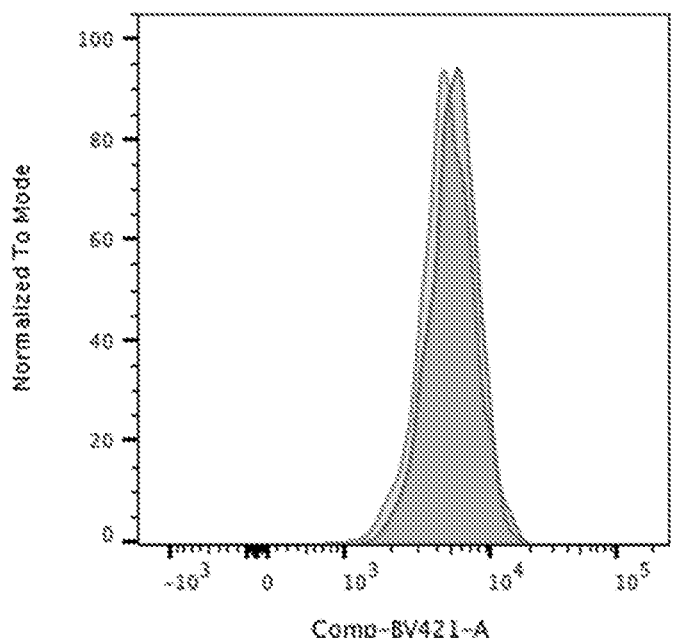
FIGS. 14A and 14B are flow cytometry histograms showing the expression of GARP (FIG. 14A) and LAP (FIG. 14B) by SeAx cells.
Figure 14B:
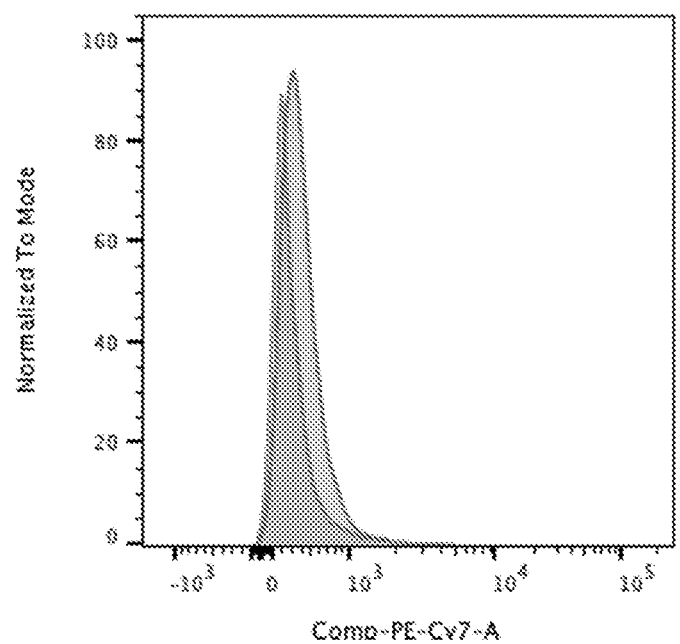
Figure 15A:
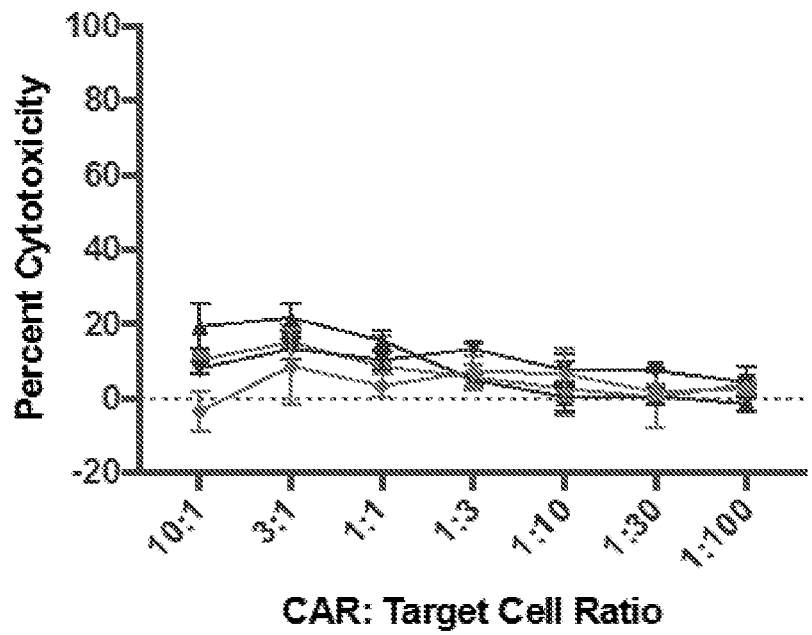
FIGS. 15A and 15B are graphs showing killing of target SeAx cells as a function of CAR T cell-to-target cell ratio by GARP and LAP-targeted CAR T cells after 24 (FIG. 15A) hours and 48 hours (FIG. 15B) of coculture, as measured by luciferase expression by target cells. Squares represent CART-GARP, upward-facing triangles represent CART-LAP-H-L, downward-facing triangles represent CART-LAP-H-L cells, and diamonds represent untransduced CAR cells.
Figure 15B:
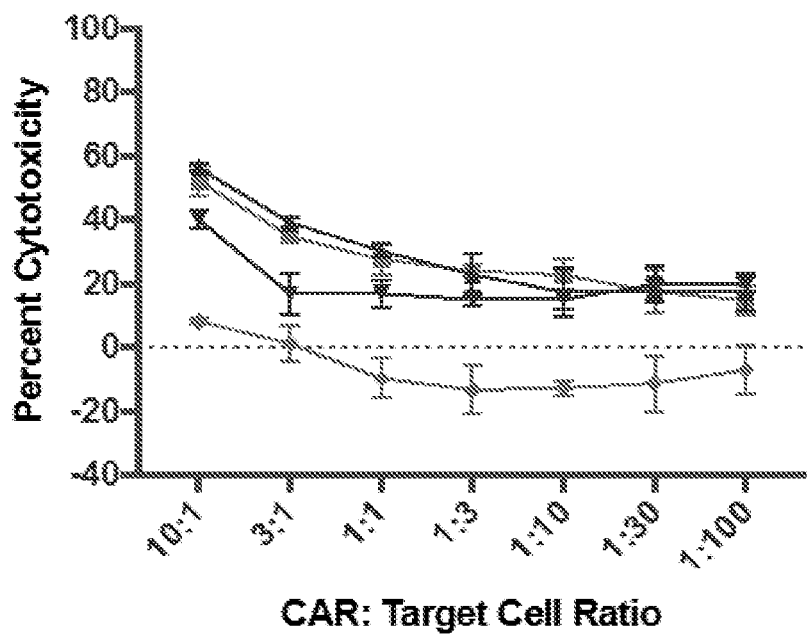

To further characterize the effect of antigen expression on function of LAP- and GARP-targeted CAR T cells, immortalized cell lines were screened for LAP and GARP antigen-expression, and the cytotoxic effect by each CAR T cell was assessed. First, HUT78 cells, a cutaneous human CD4 T cell lymphocyte-derived cell line that expresses IL-2, was stained for GARP and LAP (FIGS. 12A and 12B, respectively), and LAP expression by HUT78 cells was confirmed. Next, CART-LAP-H-L and CART-LAP-L-H cell-mediated cytotoxicity toward HUT78 cells by cytotoxicity assays (FIGS. 13A and 13B). Next, SeAx, an IL-2 dependent human Sezary syndrome-derived cell, was stained for GARP and LAP (FIGS. 14A and 14B, respectively), and expression of both antigens was confirmed. SeAx cells were cocultured with CART-GARP cells, CART-LAP-H-L cells, CART-LAP-L-L cells, and untransduced cells to quantify CAR T cell-mediated killing at 24 hours (FIG. 15A) and 48 hours (FIG. 15B). Each CAR T exhibited superior SeAx target cell killing at 24 hours, with a more pronounced effect at 48 hours. CART-GARP and CART-LAP-H-L killed target SeAx cells with greater efficiency than CART-LAP-L-H cells by 48 hours.

Figure 16A:
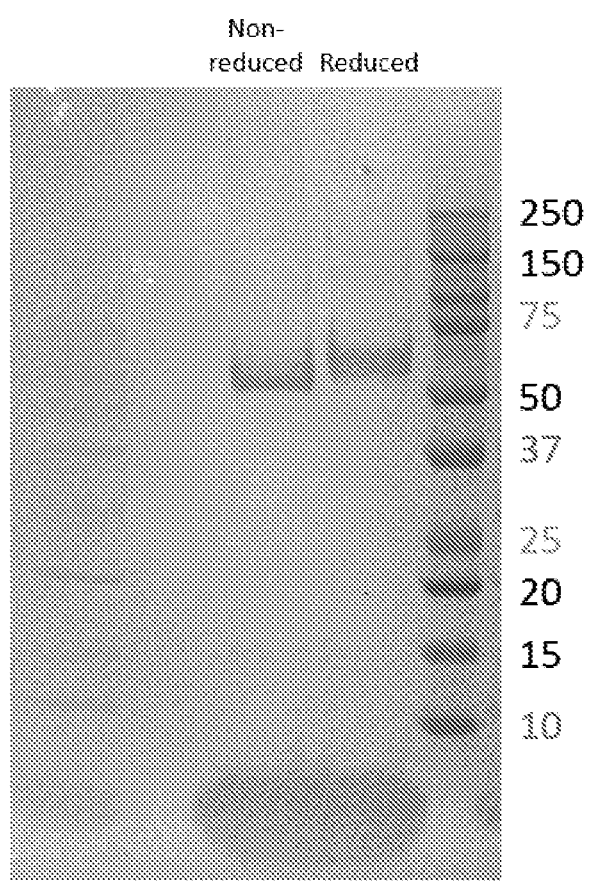
FIGS. 16A-16C are photographs of western blots showing the presence of protein components of supernatants obtained from cultures of CART-EGFR-GARP T cells.
Figure 16B:
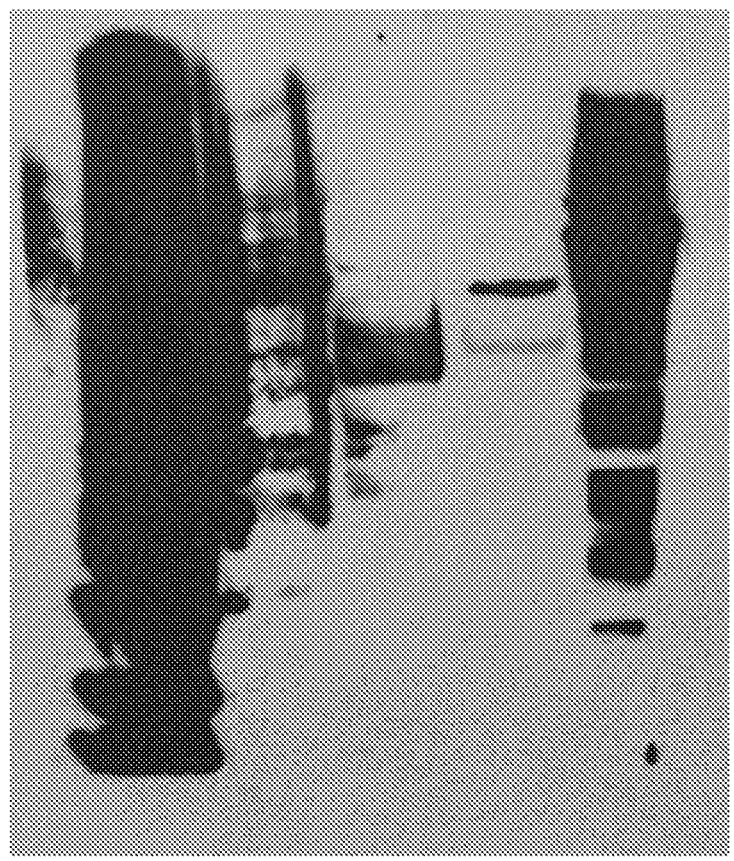
Figure 16C:
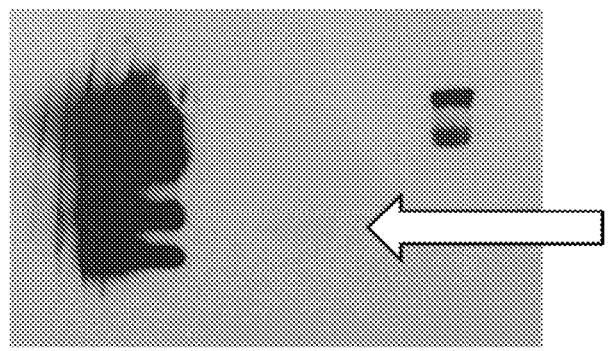

Next, secretion of anti-GARP camelid antibodies by CART-EGFR-GARP cells was characterized by western blot (FIGS. 16A-16C). Supernatant was collected from cultures containing CART-EGFR-GARP cells, treated in reducing and non-reducing conditions, and presence of a band between 10 and 15 kD was observed in the lane containing the non-reduced sample (FIG. 16C), confirming the presence of a camelid antibody.

Example 3. Design and Characterization of BiTE-Secreting CAR T Cells

Another mechanism provided herein to enhance efficacy of CAR T cell activity within tumor microenvironments (e.g., to overcome immune regulation by Tregs) is through a CAR T cell that secretes a immune-modulating antibodies, such as a BiTE. Without wishing to be bound by theory, the present inventors have discovered that expression of an immune-modulating antibody (e.g., a BiTE) from a construct that also encodes a CAR can further amplify antitumor effects.

Figure 17:
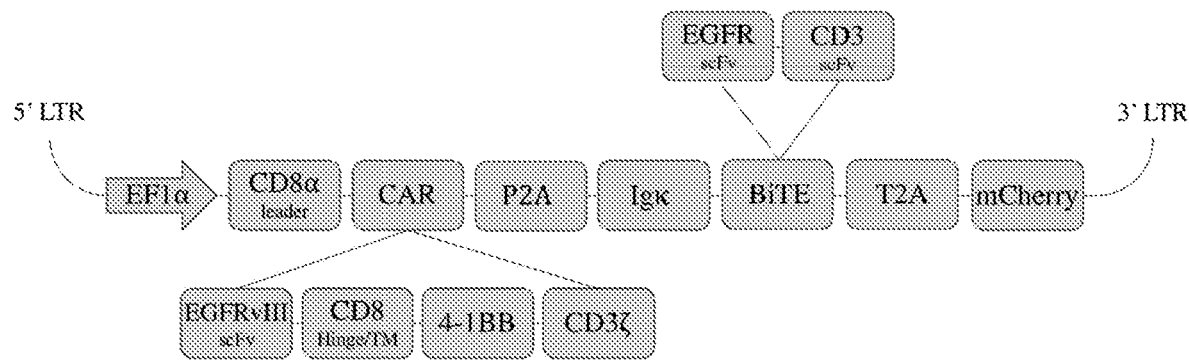
FIG. 17 is a schematic drawing of CAR-EGFR-BiTE-(EGFR-CD3), an exemplary nucleic acid molecule encoding a CAR and a BiTE.
Figure 18:
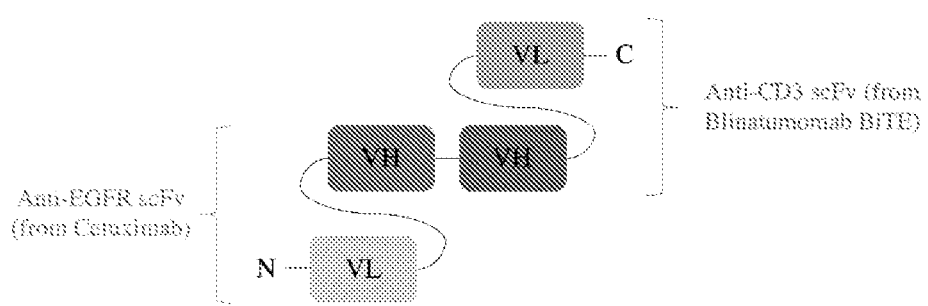
FIG. 18 is a schematic drawing of a BiTE having an anti-EGFR domain derived from cetuximab and an anti-CD3 domain derived from blinatumomab.
Figure 26A:
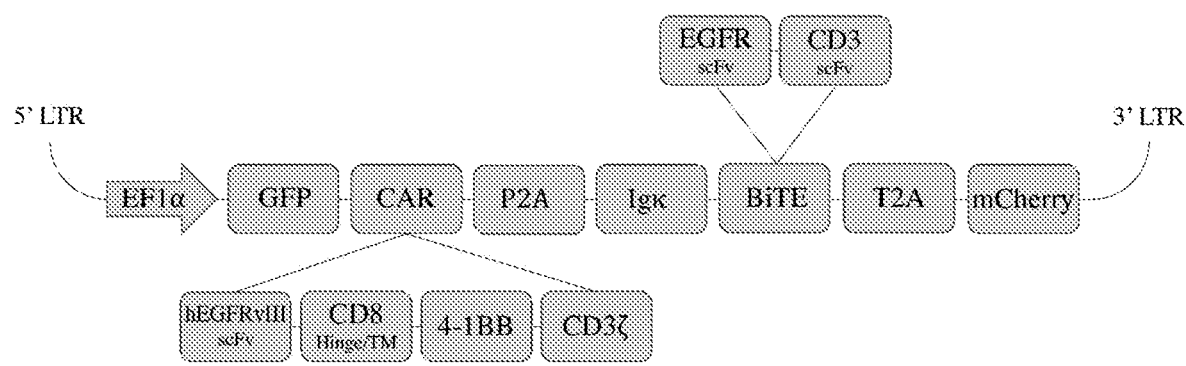
FIG. 26A is a schematic drawing of GFP-CAR-EGFR-BiTE-(EGFR-CD3), an exemplary nucleic acid molecule encoding a CAR and a constitutively expressed BiTE.
Figure 26B:
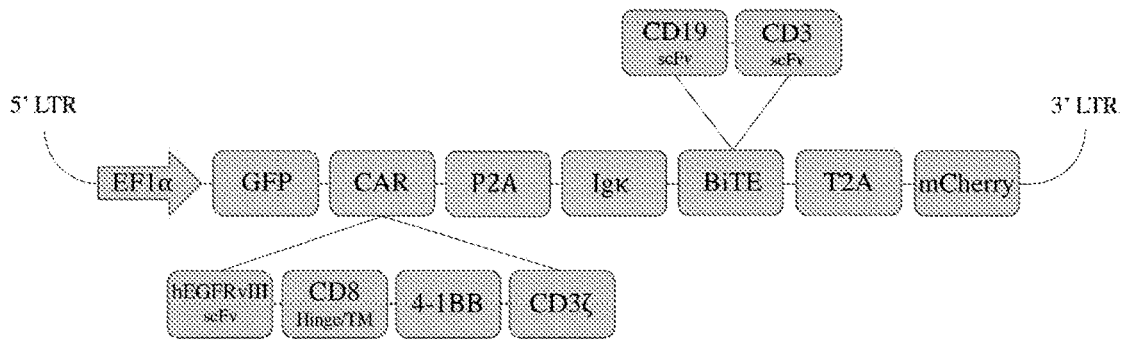
FIG. 26B is a schematic drawing of GFP-CAR-EGFR-BiTE-(CD19-CD3), an exemplary nucleic acid molecule encoding a CAR and a constitutively expressed BiTE.

One exemplary nucleic acid construct, CAR-EGFR-BiTE-(EGFR-CD3), shown schematically in FIG. 17, includes a CAR-encoding polynucleotide operatively linked 5' to a BiTE-encoding polynucleotide. The CAR features a tumor-antigen binding domain that binds to EGFRvIII, which directs the CAR T cell to the microenvironment of an EGFRvIII-positive tumor. The BiTE binds at one domain to EGFR and at the other domain to CD3, as shown in FIG. 18, which can (a) further enhance binding avidity of the host CAR T cell to the tumor cell or (b) arm neighboring (e.g., endogenous) T cells against the tumor. The BiTE is flanked by cleavable linkers P2A and T2A to enable separate secretion of the BiTE, while the CAR is targeted to the cell surface. Other exemplary BiTE-encoding CAR constructs (e.g., encoding a BiTE targeting CD19) are depicted in FIGS. 26A and 26B.

Figure 19:
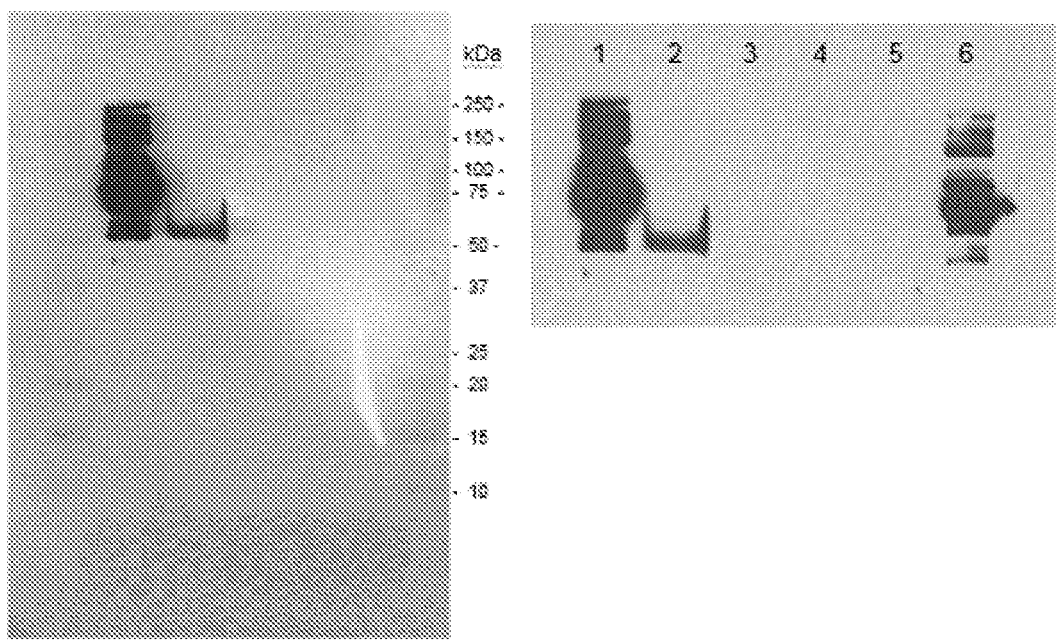
FIG. 19 is a set of photographs showing a western blot experiment verifying the presence of BiTE in lane 2.

BiTE secretion by CART-EGFR-BiTE-(EGFR-CD3) cells was confirmed by isolating supernatant from cultures containing SupT1 cells transduced with CAR-EGFR-BiTE-(EGFR-CD3), calculating the concentration of BiTE in the supernatant based on OD450, and performing western blot analysis. The concentration of BiTE in the supernatant was 0.604 ng/mL. Results of a western blot experiment are shown in FIG. 19. A band in lane two at about 50-60 kD was observed, indicating the presence of BiTE molecules in the supernatant.

Figures 20A, 20B:
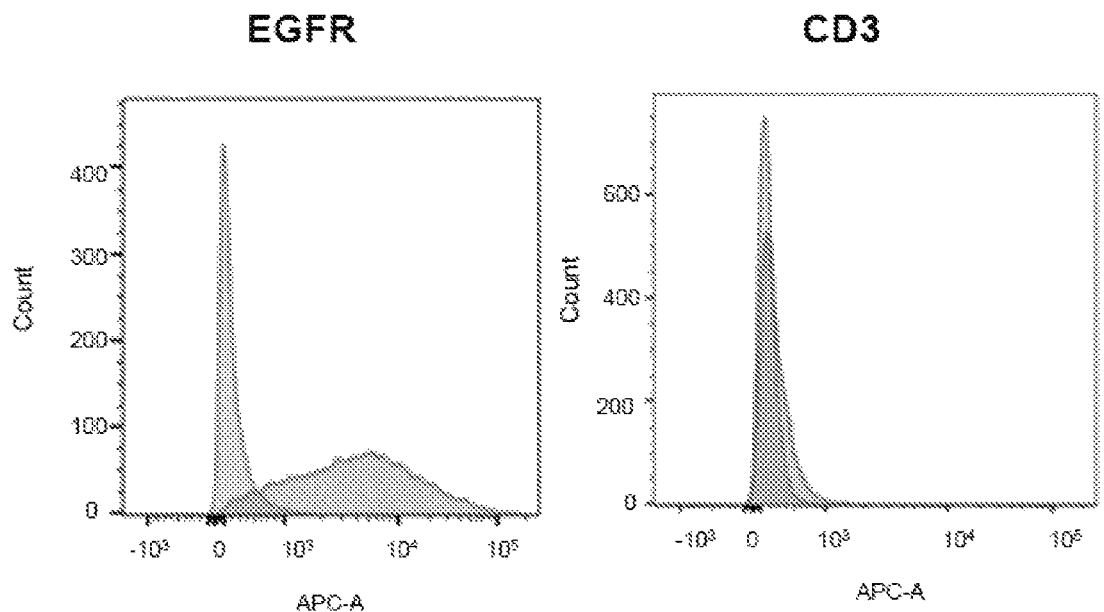
FIGS. 20A and 20B are a set of flow cytometry graphs showing binding of BiTE expressed by HEK293 cells transduced with CAR-EGFR-BiTE-(EGFR-CD3) to EGFR expressed by K562 cells (FIG. 20A) and CD3 expressed by Jurkat cells (FIG. 20B).

Next, binding of BiTE molecules was assessed by flow cytometry. HEK293T cells were transduced with CAR-EGFR-BiTE-(EGFR-CD3), and supernatants containing secreted BiTEs were collected and incubated with K562 cells (FIG. 20A) and Jurkat cells (FIG. 20B). As shown in FIG. 20A, BiTEs bound K562 cells expressing EGFR and did not bind K562 cells expressing CD19, confirming function of the EGFR-binding domain of the BiTE. As shown in FIG. 20B, CD3-expressing Jurkat cells showed stronger staining for BiTE after incubation with supernatant from CAR-EGFR-BiTE-(EGFR-CD3)-expressing HEK293T cells, compared to staining for BiTE after incubation with supernatant from untransduced HEK293T cells, indicating that BiTEs also functionally bind to CD3.

Figures 21A, 21B:
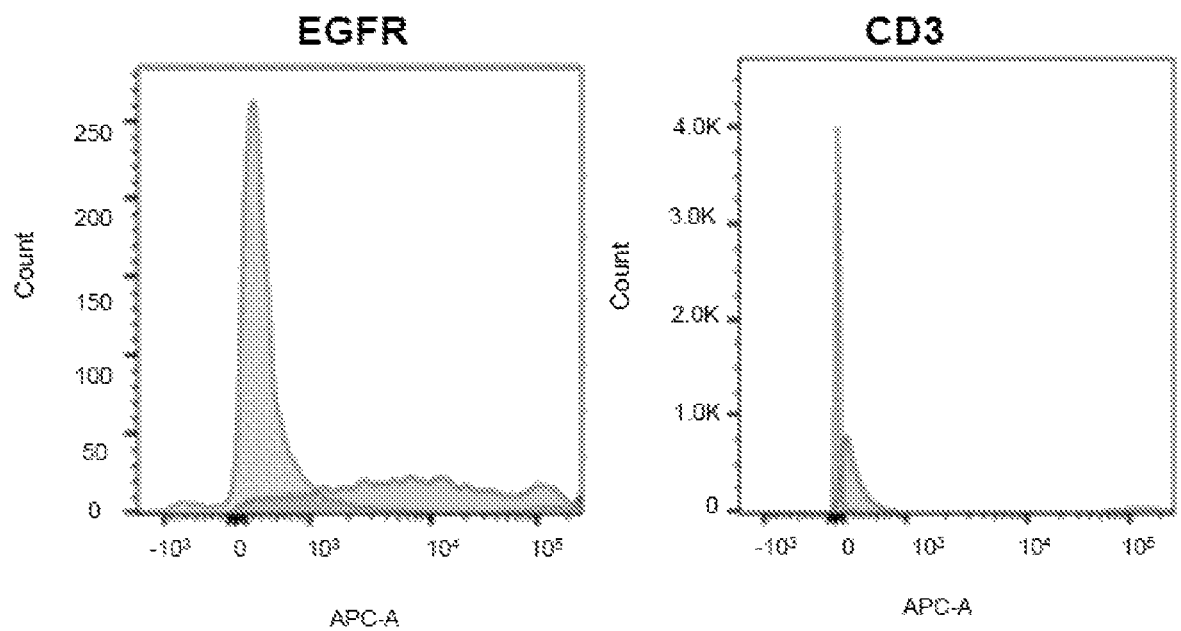
FIGS. 21A and 21B are a set of flow cytometry graphs showing binding of BiTE expressed by SupT1 cells transduced with CAR-EGFR-BiTE-(EGFR-CD3) to EGFR expressed by K562 cells (FIG. 21A) and CD3 expressed by CAR-EGFR-BiTE-(EGFR-CD3)-expressing SupT1 cells (FIG. 21B).
Figures 22A, 22B:
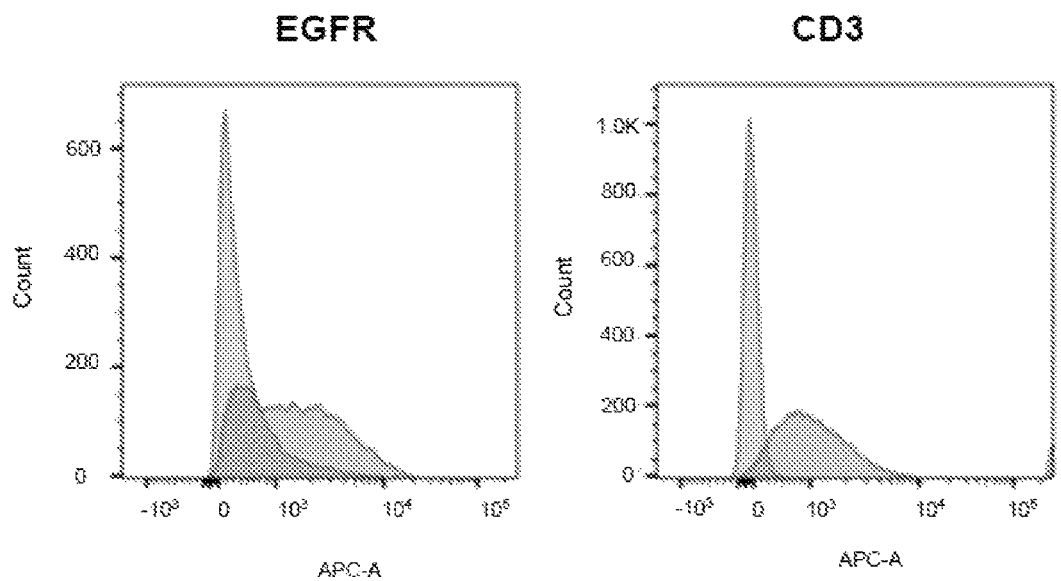
FIGS. 22A and 22B are a set of flow cytometry graphs showing binding of BiTE expressed by ND4 cells transduced with CAR-EGFR-BiTE-(EGFR-CD3) to EGFR expressed by K562 cells (FIG. 21A) and CD3 expressed by CAR-EGFR-BiTE-(EGFR-CD3)-expressing ND4 cells (FIG. 21B).

A similar experiment was conducted using SupT1 cells as transduction hosts for CAR-EGFR-BiTE-(EGFR-CD3). FIG. 21A shows BiTEs bound K562 cells expressing EGFR and did not bind K562 cells expressing CD19, confirming function of the EGFR-binding domain of the BiTE expressed by transduced SupT1 cells. To confirm that BiTEs bound to CD3 expressed on the surface of the host SupT1 cell, the transduced SupT1 cells were stained for BiTE. Results, shown in FIG. 21B, confirm that transduced SupT1 cells stain positive for BiTEs. ND4 cells were also assessed for ability to secrete functional BiTEs upon transduction with CAR-EGFR-BiTE-(EGFR-CD3). FIG. 22A shows BiTEs secreted by transduced ND4 cells bound K562 cells expressing EGFR and did not bind K562 cells expressing CD19. As shown in FIG. 22B, BiTEs bound to CD3 expressed on the transduced ND4 cells from which they were secreted.

Figure 23:
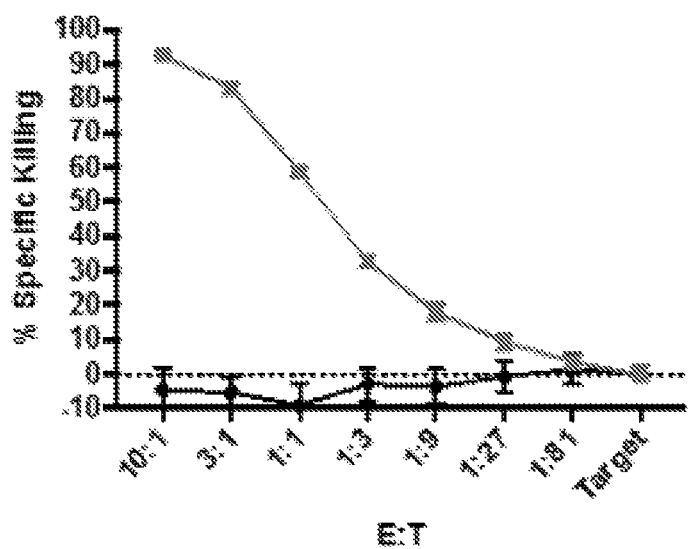
FIG. 23 is a graph showing killing of U87vIII cells by ND4 cells incubated with BiTE secreted by HEK293T cells that were transduced with CAR-EGFR-BiTE-(EGFR-CD3), as a function of effector (untransduced ND4) to target (U87vIII) cell ratio. Squares represent the experimental group in which the supernatant contained BiTE, and circles represent a negative control containing no BiTE.

Next, the ability of BiTEs secreted from transduced CAR T cells was characterized in vitro. Supernatants containing BiTEs secreted from HEK293T cells transduced with CAR-EGFR-BiTE-(EGFR-CD3) were incubated with a coculture of untransduced ND4 cells and U87vIII target cells at varying ratios. As shown in FIG. 23, ND4 cells, when incubated with BiTE, in a dose-dependent manner, indicating that BiTEs were binding to both ND4-expressed CD3 and U87vIII-expressed EGFR to a degree sufficient to induce killing by ND4 cells.

Figure 24:
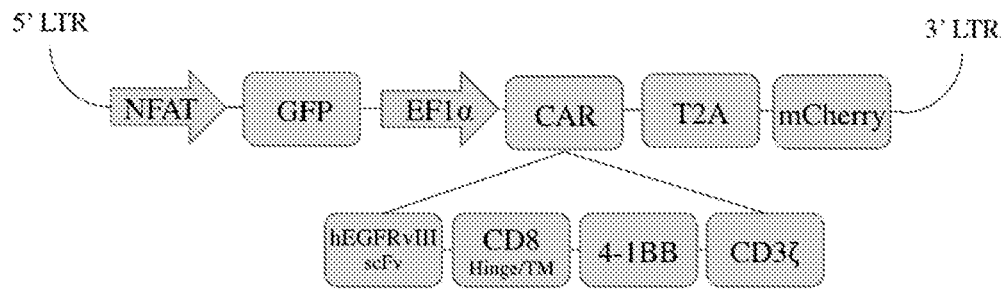
FIG. 24 is a drawing of an exemplary nucleic acid molecule encoding a CAR under control of an EF1α promoter and GFP under control of an NFAT promoter.
Figure 25A:
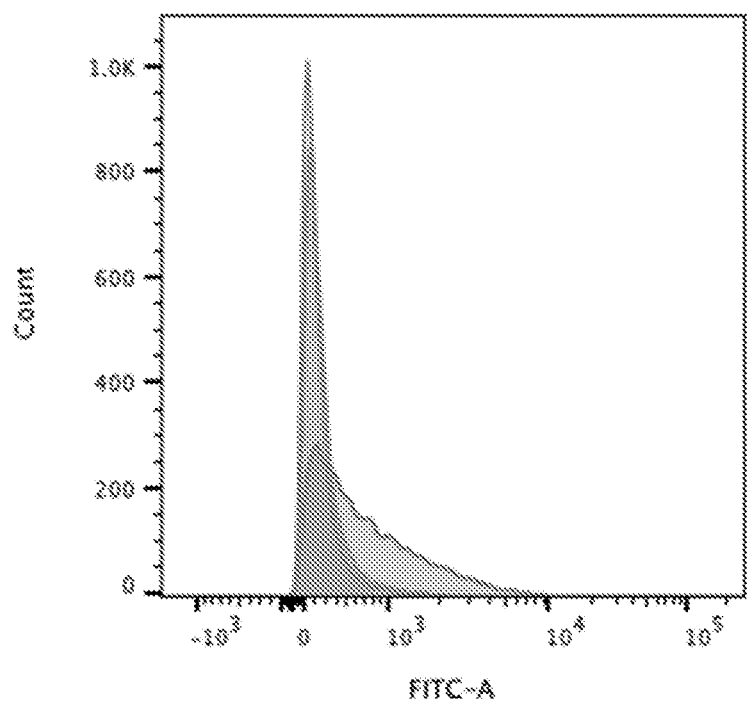
FIGS. 25A and 25B are a set of flow cytometry graphs showing GFP expression by cells transduced with the construct of FIG. 24. The red histogram shows GFP expression in unstimulated cells; the blue histogram shows GFP expression in cells stimulated with PMA and ionomycin; and the orange histogram shows GFP expression in cells coated with PEPvIII.
Figure 25B:
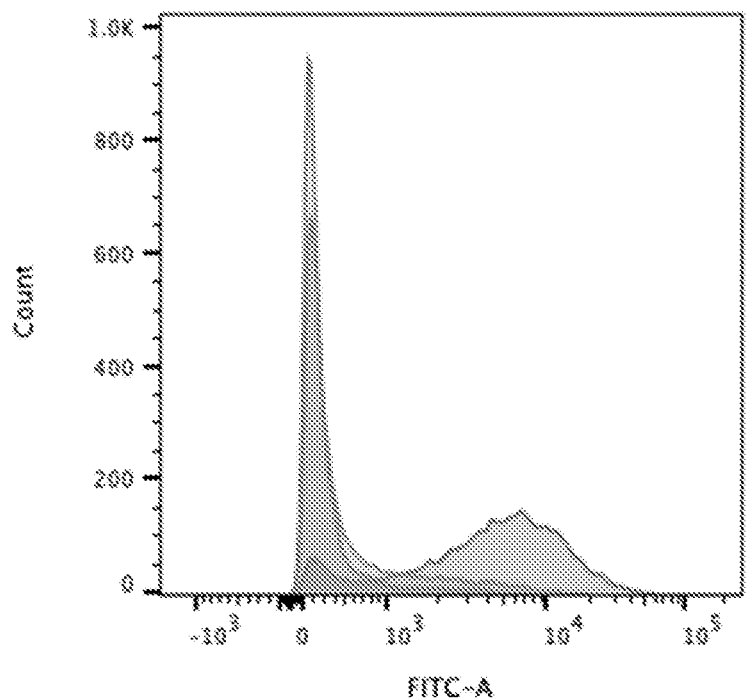
Figure 27A:
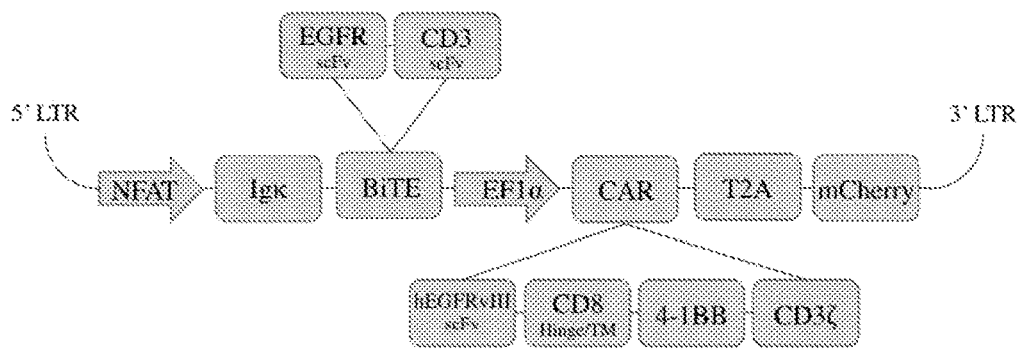
FIG. 27A is a schematic drawing of BiTE-(CD19-CD3)-CAR-EGFR, an exemplary nucleic acid molecule encoding a CAR and an inducibly expressed BiTE.
Figure 27B:
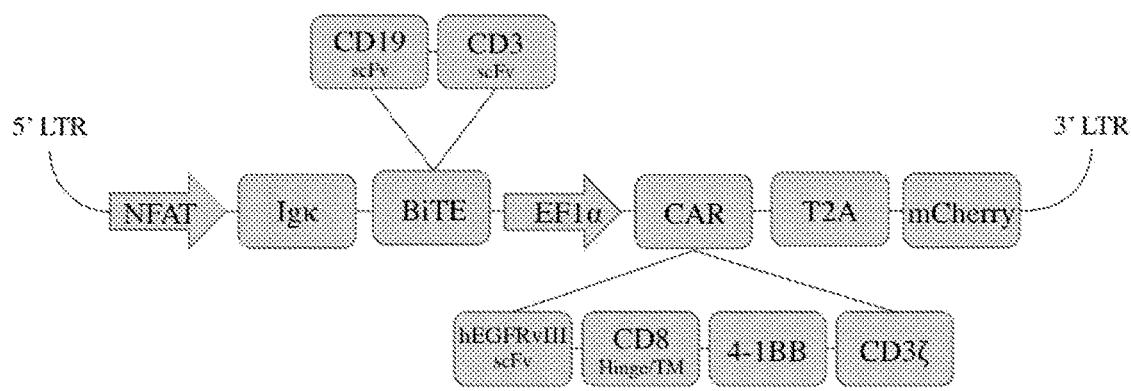
FIG. 27B is a schematic drawing of BiTE-(CD19-CD3)-CAR-EGFR, an exemplary nucleic acid molecule encoding a CAR and an inducibly expressed BiTE.

To enable inducible expression of BiTE upon T cell activation, a construct containing an NFAT promoter was designed and synthesized. As shown in FIG. 24, the NFAT promoter precedes a GFP-encoding polynucleotide, and the construct further includes a downstream CAR-encoding polynucleotide driven by EF1α, a constitutive promoter. To confirm the inducible expression of GFP, GFP expression was assessed by FACS in response to TCR stimulation by PMA/ionomycin. As shown in FIGS. 25A and 25B, stimulation triggered the expression of GFP. This inducible expression was inhibited by incubation with PEPvIII. Inducible BiTE constructs encoding CARs are designed by positioning the BiTE downstream of an inducible promoter, such as an NFAT promoter, as shown in FIGS. 27A and 27B.

Example 4. Sequence Information

Anti-GARP CAR-pMGH 97: CD8 Leader-anti-GARP-CD8 hinge+TM-4-1BB-CD3z (SEQ ID NO: 1) comprising CD8 leader sequence (amino acids 1-21 of SEQ ID NO: 1; SEQ ID NO: 2); anti-GARP camelid (amino acids 22-128 of SEQ ID NO: 1; SEQ ID NO: 3); CD8 hinge/TM domain (amino acids 129-197 of SEQ ID NO: 1; SEQ ID NO: 4); 4-1BB ICD (amino acids 198-239 of SEQ ID NO: 1; SEQ ID NO: 5); and CD3 (amino acids 240-351 of SEQ ID NO: 1; SEQ ID NO: 6).

MALPVTALLLPLALLLHAARPDIQMTQSPSSLSASLGDRVTITCQASQSI
SSYLAWYQQKPGQAPNILIYGASRLKTGVPSRFSGSGSGTSFTLTISGLE
AEDAGTYYCQQYASVPVTFGQGTKVELKTTTPAPRPPTPAPTIASQPLSL
RPEACRPAAGGAVHTRGLDFACDIYIWAPLAGTCGVLLLSLVITLYCKRG
RKKLLYIFKQPFMRPVQTTQEEDGCSCRFPEEEEGGCELRVKFSRSADAP
AYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPP
R (SEQ ID NO: 1)

CD8 leader sequence (amino acids 1-21 of SEQ ID
NO: 1; SEQ ID NO: 2)
MALPVTALLLPLALLLHAARP anti-GARP camelid (amino acids 22-128 of SEQ ID
NO: 1; SEQ ID NO: 3)
DIQMTQSPSSLSASLGDRVTITCQASQSISSYLAWYQQKPGQAPNILIYG
ASRLKTGVPSRFSGSGSGTSFTLTISGLEAEDAGTYYCQQYASVPVTFGQ
GTKVELK CD8 hinge/TM domain (amino acids 129-197 of SEQ ID
NO: 1; SEQ ID NO: 4)
TTTPAPRPPTPAPTIASQPLSLRPEACRPAAGGAVHTRGLDFACDIYIWA
PLAGTCGVLLLSLVITLYC 4-1BB ICD (amino acids 198-239 of SEQ ID NO: 1;
SEQ ID NO: 5)
KRGRKKLLYIFKQPFMRPVQTTQEEDGCSCRFPEEEEGGCEL CD3ζ (amino acids 240-351 of SEQ ID NO: 1; SEQ
ID NO: 6)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR Anti-LAP CAR (H-L)-pMGH 99: CD8 Leader-anti-LAP-CD8 hinge+TM-4-1BB-CD3z (SEQ ID NO: 7) comprising CD8 leader sequence (amino acids 1-21 of SEQ ID NO: 7; SEQ ID NO: 8), anti-LAP scFv (H-L) (amino acids 22-307 of SEQ ID NO: 7; SEQ ID NO: 9), CD8 hinge/TM domain (amino acids 308-376 of SEQ ID NO: 7; SEQ ID NO: 10), 4-1BB ICD (amino acids 377-418 of SEQ ID NO: 7; SEQ ID NO: 11), and CD3 (amino acids 419-530 of SEQ ID NO: 7; SEQ ID NO: 12).

MALPVTALLLPLALLLHAARPMKLWLNWIFLVTLLNDIQCEVKLVESGGG
LVQPGGSLSLSCAASGFTFTDYYMSWVRQPPGKALEWLGFIRNKPNGYTT
EYSASVKGRFTISRDNSQSILYLQMNVLRAEDSATYYCARYTGGGYFDYW
GQGTTLTVSSGGGGSGGGGSGGGGSGGGGSMMSSAQFLGLLLLCFQGTRC
DIQMTQTTSSLSASLGDRLTISCRASQDISNYLNWYQQKPDGTVKLLIYY
TSRLHSGVPSRFSGSGSGTDYSLTISNLEQADIATYFCQQGDTLPWTFGG
GTKLEIKTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQE
EDGCSCRFPEEEEGGCELRVKFSRSADAPAYQQGQNQLYNELNLGRREEY
DVLDKRRGRDPEMGGKPRRKNPQEGLYNELQKDKMAEAYSEIGMKGERRR
GKGHDGLYQGLSTATKDTYDALHMQALPPR (SEQ ID NO: 7)

CD8 leader sequence (amino acids 1-21 of SEQ ID
NO: 7; SEQ ID NO: 8)
MALPVTALLLPLALLLHAARP Anti-LAP scFv (H-L) (amino acids 22-307 of SEQ ID
NO: 7; SEQ ID NO: 9)
MKLWLNWIFLVTLLNDIQCEVKLVESGGGLVQPGGSLSLSCAASGFTFTD
YYMSWVRQPPGKALEWLGFIRNKPNGYTTEYSASVKGRFTISRDNSQSIL
YLQMNVLRAEDSATYYCARYTGGGYFDYWGQGTTLTVSSGGGGSGGGGSG
GGGSGGGGSMMSSAQFLGLLLLCFQGTRCDIQMTQTTSSLSASLGDRLTI
SCRASQDISNYLNWYQQKPDGTVKLLIYYTSRLHSGVPSRFSGSGSGTDY
SLTISNLEQADIATYFCQQGDTLPWTFGGGTKLEIK CD8 hinge/TM domain (amino acids 308-376 of SEQ ID
NO: 7; SEQ ID NO: 10)
TTTPAPRPPTPAPTIASQPLSLRPEACRPAAGGAVHTRGLDFACDIYIWA
PLAGTCGVLLLSLVITLYC 4-1BB ICD (amino acids 377-418 of SEQ ID NO: 7;
SEQ ID NO: 11)
KRGRKKLLYIFKQPFMRPVQTTQEEDGCSCRFPEEEEGGCEL CD3ζ (amino acids 419-530 of SEQ ID NO: 7; SEQ
ID NO: 12).
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR Anti-LAP CAR (L-H)-pMGH 100: CD8 Leader-anti-LAP-CD8 hinge+TM-4-1BB-CD3z (SEQ ID NO: 13) comprising CD8 leader (amino acids 1-21 of SEQ ID NO: 13; SEQ ID NO: 14), anti-LAP scFv (L-H) (amino acids 22-307 of SEQ ID NO: 13; SEQ ID NO: 15), CD8 hinge/TM (amino acids 308-376 of SEQ ID NO: 13; SEQ ID NO: 16), 4-1BB ICD (amino acids 377-418 of SEQ ID NO: 13; SEQ ID NO: 17), and CD3z (amino acids 419-530 of SEQ ID NO: 13; SEQ ID NO: 18).

MALPVTALLLPLALLLHAARPMMSSAQFLGLLLLCFQGTRCDIQMTQTTS
SLSASLGDRLTISCRASQDISNYLNWYQQKPDGTVKLLIYYTSRLHSGVP
SRFSGSGSGTDYSLTISNLEQADIATYFCQQGDTLPWTFGGGTKLEIKGG
GGSGGGGSGGGGSGGGGSMKLWLNWIFLVTLLNDIQCEVKLVESGGGLVQ
PGGSLSLSCAASGFTFTDYYMSWVRQPPGKALEWLGFIRNKPNGYTTEYS
ASVKGRFTISRDNSQSILYLQMNVLRAEDSATYYCARYTGGGYFDYWGQG
TTLTVSSTTTPAPRPPTPAPTIASQPLSLRPEACRPAAGGAVHTRGLDFA
CDIYIWAPLAGTCGVLLLSLVITLYCKRGRKKLLYIFKQPFMRPVQTTQE
EDGCSCRFPEEEEGGCELRVKFSRSADAPAYQQGQNQLYNELNLGRREEY

-continued
DVLDKRRGRDPEMGGKPRRKNPQEGLYNELQKDKMAEAYSEIGMKGERRR

GKGHDGLYQGLSTATKDTYDALHMQALPPR (SEQ ID NO: 13)

CD8 leader (amino acids 1-21 of SEQ ID NO: 13; SEQ ID NO: 14)
MALPVTALLLPLALLLHAARP Anti-LAP scFv (L-H)(amino acids 22-307 of SEQ ID NO: 13; SEQ ID NO: 15)
MMSSAQFLGLLLLCFQGTRCDIQMTQTTSSLSASLGDRLTISCRASQDIS

NYLNWYQQKPDGTVKLLIYYTSRLHSGVPSRFSGSGSGTDYSLTISNLEQ

ADIATYFCQQGDTLPWTFGGGTKLEIKGGGGSGGGGSGGGGSGGGGSMKL

WLNWIFLVTLLNDIQCEVKLVESGGGLVQPGGSLSLSCAASGFTFTDYYM

SWVRQPPGKALEWLGFIRNKPNGYTTEYSASVKGRFTISRDNSQSILYLQ

MNVLRAEDSATYYCARYTGGGYFDYVVGQGTTLTVSS

CD8 hinge/TM (amino acids 308-376 of SEQ ID NO: 13; SEQ ID NO: 16)
TTTPAPRPPTPAPTIASQPLSLRPEACRPAAGGAVHTRGLDFACDIYIWA

PLAGTCGVLLLSLVITLYC 4-1BB ICD (amino acids 377-418 of SEQ ID NO: 13; SEQ ID NO: 17)
KRGRKKLLYIFKQPFMRPVQTTQEEDGCSCRFPEEEEGGCEL CD3z (amino acids 419-530 of SEQ ID NO: 13; SEQ ID NO: 18)
RVKFSRSADAPAYQQGQNQLYNELNLGRREEYDVLDKRRGRDPEMGGKPR

RKNPQEGLYNELQKDKMAEAYSEIGMKGERRRGKHDGLYQGLSTATKDT

YDALHMQALPPR

Anti-EGFR CAR secreting anti-GARP Camelid-pMGH 105: CD8 Leader-anti-EGFR-CD8 hinge+TM-4-1BB-CD3z-anti-GARP camelid (SEQ ID NO: 19) comprising CD8 leader (amino acids 1-21 of SEQ ID NO: 19; SEQ ID NO: 20), anti-EGFR scFv (amino acids 22-267 of SEQ ID NO: 19; SEQ ID NO: 21), CD8 hinge/TM (amino acids 268-336 of SEQ ID NO: 19; SEQ ID NO: 22), 4-1BB (amino acids 337-378 of SEQ ID NO: 19; SEQ ID NO: 23), CD3z (amino acids 379-490 of SEQ ID NO: 19; SEQ ID NO: 24), 2A cleavage sequence (amino acids 494-515 of SEQ ID NO: 19; SEQ ID NO: 31), IgK leader (amino acids 519-539 of SEQ ID NO: 19; SEQ ID NO: 32), and anti-GARP camelid (amino acids 540-646 of SEQ ID NO: 19; SEQ ID NO: 25).

MALPVTALLLPLALLLHAARPQVQLKQSGPGLVQPSQSLSITCTVSGFSL

TNYGVHWVRQSPGKGLEWLGVIWSGGNTDYNTPFTSRLSINKDNSKSQVF

FKMNSLQSNDTAIYYCARALTYYDYEFAYWGQGTLVTVSAGGGGSGGGGS

GGGGSGGGGSDILLTQSPVILSVSPGERVSFSCRASQSIGTNIHWYQQRT

NGSPRLLIKYASESISGIPSRFSGSGSGTDFTLSINSVESEDIADYYCQQ

NNNWPTTFGAGTKLELKTTTPAPRPPTPAPTIASQPLSLRPEACRPAAGG

AVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYS

EIGMKGERRRGKHDGLYQGLSTATKDTYDALHMQALPPRPGSGSGATNF

SLLKQAGDVEENPGPRTAMETDTLLLWVLLLWVPGSTGDDIQMTQSPSSL

SASLGDRVTITCQASQSISSYLAWYQQKPGQAPNILIYGASRLKTGVPSR

FSGSGSGTSFTLTISGLEAEDAGTYYCQQYASVPVTFGQGTKVELKHHHH

HHSG (SEQ ID NO: 19)

CD8 leader (amino acids 1-21 of SEQ ID NO: 19; SEQ ID NO: 20)
MALPVTALLLPLALLLHAARP Anti-EGFR scFv (amino acids 22-267 of SEQ ID NO: 19; SEQ ID NO: 21)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAGGGGSGGGGSGGGGSGGGGSDILLTQSPVIL

SVSPGERVSFSCRASQSIGTNIHWYQQRTNGSPRLLIKYASESISGIPSR

FSGSGSGTDFTLSINSVESEDIADYYCQQNNNWPTTFGAGTKLELK

CD8 hinge/TM (amino acids 268-336 of SEQ ID NO: 19; SEQ ID NO: 22)
TTTPAPRPPTPAPTIASQPLSLRPEACRPAAGGAVHTRGLDFACDIYIWA

PLAGTCGVLLLSLVITLYC 4-1BB (amino acids 337-378 of SEQ ID NO: 19; SEQ ID NO: 23)
KRGRKKLLYIFKQPFMRPVQTTQEEDGCSCRFPEEEEGGCEL CD3z (amino acids 379-490 of SEQ ID NO: 19; SEQ ID NO: 24)
RVKFSRSADAPAYQQGQNQLYNELNLGRREEYDVLDKRRGRDPEMGGKPR

RKNPQEGLYNELQKDKMAEAYSEIGMKGERRRGKHDGLYQGLSTATKDT

YDALHMQALPPR 2A cleavage sequence (amino acids 494-515 of SEQ ID NO: 19; SEQ ID NO: 31)
GSGATNFSLLKQAGDVEENPGP IgK leader (amino acids 519-539 of SEQ ID NO: 19; SEQ ID NO: 32)
METDTLLLWVLLLWVPGSTGD Anti-GARP camelid (amino acids 540-646 of SEQ ID NO: 19; SEQ ID NO: 25).
DIQMTQSPSSLSASLGDRVTITCQASQSISSYLAWYQQKPGQAPNILIYG

ASRLKTGVPSRFSGSGSGTSFTLTISGLEAEDAGTYYCQQYASVPVTFGQ

GTKVELK pMGH113-3C10 scFv-CD8 Hinge/TM-4-1BB ICD-CD3z-P2A-IgK leader-Cetuximab scFv-CD3 scFv-His-tag (SEQ ID NO: 26) comprising 3C10 scFv (amino acids 1-243 of SEQ ID NO: 26; SEQ ID NO: 27), CD8 hinge/TM (amino acids 244-312 of SEQ ID NO: 26; SEQ ID NO: 28), 4-1BB ICD (amino acids 313-354 of SEQ ID NO: 26; SEQ ID NO: 29), CD3z (amino acids 355-466 of SEQ ID NO: 26; SEQ ID NO: 30), P2A (amino acids 467-488 of SEQ ID NO: 26; SEQ ID NO: 31), IgK leader (amino acids 491-511 of SEQ ID NO: 26; SEQ ID NO: 32), Cetuximab scFv (amino acids 512-752 of SEQ ID NO: 26; SEQ ID NO: 33), CD3 scFv (amino acids 758-1000 of SEQ ID NO: 26; SEQ ID NO: 34).

EIQLQQSGAELVKPGASVKLSCTGSGFNIEDYYIHWVKQRTEQGLEWIGR

IDPENDETKYGPIFQGRATITADTSSNTVYLQLSSLTSEDTAVYYCAFRG

GVYWGPGTTLTVSSGGGGSGGGGSGGGGSHMDVVMTQSPLTLSVAIGQSA

SISCKSSQSLLDSDGKTYLNWLLQRPGQSPKRLISLVSKLDSGVPDRFTG

```
SGSGTDFTLRISRVEAEDLGIYYCWQGTHFPGTFGGGTKLEIKTTTPAPR

PPTPAPTIASQPLSLRPEACRPAAGGAVHTRGLDFACDIYIWAPLAGTCG

VLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPRGSGATNFSLLKQAGDVEENPGPPRMETDTLLLWV

LLLWVPGSTGDDILLTQSPVILSVSPGERVSFSCRASQSIGTNIHWYQR

TNGSPRLLIKYASESISGIPSRFSGSGSGTDFTLSINSVESEDIADYYCQ

QNNNWPTTFGAGTKLELKGGGGSGGGGSGGGGSQVQLKQSGPGLVQPSQS

LSITCTVSGFSLTNYGVHWVRQSPGKGLEWLGVIWSGGNTDYNTPFTSRL

SINKDNSKSQVFFKMNSLQSNDTAIYYCARALTYYDYEFAYWGQGTLVTV

SAGGGGSDIKLQQSGAELARPGASVKMSCKTSGYTFTRYTMHWVKQRPGQ

GLEWIGYINPSRGYTNYNQKFKDKATLTTDKSSSTAYMQLSSLTSEDSAV

YYCARYYDDHYCLDYWGQGTTLTVSSVEGGSGGSGGSGGSGGVDDIQLTQ

SPAIMSASPGEKVTMTCRASSSVSYMNWYQQKSGTSPKRWIYDTSKVASG

VPYRFSGSGSGTSYSLTISSMEAEDAATYYCQQWSSNPLTFGAGTKLELK

HHHHHH (SEQ ID NO: 26)

3C10 scFv (amino acids 1-243 of SEQ ID NO: 26; SEQ
ID NO: 27)
EIQLQQSGAELVKPGASVKLSCTGSGFNIEDYYIHWVKQRTEQGLEWIGR

IDPENDETKYGPIFQGRATITADTSSNTVYLQLSSLTSEDTAVYYCAFRG

GVYWGPGTTLTVSSGGGGSGGGGSGGGGSHMDVVMTQSPLTLSVAIGQSA

SISCKSSQSLLDSDGKTYLNWLLQRPGQSPKRLISLVSKLDSGVPDRFTG

SGSGTDFTLRISRVEAEDLGIYYCWQGTHFPGTFGGGTKLEIK

CD8 hinge/TM (amino acids 244-312 of SEQ ID NO:
26; SEQ ID NO: 28)
TTTPAPRPPTPAPTIASQPLSLRPEACRPAAGGAVHTRGLDFACDIYIWA

PLAGTCGVLLLSLVITLYC 4-1BB ICD (amino acids 313-354 of SEQ ID NO: 26;
SEQ ID NO: 29)
KRGRKKLLYIFKQPFMRPVQTTQEEDGCSCRFPEEEEGGCEL CD3z (amino acids 355-466 of SEQ ID NO: 26; SEQ ID
NO: 30)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

P2A (amino acids 467-488 of SEQ ID NO: 26; SEQ ID
NO: 31)
GSGATNFSLLKQAGDVEENPGP IgK leader (amino acids 491-511 of SEQ ID NO: 26;
SEQ ID NO: 32)
METDTLLLWVLLLWVPGSTGD Cetuximab scFv (amino acids 512-752 of SEQ ID NO:
26; SEQ ID NO: 33)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKGGGGSGGGGSGGGGSQVQLKQSGPGLVQPSQSLSITCTVSGFS

LTNYGVHWVRQSPGKGLEWLGVIWSGGNTDYNTPFTSRLSINKDNSKSQV

FFKMNSLQSNDTAIYYCARALTYYDYEFAYWGQGTLVTVSA

CD3 scFv (amino acids 758-1000 of SEQ ID NO: 26;
SEQ ID NO: 34)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK
``` pMGH133-2173 scFv-CD8 Hinge/TM-4-1BB ICD-CD3z-P2A-IgK leader-Cetuximab scFv-CD3 scFv-His-tag (SEQ ID NO: 35) comprising 2173 scFv (amino acids 1-246 of SEQ ID NO: 35; SEQ ID NO: 36), CD8 hinge/TM (amino acids 247-315 of SEQ ID NO: 35; SEQ ID NO: 37), 4-1BB ICD (amino acids 316-357 of SEQ ID NO: 36; SEQ ID NO: 38), CD3z (amino acids 358-469 of SEQ ID NO: 35; SEQ ID NO: 39), P2A (amino acids 470-491 of SEQ ID NO: 35; SEQ ID NO: 40), IgK leader (amino acids 494-514 of SEQ ID NO: 35; SEQ ID NO: 41), Cetuximab scFv (amino acids 515-755 of SEQ ID NO: 35; SEQ ID NO: 42), and CD3 scFv (amino acids 761-1003 of SEQ ID NO: 35; SEQ ID NO: 43).

```
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIKTTTP

APRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPRGSGATNFSLLKQAGDVEENPGPPRMETDTLL

LWVLLLWVPGSTGDDILLTQSPVILSVSPGERVSFSCRASQSIGTNIHWY

QQRTNGSPRLLIKYASESISGIPSRFSGSGSGTDFTLSINSVESEDIADY

YCQQNNNWPTTFGAGTKLELKGGGGSGGGGSGGGGSQVQLKQSGPGLVQP

SQSLSITCTVSGFSLTNYGVHWVRQSPGKGLEWLGVIWSGGNTDYNTPFT

SRLSINKDNSKSQVFFKMNSLQSNDTAIYYCARALTYYDYEFAYWGQGTL

VTVSAGGGGSDIKLQQSGAELARPGASVKMSCKTSGYTFTRYTMHWVKQR

PGQGLEWIGYINPSRGYTNYNQKFKDKATLTTDKSSSTAYMQLSSLTSED

SAVYYCARYYDDHYCLDYWGQGTTLTVSSVEGGSGGSGGSGGSGGVDDIQ

LTQSPAIMSASPGEKVTMTCRASSSVSYMNWYQQKSGTSPKRWIYDTSKV

ASGVPYRFSGSGSGTSYSLTISSMEAEDAATYYCQQWSSNPLTFGAGTKL

ELKHHHHHH (SEQ ID NO: 35)

2173 scFv (amino acids 1-246 of SEQ ID NO: 35; SEQ
ID NO: 36)
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG
```

```
-continued
GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIK
```

CD8 hinge/TM (amino acids 247-315 of SEQ ID NO:
35; SEQ ID NO: 37)
```
TTTPAPRPPTPAPTIASQPLSLRPEACRPAAGGAVHTRGLDFACDIYIWA

PLAGTCGVLLLSLVITLYC
```

4-1BB ICD (amino acids 316-357 of SEQ ID NO: 35;
SEQ ID NO: 38)
```
KRGRKKLLYIFKQPFMRPVQTTQEEDGCSCRFPEEEEGGCEL
```

CD3z (amino acids 358-469 of SEQ ID NO: 35; SEQ ID
NO: 39)
```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

P2A (amino acids 470-491 of SEQ ID NO: 35; SEQ ID
NO: 40)
```
GSGATNFSLLKQAGDVEENPGP
```

IgK leader (amino acids 494-514 of SEQ ID NO: 35;
SEQ ID NO: 41)
```
METDTLLLWVLLLWVPGSTGD
```

Cetuximab scFv (amino acids 515-755 of SEQ ID NO:
35; SEQ ID NO: 42)
```
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKGGGGSGGGGSGGGGSQVQLKQSGPGLVQPSQSLSITCTVSGFS

LTNYGVHWVRQSPGKGLEWLGVIWSGGNTDYNTPFTSRLSINKDNSKSQV

FFKMNSLQSNDTAIYYCARALTYYDYEFAYWGQGTLVTVSA
```

CD3 scFv (amino acids 761-1003 of SEQ ID NO: 35;
SEQ ID NO: 43)
```
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK
``` pMGH134-2173 scFv-CD8 Hinge/TM-4-1BB ICD-CD3z-P2A-IgK leader-CD19scFv-CD3 scFv-His-tag (SEQ ID NO: 44) comprising 2173 scFv (amino acids 1-246 of SEQ ID NO: 44; SEQ ID NO: 45), CD8 hinge/TM (amino acids 247-315 of SEQ ID NO: 44; SEQ ID NO: 46), 4-1BB ICD (amino acids 316-357 of SEQ ID NO: 44; SEQ ID NO: 47), CD3z (amino acids 358-469 of SEQ ID NO: 44; SEQ ID NO: 48), P2A (amino acids 470-491 of SEQ ID NO: 44; SEQ ID NO: 49), IgK leader (amino acids 494-514 of SEQ ID NO: 44; SEQ ID NO: 50), CD19 scFv (amino acids 515-764 of SEQ ID NO: 44; SEQ ID NO: 51), CD3 scFv (amino acids 770-1012 of SEQ ID NO: 44; SEQ ID NO: 52).

```
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR
```

```
-continued
FSGSGSGTDFTLTISSLQAEDVAVYYCWQGTHFPGTFGGGTKVEIKTTTP

APRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPRGSGATNFSLLKQAGDVEENPGPPRMETDTLL

LWVLLLWVPGSTGDDIQLTQSPASLAVSLGQRATISCKASQSVDYDGDSY

LNWYQQIPGQPPKLLIYDASNLVSGIPPRFSGSGSGTDFTLNIHPVEKVD

AATYHCQQSTEDPWTFGGGTKLEIKGGGGSGGGGSGGGGSQVQLQQSGAE

LVRPGSSVKISCKASGYAFSSYWMNWVKQRPGQGLEWIGQIWPGDGDTNY

NGKFKGKATLTADESSSTAYMQLSSLASEDSAVYFCARRETTTVGRYYYA

MDYWGQGTTVTVSSGGGGSDIKLQQSGAELARPGASVKMSCKTSGYTFTR

YTMHWVKQRPGQGLEWIGYINPSRGYTNYNQKFKDKATLTTDKSSSTAYM

QLSSLTSEDSAVYYCARYYDDHYCLDYWGQGTTLTVSSVEGGSGGSGGSG

GSGGVDDIQLTQSPAIMSASPGEKVTMTCRASSSVSYMNWYQQKSGTSPK

RWIYDTSKVASGVPYRFSGSGSGTSYSLTISSMEAEDAATYYCQQWSSNP

LTFGAGTKLELKHHHHHH (SEQ ID NO: 44)
```

2173 scFv (amino acids 1-246 of SEQ ID NO: 44; SEQ
ID NO: 45)
```
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIK
```

CD8 hinge/TM (amino acids 247-315 of SEQ ID NO:
44; SEQ ID NO: 46)
```
TTTPAPRPPTPAPTIASQPLSLRPEACRPAAGGAVHTRGLDFACDIYIWA

PLAGTCGVLLLSLVITLYC
```

4-1BB ICD (amino acids 316-357 of SEQ ID NO: 44;
SEQ ID NO: 47)
```
KRGRKKLLYIFKQPFMRPVQTTQEEDGCSCRFPEEEEGGCEL
```

CD3z (amino acids 358-469 of SEQ ID NO: 44; SEQ ID
NO: 48)
```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

P2A (amino acids 470-491 of SEQ ID NO: 44; SEQ ID
NO: 49)
```
GSGATNFSLLKQAGDVEENPGP
```

IgK leader (amino acids 494-514 of SEQ ID NO: 44;
SEQ ID NO: 50)
```
METDTLLLWVLLLWVPGSTGD
```

CD19 scFv (amino acids 515-764 of SEQ ID NO: 44;
SEQ ID NO: 51)
```
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW
```

-continued
TFGGGTKLEIKGGGGSGGGGSGGGGSQVQLQQSGAELVRPGSSVKISCKA

SGYAFSSYWMNWVKQRPGQGLEWIGQIWPGDGDTNYNGKFKGKATLTADE

SSSTAYMQLSSLASEDSAVYFCARRETTTVGRYYYAMDYWGQGTTVTVSS

CD3 scFv (amino acids 770-1012 of SEQ ID NO: 44;
SEQ ID NO: 52)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK pMGH135-(NFAT response element)-IgK leader-Cetuximab scFv-CD3 scFv-His-tag-(EF1a Promoter)-2173 scFv-CD8 hinge/TM-4-1BB ICD-CD3z (SEQ ID NO: 53) comprising IgK leader (amino acids 1-21 of SEQ ID NO: 53; SEQ ID NO: 54), Cetuximab scFv (amino acids 22-262 of SEQ ID NO: 53; SEQ ID NO: 55), CD3 scFv (amino acids 268-510 of SEQ ID NO: 53; SEQ ID NO: 56), 2173 scFv (amino acids 517-762 of SEQ ID NO: 53; SEQ ID NO: 57), CD8 hinge/TM (amino 763-831 of SEQ ID NO: 53; SEQ ID NO: 58), 4-1BB ICD (amino acids 832-873 of SEQ ID NO: 53; SEQ ID NO: 59), CD3z (amino acids 874-985 of SEQ ID NO: 53; SEQ ID NO: 60).

(NFAT response element)
METDTLLLWVLLLWVPGSTGDDILLTQSPVILSVSPGERVSFSCRASQSI

GTNIHWYQQRTNGSPRLLIKYASESISGIPSRFSGSGSGTDFTLSINSVE

SEDIADYYCQQNNNWPTTFGAGTKLELKGGGGSGGGGSGGGGSQVQLKQS

GPGLVQPSQSLSITCTVSGFSLTNYGVHWVRQSPGKGLEWLGVIWSGGNT

DYNTPFTSRLSINKDNSKSQVFFKMNSLQSNDTAIYYCARALTYYDYEFA

YWGQGTLVTVSAGGGGSDIKLQQSGAELARPGASVKMSCKTSGYTFTRYT

MHWVKQRPGQGLEWIGYINPSRGYTNYNQKFKDKATLTTDKSSSTAYMQL

SSLTSEDSAVYYCARYYDDHYCLDYWGQGTTLTVSSVEGGSGGSGGSGGS

GGVDDIQLTQSPAIMSASPGEKVTMTCRASSSVSYMNWYQQKSGTSPKRW

IYDTSKVASGVPYRFSGSGSGTSYSLTISSMEAEDAATYYCQQWSSNPLT

FGAGTKLELKHHHHHH (EF1a Promoter)
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIKTTTP

APRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPR (SEQ ID NO: 53)

(Note: the two polypeptides noted above are denoted with a single sequence identifier for convenience, but it should be understood that the CAR and BiTE components can be made separately, due to the two separate promoters; see above.)

IgK leader (amino acids 1-21 of SEQ ID NO: 53; SEQ ID NO: 54)
METDTLLLWVLLLWVPGSTGD Cetuximab scFv (amino acids 22-262 of SEQ ID NO: 53; SEQ ID NO: 55)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKGGGGSGGGGSGGGGSQVQLKQSGPGLVQPSQSLSITCTVSGFS

LTNYGVHWVRQSPGKGLEWLGVIWSGGNTDYNTPFTSRLSINKDNSKSQV

FFKMNSLQSNDTAIYYCARALTYYDYEFAYWGQGTLVTVSA

CD3 scFv (amino acids 268-510 of SEQ ID NO: 53; SEQ ID NO: 56)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK 2173 scFv (amino acids 517-762 of SEQ ID NO: 53; SEQ ID NO: 57)
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIK

CD8 hinge/TM (amino acids 763-831 of SEQ ID NO: 53; SEQ ID NO: 58)
TTTPAPRPPTPAPTIASQPLSLRPEACRPAAGGAVHTRGLDFACDIYIWA

PLAGTCGVLLLSLVITLYC 4-1BB ICD (amino acids 832-873 of SEQ ID NO: 53; SEQ ID NO: 59)
KRGRKKLLYIFKQPFMRPVQTTQEEDGCSCRFPEEEEGGCEL CD3z (amino acids 874-985 of SEQ ID NO: 53; SEQ ID NO: 60)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR pMGH136-(NFAT response element)-IgK leader-CD19 scFv-CD3 scFv-His-tag-(EF1a Promoter)-2173 scFv-CD8 Hinge/TM-4-1BB ICD-CD3z (SEQ ID NO:61) comprising (NFAT response element), IgK leader (amino acids 1-21 of SEQ ID NO: 61; SEQ ID NO: 62), CD19 scFv (amino acids 22-271 of SEQ ID NO: 61; SEQ ID NO: 63), CD3 scFv (amino acids 277-519 of SEQ ID NO: 61; SEQ ID NO: 64), 2173 scFv (amino acids 526-771 of SEQ ID NO: 61; SEQ ID NO: 65), CD8 hinge/TM (amino acids 772-840 of SEQ ID NO: 61; SEQ ID NO: 66), 4-1BB ICD (amino acids 841-882 of SEQ ID NO: 61; SEQ ID NO: 67), CD3z (amino acids 883-994 of SEQ ID NO: 61; SEQ ID NO: 68).

METDTLLLWVLLLWVPGSTGDDIQLTQSPASLAVSLGQRATISCKASQSV

DYDGDSYLNWYQQIPGQPPKLLIYDASNLVSGIPPRFSGSGSGTDFTLNI

-continued

```
HPVEKVDAATYHCQQSTEDPWTFGGGTKLEIKGGGGSGGGGSGGGGSQVQ

LQQSGAELVRPGSSVKISCKASGYAFSSYWMNWVKQRPGQGLEWIGQIWP

GDGDTNYNGKFKGKATLTADESSSTAYMQLSSLASEDSAVYFCARRETTT

VGRYYYAMDYWGQGTTVTVSSGGGGSDIKLQQSGAELARPGASVKMSCKT

SGYTFTRYTMHWVKQRPGQGLEWIGYINPSRGYTNYNQKFKDKATLTTDK

SSSTAYMQLSSLTSEDSAVYYCARYYDDHYCLDYWGQGTTLTVSSVEGGS

GGSGGSGGSGGVDDIQLTQSPAIMSASPGEKVTMTCRASSSVSYMNWYQQ

KSGTSPKRWIYDTSKVASGVPYRFSGSGSGTSYSLTISSMEAEDAATYYC

QQWSSNPLTFGAGTKLELKHHHHHH (EF1a Promoter)
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIKTTTP

APRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPR (SEQ ID NO: 61)

(Note: the two polypeptides noted above are
denoted with a single sequence identifier for
convenience, but it should be understood that the
CAR and BiTE components can be made separately,
due to the two separate promoters; see above.)

IgK leader (amino acids 1-21 of SEQ ID NO: 61; SEQ
ID NO: 62)
METDTLLLWVLLLWVPGSTGD CD19 scFv (amino acids 22-271 of SEQ ID NO: 61;
SEQ ID NO: 63)
DIQLTQSPASLAVSLGQRATISCKASQSVDYDGDSYLNWYQQIPGQPPKL

LIYDASNLVSGIPPRFSGSGSGTDFTLNIHPVEKVDAATYHCQQSTEDPW

TFGGGTKLEIKGGGGSGGGGSGGGGSQVQLQQSGAELVRPGSSVKISCKA

SGYAFSSYWMNWVKQRPGQGLEWIGQIWPGDGDTNYNGKFKGKATLTADE

SSSTAYMQLSSLASEDSAVYFCARRETTTVGRYYYAMDYWGQGTTVTVSS

CD3 scFv (amino acids 277-519 of SEQ ID NO: 61;
SEQ ID NO: 64)
DIKLQQSGAELARPGASVKMSCKTSGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSVEGGSGGSGGSGGSGGVDDIQLTQSPAIMSA

SPGEKVTMTCRASSSVSYMNWYQQKSGTSPKRWIYDTSKVASGVPYRFSG

SGSGTSYSLTISSMEAEDAATYYCQQWSSNPLTFGAGTKLELK 2173 scFv (amino acids 526-771 of SEQ ID NO: 61;
SEQ ID NO: 65)
EIQLVQSGAEVKKPGESLRISCKGSGFNIEDYYIHWVRQMPGKGLEWMGR

IDPENDETKYGPIFQGHVTISADTSINTVYLQWSSLKASDTAMYYCAFRG

GVYWGQGTTVTVSSGGGGSGGGGSGGGGSGGGGSDVVMTQSPDSLAVSLG

ERATINCKSSQSLLDSDGKTYLNWLQQKPGQPPKRLISLVSKLDSGVPDR

FSGSGSGTDFTLTISSLQAEDVAVYYCWQGTHFPGTFGGGTKVEIK

CD8 hinge/TM (amino acids 772-840 of SEQ ID NO:
61; SEQ ID NO: 66)
TTTPAPRPPTPAPTIASQPLSLRPEACRPAAGGAVHTRGLDFACDIYIWA

PLAGTCGVLLLSLVITLYC 4-1BB ICD (amino acids 841-882 of SEQ ID NO: 61;
SEQ ID NO: 67)
KRGRKKLLYIFKQPFMRPVQTTQEEDGCSCRFPEEEEGGCEL CD3z (amino acids 883-994 of SEQ ID NO: 61; SEQ ID
NO: 68)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Other aspects of the invention are within the scope of the following numbered paragraphs.

1. A chimeric antigen receptor (CAR) T cell comprising a heterologous nucleic acid molecule, wherein the heterologous nucleic acid molecule comprises:
   (a) a first polynucleotide encoding a CAR comprising an antigen-binding domain, a transmembrane domain, and an intracellular signaling domain; and
   (b) a second polynucleotide encoding a therapeutic agent.

2. The CAR T cell of paragraph 1, wherein the therapeutic agent comprises an antibody reagent.

3. The CAR T cell of paragraph 2, wherein the antibody reagent comprises a single chain antibody or a single domain antibody.

4. The CAR T cell of paragraph 2 or 3, wherein the antibody reagent comprises a bispecific antibody reagent.

5. The CAR T cell of paragraph 4, wherein the bispecific antibody reagent comprises a bispecific T cell engager (BiTE).

6. The CAR T cell of paragraph 3, wherein the single domain antibody comprises a camelid antibody.

7. The CAR T cell of paragraph 1, wherein the therapeutic agent comprises a cytokine.

8. The CAR T cell of any one of paragraphs 1 to 7, wherein the CAR and the therapeutic agent are produced in the form of a polyprotein, which is cleaved to generate separate CAR and therapeutic agent molecules.

9. The CAR T cell of paragraph 8, wherein the polyprotein comprises a cleavable moiety between the CAR and the therapeutic agent.

10. The CAR T cell of paragraph 9, wherein the cleavable moiety comprises a 2A peptide.

11. The CAR T cell of paragraph 10, wherein the 2A peptide comprises P2A or T2A.

12. The CAR T cell of any one of paragraphs 1 to 11, wherein the CAR and the therapeutic agent are each constitutively expressed.

13. The CAR T cell of any one of paragraphs 1 to 12, wherein expression of the CAR and the therapeutic agent is driven by an elongation factor-1 alpha (EF1α) promoter.

14. The CAR T cell of any one of paragraphs 1 to 11, wherein the therapeutic agent is expressed under the control of an inducible promoter, which is optionally inducible by T cell receptor or CAR signaling.

15. The CART cell of paragraph 14, wherein the inducible promoter comprises the NFAT promoter.

16. The CAR T cell of any one of paragraphs 1 to 11, wherein the CAR is expressed under the control of a constitutive promoter and the therapeutic agent is expressed under the control of an inducible promoter, which is optionally inducible by T cell receptor or CAR signaling.

17. The CAR T cell of any one of paragraph 1 to 16, wherein the CAR further comprises one or more co-stimulatory domains.

18. The CAR T cell of any one of paragraphs 1 to 17, wherein the antigen-binding domain of the CAR comprises an antibody, a single chain antibody, a single domain antibody, or a ligand.

19. The CAR T cell of any one of paragraphs 1 to 18, wherein the transmembrane domain of the CAR comprises a CD8 hinge/transmembrane domain, which optionally comprises the sequence of any one of SEQ ID NOs: 4, 10, 16, 22, 28, 37, 46, 58, and 66, or a variant thereof.

20. The CAR T cell of any one of paragraphs 1 to 19, wherein the intracellular signaling domain comprises a CD3ζ intracellular signaling domain, which optionally comprises the sequence of any one of SEQ ID NOs: 6, 12, 18, 24, 30, 39, 48, 60, and 68, or a variant thereof.

21. The CAR T cell of any one of paragraphs 1 to 20, comprising a 4-1BB co-stimulatory domain, which optionally comprises the sequence of any one of SEQ ID NOs: 5, 11, 17, 23, 29, 38, 47, 59, and 67, or a variant thereof.

22. The CAR T cell of any one of paragraphs 1-21, wherein the CAR antigen-binding domain or the therapeutic agent, when the therapeutic agent comprises an antibody reagent, bind to a tumor-associated antigen.

23. The CAR T cell of paragraph 22, wherein the tumor-associated antigen to which the CAR antigen-binding domain or the therapeutic agent binds is a solid tumor-associated antigen.

24. The CAR T cell of paragraph 22 or 23, wherein the tumor-associated antigen to which the CAR antigen-binding domain or the therapeutic agent binds comprises epidermal growth factor receptor variant III (EGFRvIII), EGFR, CD19, prostate-specific membrane antigen (PSMA), or IL-13 receptor alpha 2 (IL-13Rα2), and optionally the CAR antigen-binding domain or the therapeutic agent comprises a sequence selected from the group consisting of SEQ ID NO: 21, 27, 33, 36, 42, 45, 51, 55, 57, 63, 65, and variants thereof.

25. The CAR T cell of any one of paragraphs 1 to 21, wherein the CAR antigen-binding domain or the therapeutic agent, when the therapeutic agent comprises an antibody reagent, binds to a Treg-associated antigen.

26. The CAR T cell of paragraph 25, wherein the Treg-associated antigen to which the CAR antigen-binding domain or the therapeutic agent binds is selected from the group consisting of glycoprotein A repetitions predominant (GARP), latency-associated peptide (LAP), CD25, and cytotoxic T lymphocyte-associated antigen-4 (CTLA-4), and optionally the CAR antigen-binding domain or the therapeutic agent comprises a sequence selected from the group consisting of SEQ ID NO: 3, 9, 15, 25, and variants thereof.

27. A CAR T cell comprising a polynucleotide encoding a CAR, wherein the CAR comprises an antigen-binding domain, a transmembrane domain, and an intracellular signaling domain; and the antigen-binding domain binds to a Treg-associated antigen.

28. The CAR T cell of paragraph 27, wherein the Treg-associated antigen is selected from the group consisting of GARP, LAP, CD25, and CTLA-4.

29. The CAR T cell of paragraph 27 or 28, wherein the CAR further comprises one or more co-stimulatory domains.

30. The CAR T cell of any one of paragraphs 27 to 29, wherein the antigen-binding domain of the CAR comprises a scFv or a single domain antibody, which optionally comprises a sequence selected from the group consisting of SEQ ID NO: 3, 9, 15, 25, and variants thereof.

31. A CAR T cell comprising a heterologous nucleic acid molecule encoding an amino acid sequence having at least 90% sequence identity to the amino acid sequence of any one of SEQ ID NO: 26, SEQ ID NO: 35, SEQ ID NO: 44, SEQ ID NO: 53, SEQ ID NO: 61, SEQ ID NO: 19, SEQ ID NO: 1, SEQ ID NO: 7, and SEQ ID NO: 13.

32. The CAR T cell of paragraph 31, comprising a heterologous nucleic acid molecule encoding an amino acid sequence of any one of SEQ ID NO: 26, SEQ ID NO: 35, SEQ ID NO: 44, SEQ ID NO: 53, SEQ ID NO: 61, SEQ ID NO: 19, SEQ ID NO: 1, SEQ ID NO: 7, and SEQ ID NO: 13.

33. A nucleic acid molecule encoding (i) a CAR polypeptide, or (ii) a polyprotein comprising a CAR polypeptide and a therapeutic agent, of any one of paragraphs 1 to 32.

34. A CAR polypeptide, or polyprotein comprising a CAR polypeptide and a therapeutic agent, of any one of paragraphs 1 to 32.

35. A pharmaceutical composition comprising one or more CAR T cells, nucleic acid molecules, CAR polypeptides, or a polyproteins of any one of paragraphs 1 to 34.

36. A method of treating a patient having cancer, the method comprising administering to the patient a pharmaceutical composition comprising one or more CAR T cell of any one of paragraphs 1-32 or a pharmaceutical composition of paragraph 35.

37. The method of paragraph 36, wherein by targeting the tumor microenvironment, systemic toxicity is reduced.

38. The method of paragraph 36 or 37, wherein the cancer is characterized by the presence of one or more solid tumors.

39. The method of any one of paragraphs 36 to 38, wherein the cancer is characterized by tumor-infiltrating Tregs.

40. The method of any one of paragraphs 36 to 39, wherein the cancer is a glioblastoma.

41. A method of treating a patient having cancer, the method comprising administering to the patient a CAR T cell product, genetically modified to secrete a tumor-toxic antibody or cytokine, wherein by directing the cancer toxicity locally to the tumor microenvironment, systemic toxicity is reduced.

42. The method of paragraph 41, wherein the CAR T cell is genetically modified to deliver an antibody against CTLA4, CD25, GARP, LAP, IL15, CSF1R, or EGFR, or a bispecific antibody against to the tumor microenvironment.

43. The method of paragraph 42, wherein the bispecific antibody is directed against EGFR and CD3.

44. A method of delivering a therapeutic agent to a tissue or organ in a patient to treat a disease or pathology, the method comprising administering to said patient a CAR T cell, genetically modified to secrete a therapeutic antibody, toxin, or agent, wherein the therapeutic antibody, toxin, or agent would, by itself, be unable to enter or penetrate the tissue or organ.

45. The method of paragraph 44, wherein the tissue or organ is in the nervous system.

46. The method of paragraph 45, wherein the nervous system is the central nervous system.

47. The method of paragraph 46, wherein the central nervous system is the brain.

48. The method of any one of paragraphs 44 to 47, wherein the disease or pathology is glioblastoma.

49. The method of paragraph 44, wherein the therapeutic antibody is anti-EGFR (anti-epidermal growth factor receptor) or anti-EGFRvIII.

The following claims are meant to be representative only and not to limit the scope of the disclosed invention. In at least one aspect, we claim:

---

What is claimed is:

1. A chimeric antigen receptor (CAR) T cell comprising a heterologous nucleic acid molecule, wherein the heterologous nucleic acid molecule comprises:
 (a) a first polynucleotide encoding a CAR comprising an antigen-binding domain, a transmembrane domain, and an intracellular signaling domain; and
 (b) a second polynucleotide encoding a bispecific T cell engager (BiTE),
 wherein the CAR and the BiTE are produced in the form of a polyprotein.

2. The CAR T cell of claim 1, wherein the polyprotein is cleaved to generate separate CAR and BiTE molecules.

3. The CAR T cell of claim 2, wherein the polyprotein comprises a cleavable moiety between the CAR and the BiTE.

4. The CAR T cell of claim 1, wherein the CAR and the BiTE are each constitutively expressed.

5. The CAR T cell of claim 1, wherein the BiTE is expressed under the control of an inducible promoter, which is optionally inducible by T cell receptor or CAR signaling.

6. The CAR T cell of claim 5, wherein the inducible promoter comprises the NFAT promoter.

7. The CAR T cell of claim 1, wherein the CAR is expressed under the control of a constitutive promoter and the BiTE is expressed under the control of an inducible promoter, which is optionally inducible by T cell receptor or CAR signaling.

8. The CAR T cell of claim 1, wherein the CAR antigen-binding domain binds to a tumor-associated antigen.

9. The CAR T cell of claim 8, wherein the tumor-associated antigen to which the CAR antigen-binding domain or the BiTE binds is a solid tumor-associated antigen.

10. The CAR T cell of claim 8, wherein the tumor-associated antigen to which the CAR antigen-binding domain or the BiTE binds comprises epidermal growth factor receptor variant III (EGFRvIII), EGFR, CD19, prostate-specific membrane antigen (PSMA), or IL-13 receptor alpha 2 (IL-13Rα2).

11. The CAR T cell of claim 1, wherein the CAR antigen-binding domain or the BiTE, when the BiTE comprises an antibody reagent, binds to a Treg-associated antigen.

12. The CAR T cell of claim 11, wherein the Treg-associated antigen to which the CAR antigen-binding domain or the BiTE binds is selected from the group consisting of glycoprotein A repetitions predominant (GARP), latency-associated peptide (LAP), CD25, and cytotoxic T lymphocyte associated antigen-4 (CTLA-4), and optionally the CAR antigen-binding domain or the BiTE comprises a sequence selected from the group consisting of SEQ ID NO: 3, 9, 15, 25.

13. The CAR T cell of claim 10, wherein the CAR antigen-binding domain or the BiTE comprises a sequence selected from the group consisting of SEQ ID NOs: 21, 27, 33, 36, 42, 45, 51, 55, 57, 63, or 65.

14. The CAR T cell of claim 1, wherein
 the transmembrane domain of the CAR comprises a CD8 hinge/transmembrane domain comprising the sequence of SEQ ID NO: 4.

15. The CAR T cell of claim 1, wherein the heterologous nucleic acid molecule comprises the first polynucleotide located 3' of the second polynucleotide.

16. The CAR T cell of claim 1, wherein the heterologous nucleic acid molecule comprises the first polynucleotide located 5' of the second polynucleotide.

17. The CAR T cell of claim 1, wherein the intracellular signaling domain comprises a CD3 intracellular signaling domain comprising the sequence of SEQ ID NO: 6.

18. The CAR T cell of claim 1, wherein the CAR T cell secretes the BiTE.

19. The CAR T cell of claim 1, wherein the first polynucleotide encoding the CAR comprises an amino acid sequence of SEQ ID NO: 36; and the second polynucleotide encoding the BiTE comprises an amino acid sequence of SEQ ID NO: 42 and an amino acid sequence of SEQ ID NO: 43.

20. The CAR of claim 18, wherein the second polynucleotide encoding the secreted BiTE comprises an amino acid sequence encoding an IgK leader sequence.

21. The CAR T cell of claim 1, wherein the heterologous nucleic acid molecule encodes an amino acid sequence comprising amino acids 1-1003 of SEQ ID NO: 35.

22. The CAR T cell of claim 1, wherein the BiTE binds to EGFR and CD3.

23. The CAR T cell of claim 1, wherein:
 the antigen-binding domain comprises an EGFRVIII antigen binding domain comprising the amino acid sequence of SEQ ID NO: 36:
 the transmembrane domain comprises a CD8 hinge/transmembrane domain comprising the amino acid sequence of SEQ ID NO: 37;
 the intracellular signaling domain comprises:
  a 4-1BB intracellular domain comprising the amino acid sequence of SEQ ID NO: 38; and
  a CD3ζ intracellular signaling domain comprising the amino acid sequence of SEQ ID NO: 39;

the BiTE comprises:
  an IgK leader comprising the amino acid sequence of SEQ ID NO: 41;
  an EGFR binding domain comprising the amino acid sequence of SEQ ID NO: 42; and
  a CD3 binding domain comprising the amino acid sequence of SEQ ID NO: 43; and
  the polyprotein comprises, a P2A peptide between the CAR and the BiTE,
wherein the P2A peptide comprises the amino acid sequence of SEQ ID NO: 40.

24. The CAR T cell of claim 1, wherein:
the polyprotein comprises, from N-terminal to C-terminal: the CAR, a P2A peptide, and the BiTE;
the CAR comprises amino acids 1-469 of SEQ ID NO: 35;
the P2A peptide comprises the amino acid sequence of SEQ ID NO: 40; and
the BiTE comprises amino acids 494-1003 of SEQ ID NO: 35.

* * * * *